(12) United States Patent
Tegg et al.

(10) Patent No.: US 12,714,485 B2
(45) Date of Patent: Aug. 25, 2026

(54) HIGH DENSITY FLAT BALLOON CATHETER

(71) Applicant: St. Jude Medical, Cardiology Division, Inc., Saint Paul, MN (US)

(72) Inventors: Troy T. Tegg, Elk River, MN (US); Gregory K. Olson, Elk River, MN (US); D. Curtis Deno, Andover, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 105 days.

(21) Appl. No.: 18/818,297

(22) Filed: Aug. 28, 2024

(65) Prior Publication Data

US 2024/0415558 A1 Dec. 19, 2024

Related U.S. Application Data

(63) Continuation-in-part of application No. PCT/US2023/086380, filed on Dec. 29, 2023.

(Continued)

(51) Int. Cl.
*A61B 18/14* (2006.01)
*A61B 18/00* (2006.01)

(52) U.S. Cl.
CPC .... *A61B 18/00* (2013.01); *A61B 2018/00077* (2013.01); *A61B 2018/0016* (2013.01);

(Continued)

(58) Field of Classification Search
CPC ......... A61B 18/00; A61B 18/12; A61B 18/14; A61B 2018/00077; A61B 2018/0016;

(Continued)

(56) References Cited

U.S. PATENT DOCUMENTS 4,522,212 A 6/1985 Gelinas et al.
5,224,939 A 7/1993 Holman et al.

(Continued)

FOREIGN PATENT DOCUMENTS

AU 2015202258 A1 5/2015
AU 2016204351 A1 1/2017

(Continued)

OTHER PUBLICATIONS

US 12,220,258 B2, 02/2025, Voth et al. (withdrawn)

*Primary Examiner* — Khadijeh A Vahdat
(74) *Attorney, Agent, or Firm* — Kilpatrick Townsend & Stockton LLP

(57) ABSTRACT

The present invention generally relates to expandable catheters for use in electrophysiology, and more specifically to high-density balloon catheters for use in diagnosing and/or treating cardiac arrhythmias. A catheter includes an elongate catheter shaft comprising a proximal end and a distal end. The elongate catheter shaft defines a longitudinal axis. The catheter includes an expandable assembly having a first delivery configuration and a second deployed configuration. The balloon member includes at least one flexible framework disposed between an outer facing layer and an inner facing layer of the top surface and/or the bottom surface of the balloon member and at least one plurality of electrodes patterned onto the flexible framework. In some embodiments, a flat balloon member includes electrodes on both sides of the planar balloon member. The balloon member may include a flexible structural element disposed within the interior cavity.

20 Claims, 17 Drawing Sheets

Related U.S. Application Data

(60) Provisional application No. 63/685,139, filed on Aug. 20, 2024, provisional application No. 63/558,318, filed on Feb. 27, 2024, provisional application No. 63/603,451, filed on Nov. 28, 2023, provisional application No. 63/448,625, filed on Feb. 27, 2023.

(52) U.S. Cl.
CPC ............... *A61B 2018/00178* (2013.01); *A61B 2018/0022* (2013.01); *A61B 2018/00577* (2013.01); *A61B 2018/00696* (2013.01)

(58) Field of Classification Search
CPC .. A61B 2018/00178; A61B 2018/0022; A61B 2018/00267; A61B 2018/00577; A61B 2018/00696
See application file for complete search history.

(56) References Cited

U.S. PATENT DOCUMENTS 5,380,301 A 1/1995 Prichard et al.
5,400,783 A 3/1995 Pomeranz et al.
5,456,254 A 10/1995 Pietroski et al.
5,626,136 A 5/1997 Webster, Jr.
5,702,438 A 12/1997 Avitall
5,715,817 A 2/1998 Stevens-Wright et al.
5,715,832 A 2/1998 Koblish et al.
5,827,278 A 10/1998 Webster, Jr.
5,846,196 A 12/1998 Siekmeyer et al.
5,876,373 A 3/1999 Giba et al.
5,964,757 A 10/1999 Ponzi
6,029,091 A 2/2000 de la Rama et al.
6,071,282 A 6/2000 Fleischman
6,074,379 A 6/2000 Prichard
6,123,699 A 9/2000 Webster, Jr.
6,171,277 B1 1/2001 Ponzi
6,183,463 B1 2/2001 Webster, Jr.
6,198,974 B1 3/2001 Webster, Jr.
6,210,407 B1 4/2001 Webster
6,267,746 B1 7/2001 Bumbalough
6,273,404 B1 8/2001 Holman et al.
6,415,187 B1 7/2002 Kuzma et al.
6,491,681 B1 12/2002 Kunis et al.
6,522,932 B1 2/2003 Kuzma et al.
6,554,794 B1 4/2003 Mueller et al.
6,652,515 B1 11/2003 Maguire et al.
6,658,302 B1 12/2003 Kuzma et al.
6,961,602 B2 11/2005 Fuimaono et al.
7,004,937 B2 2/2006 Lentz et al.
7,027,851 B2 4/2006 Mejia
7,089,045 B2 8/2006 Fuimaono et al.
7,099,712 B2 8/2006 Fuimaono et al.
7,214,220 B2 5/2007 McGlinch et al.
7,217,256 B2 5/2007 Di Palma
7,228,164 B2 6/2007 Fuimaono et al.
7,257,435 B2 8/2007 Plaza
7,412,274 B2 8/2008 Mejia
7,429,261 B2 9/2008 Kunis et al.
7,561,907 B2 7/2009 Fuimaono et al.
7,608,063 B2 10/2009 Le et al.
7,625,365 B2 12/2009 McGlinch et al.
7,666,204 B2 2/2010 Thornton et al.
7,959,601 B2 6/2011 McDaniel et al.
7,985,215 B2 7/2011 Guo et al.
8,103,327 B2 1/2012 Harlev et al.
8,137,321 B2 3/2012 Argentine
8,157,848 B2 4/2012 Zhang et al.
8,221,390 B2 7/2012 Pal et al.
8,271,099 B1 9/2012 Swanson
8,273,016 B2 9/2012 O'Sullivan
8,376,990 B2 2/2013 Ponzi et al.
8,391,947 B2 3/2013 Urman et al.
8,447,377 B2 5/2013 Harlev et al.
8,486,063 B2 7/2013 Werneth et al.
8,565,894 B2 10/2013 Vetter et al.
8,603,069 B2 12/2013 Selkee
8,608,703 B2 12/2013 Riles et al.
8,649,880 B1 2/2014 Parker, Jr.
8,700,120 B2 4/2014 Koblish
8,706,193 B2 4/2014 Govari et al.
8,744,599 B2 6/2014 Tegg
8,755,861 B2 6/2014 Harlev et al.
8,771,267 B2 7/2014 Kunis et al.
8,777,929 B2 7/2014 Schneider et al.
8,792,962 B2 7/2014 Esguerra et al.
8,814,824 B2 8/2014 Kauphusman et al.
8,814,825 B2 8/2014 Tegg et al.
8,880,158 B2 11/2014 Spector
8,882,705 B2 11/2014 McDaniel et al.
8,894,610 B2 11/2014 Macnamara et al.
8,979,841 B2 3/2015 Kunis et al.
8,996,091 B2 3/2015 de la Rama et al.
9,017,308 B2 4/2015 Klisch et al.
9,033,893 B2 5/2015 Spector
9,033,917 B2 5/2015 Magana et al.
9,044,245 B2 6/2015 Condie et al.
9,050,010 B2 6/2015 Bui et al.
9,101,733 B2 8/2015 McDaniel
9,204,929 B2 12/2015 Solis
9,216,056 B2 12/2015 Datta et al.
9,247,990 B2 2/2016 Kauphusman et al.
9,254,093 B2 2/2016 Spector
9,282,908 B2 3/2016 Spector
9,326,815 B2 5/2016 Watson
9,339,631 B2 5/2016 Graham et al.
9,433,751 B2 9/2016 Ponzi et al.
9,433,752 B2 9/2016 Jimenez et al.
9,468,495 B2 10/2016 Kunis et al.
9,474,486 B2 10/2016 Eliason et al.
9,486,280 B2 11/2016 Koblish et al.
9,486,282 B2 11/2016 Solis
9,522,035 B2 12/2016 Highsmith
9,532,703 B2 1/2017 Huszar et al.
9,539,413 B2 1/2017 Ogle
9,629,675 B2 4/2017 Kleshinski et al.
9,649,158 B2 5/2017 Datta et al.
9,687,166 B2 6/2017 Subramaniam et al.
9,693,699 B2 7/2017 Spector et al.
9,693,733 B2 7/2017 Altmann et al.
9,694,159 B2 7/2017 Schneider et al.
9,694,161 B2 7/2017 Selkee
9,706,935 B2 7/2017 Spector
9,713,418 B2 7/2017 Huszar et al.
9,788,895 B2 10/2017 Solis
9,820,664 B2 11/2017 Hoitink et al.
9,833,608 B2 12/2017 Masson
9,844,645 B2 12/2017 Pai et al.
9,848,795 B2 12/2017 Marecki et al.
9,907,480 B2 3/2018 Basu et al.
9,919,132 B2 3/2018 Tegg et al.
9,949,656 B2 4/2018 Wu et al.
9,986,949 B2 6/2018 Govari et al.
10,004,877 B2 6/2018 Tegg
10,034,637 B2 7/2018 Harlev et al.
10,052,457 B2 8/2018 Nguyen et al.
10,065,019 B2 9/2018 Hamuro et al.
10,099,036 B2 10/2018 Heideman et al.
10,118,022 B2 11/2018 Helgeson et al.
10,130,423 B1 11/2018 Viswanathan et al.
10,136,829 B2 11/2018 Deno et al.
10,143,394 B2 12/2018 Solis
10,172,673 B2 1/2019 Viswanathan et al.
10,285,610 B2 5/2019 Wu
10,322,261 B2 6/2019 Pai et al.
10,362,952 B2 7/2019 Basu et al.
10,362,954 B2 7/2019 de la Rama et al.
10,376,170 B2 8/2019 Quinn et al.
10,384,036 B2 8/2019 Romoscanu
10,398,500 B2 9/2019 Huszar et al.
10,470,682 B2 11/2019 Deno et al.
10,478,247 B2 11/2019 Litscher et al.
10,478,325 B2 11/2019 Syed
10,492,729 B2 12/2019 de la Rama et al.

(56) References Cited

U.S. PATENT DOCUMENTS 10,506,938 B2 12/2019 Wu et al.
10,537,259 B2 1/2020 Wu et al.
10,542,899 B2 1/2020 Wu et al.
10,556,091 B2 2/2020 Truhler et al.
10,575,742 B2 3/2020 Wu et al.
10,575,745 B2 3/2020 Solis
10,578,737 B2 3/2020 Gliner et al.
10,595,738 B2 3/2020 Sterrett et al.
10,595,740 B2 3/2020 Hoitink et al.
10,602,948 B2 3/2020 Wu et al.
10,646,692 B2 5/2020 Tegg et al.
10,653,423 B2 5/2020 Starnes
10,702,177 B2 7/2020 Aujla
10,702,178 B2 7/2020 Dahlen et al.
10,702,677 B2 7/2020 Okamura et al.
10,737,060 B2 8/2020 Gupta et al.
10,813,590 B2 10/2020 Ruppersberg
10,835,712 B2 11/2020 Wada
10,842,990 B2 11/2020 de la Rama et al.
10,857,349 B2 12/2020 de la Rama et al.
10,869,992 B2 12/2020 Pai et al.
10,898,685 B2 1/2021 Tegg
10,905,347 B2 2/2021 Fuentes-ortega et al.
10,912,476 B2 2/2021 Spector
10,912,925 B2 2/2021 Houck
10,932,685 B2 3/2021 Wu
10,945,626 B2 3/2021 Fuentes-Ortega et al.
10,946,167 B2 3/2021 Mintz et al.
10,953,196 B2 3/2021 Raab et al.
10,959,636 B2 3/2021 Dahlen et al.
10,966,623 B2 4/2021 Wu et al.
10,966,753 B2 4/2021 Coyle et al.
10,967,150 B2 4/2021 Helgeson et al.
10,973,427 B2 4/2021 Aujla
10,987,045 B2 4/2021 Basu et al.
11,033,715 B2 6/2021 Beeckler et al.
11,039,772 B2 6/2021 Wu et al.
11,039,773 B2 6/2021 Sterrett et al.
11,077,298 B2 8/2021 Waldhauser et al.
11,083,400 B2 8/2021 Hoitink et al.
11,089,987 B2 8/2021 Spector
11,116,436 B2 9/2021 Wu et al.
11,116,476 B2 9/2021 Buesseler et al.
11,116,942 B2 9/2021 Beeckler et al.
11,123,051 B2 9/2021 Van Der Linde et al.
11,141,568 B2 10/2021 Hsueh et al.
11,160,482 B2 11/2021 Solis
11,172,858 B2 11/2021 Olson et al.
D940,310 S 1/2022 de la Rama et al.
11,272,886 B2 3/2022 Harlev et al.
D951,438 S 5/2022 de la Rama et al.
D952,140 S 5/2022 de la Rama et al.
D952,843 S 5/2022 de la Rama et al.
11,382,690 B2 7/2022 Smith et al.
11,382,743 B2 7/2022 Marchand et al.
11,383,078 B2 7/2022 de la Rama et al.
11,419,673 B2 8/2022 Kauphusman et al.
11,426,111 B2 8/2022 Olson
11,433,220 B2 9/2022 Oliverius et al.
11,439,318 B2 9/2022 Olson et al.
11,439,460 B2 9/2022 Sliwa et al.
11,446,470 B2 9/2022 Castelli et al.
11,446,471 B2 9/2022 Grunewald
D966,506 S 10/2022 de la Rama et al.
D966,507 S 10/2022 de la Rama et al.
11,478,299 B2 10/2022 Webster et al.
11,484,690 B2 11/2022 Tegg et al.
11,491,311 B2 11/2022 Selkee
11,504,205 B2 11/2022 Brucker et al.
11,511,078 B2 11/2022 Gonzalez
11,517,715 B2 12/2022 Govari
11,517,716 B2 12/2022 Nguyen et al.
11,523,748 B2 12/2022 Esguerra Wilczynski et al.
11,540,876 B2 1/2023 Oliverius et al.
11,540,878 B2 1/2023 Fuentes-Ortega et al.
11,547,437 B2 1/2023 Zarembinski
11,553,962 B2 1/2023 Harlev et al.
11,559,663 B2 1/2023 Hannon et al.
11,583,334 B2 2/2023 Caples et al.
11,583,658 B2 2/2023 Yang et al.
11,602,630 B2 3/2023 Vetter et al.
11,617,616 B2 4/2023 Clark et al.
11,617,859 B2 4/2023 Hsueh et al.
11,617,861 B2 4/2023 Pai et al.
11,622,806 B2 4/2023 Romoscanu
11,628,009 B2 4/2023 Aujla
11,642,064 B2 5/2023 Sterrett et al.
11,660,119 B2 5/2023 Hassett
11,672,947 B2 6/2023 Tegg et al.
11,684,473 B2 6/2023 Righini et al.
11,690,552 B2 7/2023 Wu et al.
11,723,574 B2 8/2023 Wu et al.
11,771,373 B2 10/2023 Nakar et al.
11,779,770 B2 10/2023 Botzer
11,786,301 B2 10/2023 Olson
11,806,152 B2 11/2023 Zeidan et al.
11,813,410 B2 11/2023 Olson et al.
11,832,965 B2 12/2023 Wang
11,850,051 B2 12/2023 Selkee et al.
11,857,250 B2 1/2024 Corvi et al.
11,896,819 B2 2/2024 Rosa et al.
11,904,109 B2 2/2024 Gliner et al.
11,938,316 B2 3/2024 Feler et al.
11,950,827 B2 4/2024 Rafiee et al.
11,950,840 B2 4/2024 Govari et al.
11,950,841 B2 4/2024 Govari et al.
11,950,897 B2 4/2024 Esguerra Wilczynski et al.
11,950,930 B2 4/2024 Gliner et al.
11,957,847 B2 4/2024 Houck
11,992,321 B2 5/2024 Solis
12,004,804 B2 6/2024 Govari et al.
12,004,805 B2 6/2024 Schuler et al.
12,011,216 B2 6/2024 Zirkle et al.
12,036,027 B2 7/2024 Olson et al.
12,036,371 B2 7/2024 Hsueh et al.
12,064,168 B2 8/2024 Harlev et al.
12,076,079 B2 9/2024 Oliverius et al.
12,083,288 B2 9/2024 Lopez et al.
12,089,940 B2 9/2024 Hoitink et al.
12,097,034 B2 9/2024 Wu et al.
12,102,382 B2 10/2024 Govari et al.
12,109,031 B2 10/2024 Deno et al.
12,109,373 B2 10/2024 Srivastava et al.
12,114,922 B2 10/2024 Harlev et al.
12,121,357 B2 10/2024 De La Rama et al.
12,121,438 B2 10/2024 Dehdashtian et al.
12,138,404 B2 11/2024 Beeckler et al.
12,144,629 B2 11/2024 Wu et al.
12,171,488 B2 12/2024 Narayan et al.
12,178,500 B2 12/2024 Highsmith
12,185,961 B2 1/2025 Nguyen et al.
12,186,010 B2 1/2025 Govari et al.
12,193,728 B2 1/2025 Narayan
12,193,823 B2 1/2025 Wu et al.
12,194,251 B2 1/2025 Tavallaei et al.
12,201,351 B2 1/2025 Kim et al.
12,201,421 B2 1/2025 Garai et al.
12,207,795 B2 1/2025 Purohit et al.
12,214,206 B2 2/2025 Ward et al.
12,220,541 B2 2/2025 Highsmith et al.
12,221,163 B2 2/2025 Günther et al.
12,226,141 B2 2/2025 Yaffe et al.
12,226,314 B2 2/2025 Reimer et al.
12,232,755 B2 2/2025 Phan et al.
12,232,874 B2 2/2025 Salazar et al.
12,232,908 B2 2/2025 Stigall et al.
12,239,364 B2 3/2025 Govari et al.
12,246,143 B2 3/2025 Leeflang et al.
12,251,224 B2 3/2025 Selkee et al.
12,256,913 B2 3/2025 Nunan
12,256,984 B2 3/2025 Ku et al.
12,256,985 B2 3/2025 Zhou et al.
12,263,014 B2 4/2025 Tegg et al.
12,263,338 B2 4/2025 de la Rama et al.

(56) References Cited

U.S. PATENT DOCUMENTS 12,268,456 B2 4/2025 Harlev et al.
12,290,646 B2 5/2025 Osypka et al.
12,310,715 B2 5/2025 Hoitink et al.
D1,078,039 S 6/2025 Tegg et al.
12,324,620 B2 6/2025 de la Rama et al.
12,337,124 B2 6/2025 Campbell et al.
2002/0165484 A1 11/2002 Bowe et al.
2005/0159741 A1 7/2005 Paul et al.
2009/0198300 A1 8/2009 Zhang et al.
2011/0118726 A1 5/2011 de la Rama et al.
2012/0271302 A1 10/2012 Behl et al.
2012/0296232 A1 11/2012 Ng
2013/0253504 A1 9/2013 Fang
2013/0274582 A1 10/2013 Afonso et al.
2013/0282084 A1* 10/2013 Mathur .............. A61B 18/1492 607/101
2014/0100639 A1 4/2014 Lee et al.
2014/0200639 A1 7/2014 de la Rama
2014/0269602 A1 9/2014 Kawagishi
2014/0296902 A1 10/2014 Huszar et al.
2014/0316496 A1 10/2014 Masson et al.
2014/0336636 A1 11/2014 Huszar et al.
2014/0350564 A1 11/2014 Huszar et al.
2015/0001191 A1 1/2015 Lee et al.
2015/0105645 A1 4/2015 Subramaniam et al.
2015/0141785 A1 5/2015 Hayam et al.
2015/0159741 A1 6/2015 Versteyhe et al.
2015/0351652 A1 12/2015 Marecki et al.
2015/0359558 A1* 12/2015 Kardosh ................ A61N 7/022 606/169
2016/0143588 A1 5/2016 Hoitink et al.
2016/0213423 A1 7/2016 Kauphusman et al.
2016/0213916 A1 7/2016 de la Rama
2016/0278851 A1 9/2016 Mannion et al.
2016/0317094 A1 11/2016 Byrd et al.
2016/0331471 A1 11/2016 Deno et al.
2016/0331933 A1 11/2016 Knutsen
2016/0374582 A1 12/2016 Wu et al.
2016/0374753 A1 12/2016 Wu et al.
2017/0000365 A1 1/2017 Wu et al.
2017/0042449 A1 2/2017 Deno et al.
2017/0049348 A1 2/2017 Deno et al.
2017/0112404 A1 4/2017 de la Rama et al.
2017/0112405 A1 4/2017 Sterrett et al.
2017/0273738 A1 9/2017 Wu
2017/0319269 A1 11/2017 Oliverius et al.
2017/0367756 A1 12/2017 Sliwa et al.
2018/0042667 A1 2/2018 Pappone et al.
2018/0056038 A1 3/2018 Aujla
2018/0070845 A1 3/2018 Hoitink et al.
2018/0085064 A1 3/2018 Auerbach et al.
2018/0116539 A1 5/2018 Olson et al.
2018/0161093 A1 6/2018 Basu et al.
2018/0193089 A1 7/2018 Wu
2018/0229030 A1 8/2018 Dubuclet et al.
2018/0235496 A1 8/2018 Wu et al.
2018/0303361 A1 10/2018 Wu et al.
2018/0335519 A1 11/2018 Gliner et al.
2018/0369574 A1 12/2018 Dubuclet et al.
2019/0009052 A1 1/2019 Oliverius et al.
2019/0125378 A1 5/2019 Shelton, IV et al.
2019/0175043 A1 6/2019 Wu et al.
2019/0192826 A1 6/2019 Wada
2019/0239812 A1 8/2019 Botzer et al.
2020/0000359 A1 1/2020 de la Rama et al.
2020/0054391 A1 2/2020 Litscher et al.
2020/0069365 A1 3/2020 Harlev et al.
2020/0077908 A1 3/2020 Hagfors et al.
2020/0113469 A1 4/2020 Sahadevan et al.
2020/0121894 A1 4/2020 Prabhu et al.
2020/0138319 A1 5/2020 Spector
2020/0138378 A1 5/2020 de la Rama et al.
2020/0155021 A1 5/2020 Wu et al.
2020/0205737 A1 7/2020 Beeckler
2020/0214635 A1 7/2020 Dahlen et al.
2020/0221966 A1 7/2020 Wu et al.
2020/0229726 A1 7/2020 Sterrett et al.
2020/0229727 A1 7/2020 Hoitink et al.
2020/0229866 A1 7/2020 Harlev et al.
2020/0253496 A1 8/2020 Deno et al.
2020/0305744 A1 10/2020 Weerakoon et al.
2020/0329989 A1 10/2020 Aujla
2020/0345262 A1 11/2020 Selkee et al.
2020/0360657 A1 11/2020 Ganske
2020/0398026 A1 12/2020 Castelli et al.
2020/0405166 A1 12/2020 Wu et al.
2021/0015551 A1 1/2021 Fuentes-ortega et al.
2021/0038860 A1 2/2021 Mintz et al.
2021/0059745 A1 3/2021 Highsmith
2021/0068693 A1 3/2021 Fuentes-ortega et al.
2021/0077183 A1 3/2021 Shubhayu et al.
2021/0085920 A1 3/2021 Roberts et al.
2021/0085921 A1 3/2021 Roberts et al.
2021/0121231 A1 4/2021 Basu et al.
2021/0145342 A1 5/2021 Wang
2021/0153932 A1 5/2021 Voth et al.
2021/0187246 A1 6/2021 Houck
2021/0204871 A1 7/2021 Goedeke et al.
2021/0228136 A1 7/2021 Fuentes-ortega et al.
2021/0228137 A1 7/2021 Aujla
2021/0267693 A1 9/2021 Deno et al.
2021/0268234 A1 9/2021 Helgeson et al.
2021/0298656 A1 9/2021 Wu et al.
2021/0361216 A1 11/2021 Hoitink et al.
2021/0361220 A1 11/2021 Olson
2021/0361428 A1 11/2021 Dixon
2021/0369132 A1 12/2021 Van Niekerk et al.
2021/0369338 A1 12/2021 Govari et al.
2021/0369339 A1 12/2021 Salazar et al.
2021/0370022 A1 12/2021 Bean et al.
2021/0401345 A1 12/2021 Wu et al.
2021/0402148 A1 12/2021 Beeckler et al.
2022/0008011 A1 1/2022 Olson
2022/0015678 A1 1/2022 Spector
2022/0023594 A1 1/2022 Pai
2022/0054066 A1 2/2022 Solis
2022/0054198 A1 2/2022 Tegg et al.
2022/0061727 A1 3/2022 Olson et al.
2022/0071704 A1 3/2022 Le
2022/0079496 A1 3/2022 Squires et al.
2022/0104872 A1* 4/2022 Govari ................ A61B 5/6858
2022/0110675 A1 4/2022 Govari et al.
2022/0126063 A1 4/2022 Weber
2022/0175294 A1 6/2022 Spector
2022/0175445 A1 6/2022 Sutermeister et al.
2022/0225941 A1 7/2022 Smaill et al.
2022/0265345 A1 8/2022 Gottsche et al.
2022/0273913 A1 9/2022 Worley et al.
2022/0313353 A1 10/2022 Palushi et al.
2022/0313961 A1 10/2022 Tang
2022/0331553 A1 10/2022 Strom et al.
2022/0354568 A1 11/2022 Pappone et al.
2022/0361942 A1 11/2022 Lichter et al.
2022/0370119 A1 11/2022 Govari et al.
2022/0370121 A1 11/2022 Highsmith
2022/0370122 A1 11/2022 Smail
2022/0370792 A1 11/2022 de la Rama et al.
2022/0387012 A1 12/2022 Nunan
2022/0387099 A1 12/2022 Cohen et al.
2022/0387100 A1 12/2022 Greenbaum et al.
2022/0395214 A1 12/2022 Altman et al.
2022/0401032 A1 12/2022 Govari et al.
2022/0401693 A1 12/2022 Oliverius et al.
2022/0409860 A1 12/2022 Castelli et al.
2023/0000415 A1 1/2023 Olson
2023/0000547 A1 1/2023 Viswanathan et al.
2023/0000548 A1 1/2023 Viswanathan
2023/0000550 A1 1/2023 Nedved et al.
2023/0001148 A1 1/2023 Sharma
2023/0008044 A1 1/2023 Rao et al.
2023/0009573 A1 1/2023 Van Niekerk et al.
2023/0011509 A1 1/2023 Sterrett et al.
2023/0012307 A1 1/2023 Harlev et al.
2023/0024690 A1 1/2023 Cohen et al.

(56) References Cited

U.S. PATENT DOCUMENTS

2023/0028549 A1 1/2023 Maierhofer et al.
2023/0029648 A1 2/2023 Van Niekerk et al.
2023/0033444 A1 2/2023 Knighton et al.
2023/0035917 A1 2/2023 Gutbrod et al.
2023/0043627 A1 2/2023 Tang et al.
2023/0043978 A1 2/2023 Govari
2023/0046955 A1 2/2023 Akagane
2023/0049942 A1 2/2023 Narayan et al.
2023/0052130 A1 2/2023 Govari et al.
2023/0053064 A1 2/2023 Altmann
2023/0055089 A1 2/2023 Govari et al.
2023/0064082 A1 3/2023 Sun et al.
2023/0078216 A1 3/2023 Govari
2023/0083615 A1 3/2023 Nguyen et al.
2023/0084626 A1 3/2023 Grunewald
2023/0105390 A1 4/2023 Gutbrod et al.
2023/0105973 A1 4/2023 Gutbrod et al.
2023/0114222 A1 4/2023 Esguerra Wilczynski et al.
2023/0121397 A1 4/2023 Oliverius et al.
2023/0123266 A1 4/2023 Castelli et al.
2023/0149069 A1 5/2023 Niekerk et al.
2023/0149070 A1 5/2023 Olson et al.
2023/0149675 A1 5/2023 Leung et al.
2023/0172611 A1 6/2023 Biscarrat et al.
2023/0172659 A1 6/2023 Olson et al.
2023/0172661 A1 6/2023 Harlev et al.
2023/0190166 A1 6/2023 Spector
2023/0190198 A1 6/2023 Pederson et al.
2023/0190369 A1 6/2023 Caples et al.
2023/0200894 A1 6/2023 Rodriguez et al.
2023/0200895 A1 6/2023 Ebrahimi et al.
2023/0210433 A1 7/2023 Abbas et al.
2023/0264031 A1 8/2023 Harlev et al.
2023/0284956 A1 9/2023 Wu et al.
2023/0310071 A1 10/2023 Van Niekerk et al.
2023/0329577 A1 10/2023 Cao et al.
2023/0329618 A1 10/2023 Wu et al.
2023/0329784 A1 10/2023 Stewart et al.
2023/0337956 A1 10/2023 Rodriguez Soto
2023/0346455 A1 11/2023 Beeckler et al.
2023/0380746 A1 11/2023 Van Niekerk et al.
2023/0404657 A1 12/2023 Olson
2023/0405338 A1 12/2023 Botzer
2023/0414156 A1 12/2023 Liu et al.
2024/0008920 A1 1/2024 Govari et al.
2024/0023865 A1 1/2024 Wong et al.
2024/0033470 A1 2/2024 Olson et al.
2024/0057939 A1 2/2024 Wang
2024/0058073 A1 2/2024 Govari
2024/0065755 A1 2/2024 Ebrahimi et al.
2024/0081712 A1 3/2024 Selkee et al.
2024/0081905 A1 3/2024 Corvi et al.
2024/0099660 A1 3/2024 Ebner et al.
2024/0123191 A1 4/2024 Highsmith et al.
2024/0156524 A1 5/2024 Ebrahimi et al.
2024/0164686 A1 5/2024 Ghosalker et al.
2024/0173070 A1 5/2024 Selkee et al.
2024/0180614 A1 6/2024 Keyes et al.
2024/0180615 A1 6/2024 Jenkins et al.
2024/0189023 A1 6/2024 Vu et al.
2024/0197231 A1 6/2024 Rorick
2024/0197234 A1 6/2024 Govari
2024/0197389 A1 6/2024 Van Niekerk et al.
2024/0197391 A1 6/2024 Okarski et al.
2024/0197392 A1 6/2024 Van Niekerk et al.
2024/0197393 A1 6/2024 Kingston et al.
2024/0197394 A1 6/2024 Hagstrom et al.
2024/0198054 A1 6/2024 Schultz
2024/0206965 A1 6/2024 Beeckler et al.
2024/0206966 A1 6/2024 Kelly et al.
2024/0207578 A1 6/2024 Soltis et al.
2024/0215893 A1 7/2024 Van Niekerk et al.
2024/0215894 A1 7/2024 Van Niekerk et al.
2024/0215918 A1 7/2024 Beeckler et al.
2024/0215920 A1 7/2024 Van Niekerk et al.
2024/0215921 A1 7/2024 Rodriguez Soto et al.
2024/0216043 A1 7/2024 Govari et al.
2024/0216048 A1 7/2024 Suarez
2024/0216050 A1 7/2024 Rodriguez Soto
2024/0216056 A1 7/2024 Keyes et al.
2024/0216645 A1 7/2024 Kahlon
2024/0225726 A1 7/2024 Govari et al.
2024/0237946 A1 7/2024 Voth et al.
2024/0238041 A1 7/2024 Shuros et al.
2024/0245360 A1 7/2024 Gliner et al.
2024/0252801 A1 8/2024 Cohen et al.
2024/0252815 A1 8/2024 de la Rama et al.
2024/0260932 A1 8/2024 Masters et al.
2024/0277277 A1 8/2024 Hoitink et al.
2024/0277404 A1 8/2024 Shuros et al.
2024/0285923 A1 8/2024 Sharma et al.
2024/0306900 A1 9/2024 Thissen et al.
2024/0325691 A1 10/2024 Bogusky
2024/0350063 A1 10/2024 Olson et al.
2024/0350070 A1 10/2024 Rodriguez
2024/0366299 A1 11/2024 Dando et al.
2024/0366301 A1 11/2024 Govari et al.
2024/0415438 A1 12/2024 Wu et al.
2024/0423707 A1 12/2024 Govari et al.
2025/0009272 A1 1/2025 de la Rama et al.
2025/0017648 A1 1/2025 Kim
2025/0025231 A1 1/2025 Oliverius et al.
2025/0025296 A1 1/2025 Rothfuss et al.
2025/0025643 A1 1/2025 Sigmon, Jr. et al.
2025/0032028 A1 1/2025 Deno et al.
2025/0032181 A1 1/2025 Harlev et al.
2025/0032749 A1 1/2025 Tao et al.
2025/0040853 A1 2/2025 Wu et al.
2025/0040889 A1 2/2025 Smaill et al.
2025/0040955 A1 2/2025 Murray et al.
2025/0043590 A1 2/2025 Furseth et al.
2025/0049460 A1 2/2025 Worrell et al.
2025/0057595 A1 2/2025 Narayan et al.
2025/0064430 A1 2/2025 Mantri et al.
2025/0064512 A1 2/2025 Kasher et al.
2025/0064585 A1 2/2025 Vidlund et al.
2025/0072897 A1 3/2025 Reu et al.
2025/0082438 A1 3/2025 Seeralan et al.
2025/0082901 A1 3/2025 Govari et al.
2025/0082903 A1 3/2025 Hsueh et al.
2025/0090070 A1 3/2025 Wu et al.
2025/0090151 A1 3/2025 Pedersen et al.
2025/0090225 A1 3/2025 Savastano et al.
2025/0090807 A1 3/2025 Padilla et al.
2025/0099176 A1 3/2025 Kim et al.
2025/0127567 A1 4/2025 Highsmith
2025/0152104 A1 5/2025 Tegg et al.
2025/0152932 A1 5/2025 de la Rama et al.
2025/0160942 A1 5/2025 Ku et al.
2025/0177037 A1 6/2025 Olson et al.
2025/0185968 A1 6/2025 Salazar et al.
2025/0185969 A1 6/2025 Selkee et al.

FOREIGN PATENT DOCUMENTS

AU 2016204353 A1 1/2017
AU 2016204355 A1 1/2017
CA 2934209 A1 12/2016
CA 2934211 A1 12/2016
CA 2934214 A1 12/2016
CN 101797181 A 8/2010
CN 101927053 B 1/2015
CN 103157168 B 4/2015
CN 105960201 A 9/2016
CN 106859765 A 6/2017
CN 106901831 A 6/2017
CN 206880930 U 1/2018
CN 104958824 B 12/2018
CN 104434083 B 4/2019
CN 104968261 B 5/2019
CN 105592778 B 7/2019
CN 105960200 B 8/2019
CN 105451680 B 10/2019
CN 110536646 A 12/2019

(56) References Cited

FOREIGN PATENT DOCUMENTS

| | | | |
|---|---|---|---|
| CN | 110604860 | A | 12/2019 |
| CN | 105960201 | B | 3/2020 |
| CN | 111225627 | A | 6/2020 |
| CN | 111227929 | A | 6/2020 |
| CN | 111374755 | A | 7/2020 |
| CN | 111432739 | A | 7/2020 |
| CN | 111657866 | A | 9/2020 |
| CN | 111839499 | A | 10/2020 |
| CN | 106264715 | B | 11/2020 |
| CN | 106264716 | B | 11/2020 |
| CN | 112040861 | A | 12/2020 |
| CN | 106308790 | B | 6/2021 |
| CN | 107529958 | B | 7/2021 |
| CN | 109310469 | B | 7/2021 |
| CN | 213665310 | U | 7/2021 |
| CN | 213821695 | U | 7/2021 |
| CN | 109641121 | B | 9/2021 |
| CN | 109952123 | B | 9/2021 |
| CN | 110545874 | B | 9/2021 |
| CN | 110559544 | B | 9/2021 |
| CN | 113425304 | A | 9/2021 |
| CN | 105615994 | B | 10/2021 |
| CN | 109963610 | B | 11/2021 |
| CN | 113939327 | A | 1/2022 |
| CN | 108289709 | B | 3/2022 |
| CN | 114126522 | A | 3/2022 |
| CN | 114343831 | A | 4/2022 |
| CN | 114375211 | A | 4/2022 |
| CN | 216257368 | U | 4/2022 |
| CN | 114424971 | A | 5/2022 |
| CN | 111246907 | B | 7/2022 |
| CN | 114727815 | A | 7/2022 |
| CN | 114828745 | A | 7/2022 |
| CN | 107773300 | B | 8/2022 |
| CN | 108567424 | B | 8/2022 |
| CN | 114903491 | A | 8/2022 |
| CN | 106859638 | B | 10/2022 |
| CN | 108283520 | B | 10/2022 |
| CN | 110547865 | B | 10/2022 |
| CN | 115137944 | A | 10/2022 |
| CN | 107343816 | B | 11/2022 |
| CN | 113545841 | B | 11/2022 |
| CN | 115281680 | A | 11/2022 |
| CN | 115300752 | A | 11/2022 |
| CN | 115363736 | A | 11/2022 |
| CN | 115363746 | A | 11/2022 |
| CN | 115364333 | A | 11/2022 |
| CN | 115379873 | A | 11/2022 |
| CN | 217793303 | U | 11/2022 |
| CN | 115426941 | A | 12/2022 |
| CN | 115444544 | A | 12/2022 |
| CN | 115444549 | A | 12/2022 |
| CN | 115461007 | A | 12/2022 |
| CN | 115500932 | A | 12/2022 |
| CN | 115500933 | A | 12/2022 |
| CN | 217938222 | U | 12/2022 |
| CN | 115300752 | B | 1/2023 |
| CN | 115590606 | A | 1/2023 |
| CN | 115590608 | A | 1/2023 |
| CN | 115666700 | A | 1/2023 |
| CN | 107343784 | B | 2/2023 |
| CN | 115697221 | A | 2/2023 |
| CN | 115702823 | A | 2/2023 |
| CN | 115768346 | A | 3/2023 |
| CN | 115844515 | A | 3/2023 |
| CN | 115886978 | A | 4/2023 |
| CN | 115942915 | A | 4/2023 |
| CN | 115969577 | A | 4/2023 |
| CN | 115990309 | A | 4/2023 |
| CN | 110520067 | B | 5/2023 |
| CN | 111225627 | B | 5/2023 |
| CN | 116115323 | A | 5/2023 |
| CN | 116115325 | A | 5/2023 |
| CN | 116135163 | A | 5/2023 |
| CN | 116137804 | A | 5/2023 |
| CN | 116157084 | A | 5/2023 |
| CN | 116157174 | A | 5/2023 |
| CN | 116158839 | A | 5/2023 |
| CN | 116172689 | A | 5/2023 |
| CN | 219022916 | U | 5/2023 |
| CN | 106419897 | B | 6/2023 |
| CN | 111065350 | B | 6/2023 |
| CN | 116234511 | A | 6/2023 |
| CN | 116236272 | A | 6/2023 |
| CN | 116250914 | A | 6/2023 |
| CN | 116327346 | A | 6/2023 |
| CN | 219230098 | U | 6/2023 |
| CN | 219680753 | U | 9/2023 |
| CN | 109259854 | B | 10/2023 |
| CN | 111657866 | B | 10/2023 |
| CN | 117122328 | A | 11/2023 |
| CN | 117355271 | A | 1/2024 |
| CN | 117357121 | A | 1/2024 |
| CN | 117396150 | A | 1/2024 |
| CN | 117426866 | A | 1/2024 |
| CN | 114209331 | B | 2/2024 |
| CN | 117582284 | A | 2/2024 |
| CN | 117597080 | A | 2/2024 |
| CN | 111836579 | B | 3/2024 |
| CN | 112704546 | B | 3/2024 |
| CN | 117897110 | A | 4/2024 |
| CN | 117942483 | A | 4/2024 |
| CN | 117958829 | A | 5/2024 |
| CN | 115379873 | B | 6/2024 |
| CN | 118203407 | A | 6/2024 |
| CN | 118234442 | A | 6/2024 |
| CN | 118251185 | A | 6/2024 |
| CN | 111096749 | B | 7/2024 |
| CN | 113164127 | B | 7/2024 |
| CN | 118267076 | A | 7/2024 |
| CN | 118267082 | A | 7/2024 |
| CN | 118384409 | A | 7/2024 |
| CN | 113993572 | B | 8/2024 |
| CN | 114040724 | B | 8/2024 |
| CN | 111683581 | B | 9/2024 |
| CN | 112040861 | B | 9/2024 |
| CN | 118697365 | A | 9/2024 |
| CN | 118715039 | A | 9/2024 |
| CN | 111683614 | B | 10/2024 |
| CN | 112121284 | B | 11/2024 |
| CN | 118891015 | A | 11/2024 |
| CN | 118900667 | A | 11/2024 |
| CN | 113226443 | B | 12/2024 |
| CN | 115381549 | B | 12/2024 |
| CN | 111374755 | B | 1/2025 |
| CN | 111436928 | B | 1/2025 |
| CN | 111918606 | B | 1/2025 |
| CN | 112969498 | B | 1/2025 |
| CN | 113543728 | B | 1/2025 |
| CN | 113693716 | B | 1/2025 |
| CN | 114340535 | B | 1/2025 |
| CN | 115284943 | B | 1/2025 |
| CN | 115338627 | B | 1/2025 |
| CN | 116116820 | B | 1/2025 |
| CN | 119255743 | A | 1/2025 |
| CN | 119255832 | A | 1/2025 |
| CN | 119384251 | A | 1/2025 |
| CN | 111691972 | B | 2/2025 |
| CN | 112278762 | B | 2/2025 |
| CN | 112520267 | B | 2/2025 |
| CN | 112674068 | B | 2/2025 |
| CN | 115252012 | B | 2/2025 |
| CN | 119385661 | A | 2/2025 |
| CN | 119455229 | A | 2/2025 |
| CN | 119497601 | A | 2/2025 |
| CN | 119522063 | A | 2/2025 |
| CN | 111462635 | B | 3/2025 |
| CN | 111994108 | B | 3/2025 |
| CN | 112207374 | B | 3/2025 |
| CN | 119584942 | A | 3/2025 |
| CN | 119607406 | A | 3/2025 |
| CN | 119612420 | A | 3/2025 |
| CN | 119730804 | A | 3/2025 |
| CN | 112040860 | B | 5/2025 |

(56) References Cited

FOREIGN PATENT DOCUMENTS

| | | | |
|---|---|---|---|
| CN | 114423344 | B | 5/2025 |
| CN | 120035406 | A | 5/2025 |
| CN | 120051250 | A | 5/2025 |
| CN | 111374756 | B | 6/2025 |
| CN | 112135576 | B | 6/2025 |
| CN | 115461007 | B | 6/2025 |
| DE | 202021104266 | U1 | 8/2021 |
| EP | 0889744 | B1 | 1/2004 |
| EP | 1254641 | B1 | 11/2008 |
| EP | 1690564 | B1 | 4/2009 |
| EP | 1723981 | B1 | 8/2010 |
| EP | 2135634 | B1 | 10/2011 |
| EP | 2018203 | B1 | 6/2012 |
| EP | 1814450 | B1 | 1/2013 |
| EP | 2269532 | B1 | 3/2013 |
| EP | 2664295 | A1 | 11/2013 |
| EP | 2604306 | B1 | 1/2014 |
| EP | 2732843 | A1 | 5/2014 |
| EP | 2747680 | A2 | 7/2014 |
| EP | 2752153 | A1 | 7/2014 |
| EP | 2907462 | A1 | 8/2015 |
| EP | 2915555 | A1 | 9/2015 |
| EP | 1968679 | B1 | 9/2016 |
| EP | 2241279 | B1 | 9/2016 |
| EP | 3111871 | A1 | 1/2017 |
| EP | 3111872 | A1 | 1/2017 |
| EP | 2796103 | B1 | 2/2017 |
| EP | 3222209 | A1 | 9/2017 |
| EP | 2792322 | B1 | 10/2017 |
| EP | 2792323 | B1 | 10/2017 |
| EP | 3115076 | A4 | 10/2017 |
| EP | 3117863 | A4 | 10/2017 |
| EP | 3030182 | B1 | 1/2018 |
| EP | 3287092 | A1 | 2/2018 |
| EP | 3111871 | B1 | 3/2018 |
| EP | 3111872 | B1 | 4/2018 |
| EP | 3057488 | B1 | 5/2018 |
| EP | 2848226 | B1 | 7/2018 |
| EP | 3345540 | A1 | 7/2018 |
| EP | 3363397 | A1 | 8/2018 |
| EP | 3391928 | A1 | 10/2018 |
| EP | 3122276 | B1 | 11/2018 |
| EP | 3398549 | A1 | 11/2018 |
| EP | 3403571 | A1 | 11/2018 |
| EP | 1759668 | B1 | 12/2018 |
| EP | 3020352 | B1 | 12/2018 |
| EP | 3037122 | B1 | 12/2018 |
| EP | 2234537 | B1 | 1/2019 |
| EP | 2569040 | B1 | 2/2019 |
| EP | 3023052 | B1 | 3/2019 |
| EP | 3073908 | B1 | 4/2019 |
| EP | 3466363 | A1 | 4/2019 |
| EP | 2550989 | B1 | 6/2019 |
| EP | 3512589 | A1 | 7/2019 |
| EP | 3512590 | A1 | 7/2019 |
| EP | 3527125 | A1 | 8/2019 |
| EP | 3531903 | A1 | 9/2019 |
| EP | 3581229 | A1 | 12/2019 |
| EP | 3434218 | B1 | 2/2020 |
| EP | 2908723 | B1 | 3/2020 |
| EP | 3335658 | B1 | 4/2020 |
| EP | 3073907 | B1 | 6/2020 |
| EP | 3673851 | A1 | 7/2020 |
| EP | 3114987 | B1 | 8/2020 |
| EP | 3178516 | B1 | 9/2020 |
| EP | 3708104 | A1 | 9/2020 |
| EP | 3711662 | A1 | 9/2020 |
| EP | 3721796 | A1 | 10/2020 |
| EP | 3733103 | A1 | 11/2020 |
| EP | 3738508 | A1 | 11/2020 |
| EP | 3738509 | A1 | 11/2020 |
| EP | 3340916 | B1 | 12/2020 |
| EP | 3579908 | B1 | 12/2020 |
| EP | 3749174 | A1 | 12/2020 |
| EP | 3749191 | A1 | 12/2020 |
| EP | 3749192 | A1 | 12/2020 |
| EP | 3749195 | A1 | 12/2020 |
| EP | 3750475 | A1 | 12/2020 |
| EP | 3768185 | A1 | 1/2021 |
| EP | 2155301 | B1 | 4/2021 |
| EP | 3432820 | B1 | 4/2021 |
| EP | 3476331 | B1 | 5/2021 |
| EP | 3579758 | B1 | 5/2021 |
| EP | 2809254 | B1 | 6/2021 |
| EP | 3508245 | B1 | 7/2021 |
| EP | 3858277 | A1 | 8/2021 |
| EP | 3892221 | A1 | 10/2021 |
| EP | 3902461 | A1 | 11/2021 |
| EP | 3915477 | A1 | 12/2021 |
| EP | 3915501 | A1 | 12/2021 |
| EP | 3919014 | A1 | 12/2021 |
| EP | 3932343 | A4 | 1/2022 |
| EP | 3791820 | B9 | 4/2022 |
| EP | 3986520 | A1 | 4/2022 |
| EP | 3991680 | A2 | 5/2022 |
| EP | 3995079 | A1 | 5/2022 |
| EP | 4000506 | A1 | 5/2022 |
| EP | 3153124 | B1 | 7/2022 |
| EP | 3860447 | A4 | 7/2022 |
| EP | 4025112 | A1 | 7/2022 |
| EP | 4031007 | A1 | 7/2022 |
| EP | 4031044 | A2 | 7/2022 |
| EP | 4039215 | A1 | 8/2022 |
| EP | 4041112 | A1 | 8/2022 |
| EP | 3363397 | B1 | 9/2022 |
| EP | 3673944 | B1 | 9/2022 |
| EP | 3915501 | B1 | 9/2022 |
| EP | 3949848 | A4 | 9/2022 |
| EP | 4076193 | A1 | 10/2022 |
| EP | 4078255 | A1 | 10/2022 |
| EP | 4079365 | A2 | 10/2022 |
| EP | 3609414 | B1 | 11/2022 |
| EP | 4088676 | A1 | 11/2022 |
| EP | 4091565 | A1 | 11/2022 |
| EP | 4091569 | A1 | 11/2022 |
| EP | 4093274 | A1 | 11/2022 |
| EP | 4096545 | A1 | 12/2022 |
| EP | 4101372 | A1 | 12/2022 |
| EP | 4101375 | A1 | 12/2022 |
| EP | 4101383 | A1 | 12/2022 |
| EP | 4104763 | A1 | 12/2022 |
| EP | 4106625 | A1 | 12/2022 |
| EP | 4106853 | A2 | 12/2022 |
| EP | 2844193 | B1 | 1/2023 |
| EP | 3100696 | B1 | 1/2023 |
| EP | 3166524 | B1 | 1/2023 |
| EP | 3946123 | A4 | 1/2023 |
| EP | 4115832 | A1 | 1/2023 |
| EP | 4115833 | A1 | 1/2023 |
| EP | 4115936 | A1 | 1/2023 |
| EP | 4120963 | A1 | 1/2023 |
| EP | 4122414 | A1 | 1/2023 |
| EP | 4134032 | A1 | 2/2023 |
| EP | 4137080 | A1 | 2/2023 |
| EP | 3115076 | B1 | 3/2023 |
| EP | 3658054 | B1 | 3/2023 |
| EP | 4144397 | A1 | 3/2023 |
| EP | 4157420 | A1 | 4/2023 |
| EP | 4159124 | A1 | 4/2023 |
| EP | 4164519 | A1 | 4/2023 |
| EP | 4167886 | A1 | 4/2023 |
| EP | 4179991 | A1 | 5/2023 |
| EP | 4181810 | A1 | 5/2023 |
| EP | 4185224 | A1 | 5/2023 |
| EP | 4185225 | A1 | 5/2023 |
| EP | 2803329 | B1 | 6/2023 |
| EP | 3015064 | B1 | 6/2023 |
| EP | 3141183 | B1 | 6/2023 |
| EP | 3398549 | B1 | 6/2023 |
| EP | 3768185 | B1 | 6/2023 |
| EP | 4190232 | A1 | 6/2023 |
| EP | 4190257 | A2 | 6/2023 |
| EP | 4193947 | A1 | 6/2023 |
| EP | 4201356 | A2 | 6/2023 |

(56) References Cited

FOREIGN PATENT DOCUMENTS

| | | | |
|---|---|---|---|
| EP | 4201357 | A1 | 6/2023 |
| EP | 4205684 | A1 | 7/2023 |
| EP | 4218579 | A1 | 8/2023 |
| EP | 2816966 | B1 | 10/2023 |
| EP | 3113671 | B1 | 10/2023 |
| EP | 3681427 | B1 | 10/2023 |
| EP | 3738509 | B1 | 10/2023 |
| EP | 3749195 | B1 | 10/2023 |
| EP | 4257068 | A1 | 10/2023 |
| EP | 4265210 | A1 | 10/2023 |
| EP | 3209234 | B1 | 11/2023 |
| EP | 3527125 | B1 | 11/2023 |
| EP | 3721796 | B1 | 11/2023 |
| EP | 3731747 | B1 | 11/2023 |
| EP | 3998935 | B1 | 11/2023 |
| EP | 4091547 | B1 | 11/2023 |
| EP | 4233699 | A3 | 11/2023 |
| EP | 4268746 | A1 | 11/2023 |
| EP | 4272631 | A2 | 11/2023 |
| EP | 4285850 | A1 | 12/2023 |
| EP | 4291123 | A1 | 12/2023 |
| EP | 3192442 | B1 | 1/2024 |
| EP | 3892221 | B1 | 1/2024 |
| EP | 4298995 | A2 | 1/2024 |
| EP | 4309606 | A1 | 1/2024 |
| EP | 3738508 | B1 | 2/2024 |
| EP | 4324388 | A1 | 2/2024 |
| EP | 4327768 | A1 | 2/2024 |
| EP | 4137051 | B1 | 3/2024 |
| EP | 4340762 | A1 | 3/2024 |
| EP | 3124069 | B1 | 4/2024 |
| EP | 4003234 | B9 | 4/2024 |
| EP | 4159124 | B1 | 4/2024 |
| EP | 3943139 | B1 | 5/2024 |
| EP | 4167886 | B1 | 5/2024 |
| EP | 4342406 | A3 | 5/2024 |
| EP | 4353171 | A3 | 5/2024 |
| EP | 4360572 | A1 | 5/2024 |
| EP | 4362831 | A1 | 5/2024 |
| EP | 4364680 | A2 | 5/2024 |
| EP | 4364765 | A2 | 5/2024 |
| EP | 4368133 | A1 | 5/2024 |
| EP | 4370064 | A1 | 5/2024 |
| EP | 4370187 | A1 | 5/2024 |
| EP | 3498156 | B1 | 6/2024 |
| EP | 4044947 | B1 | 6/2024 |
| EP | 4344722 | A3 | 6/2024 |
| EP | 4376745 | A1 | 6/2024 |
| EP | 4378408 | A2 | 6/2024 |
| EP | 4378515 | A2 | 6/2024 |
| EP | 4382060 | A1 | 6/2024 |
| EP | 4382061 | A1 | 6/2024 |
| EP | 4385414 | A1 | 6/2024 |
| EP | 4385440 | A1 | 6/2024 |
| EP | 4385441 | A1 | 6/2024 |
| EP | 4389036 | A1 | 6/2024 |
| EP | 3573559 | B1 | 7/2024 |
| EP | 3673851 | | 7/2024 |
| EP | 3834728 | | 7/2024 |
| EP | 4181810 | A4 | 7/2024 |
| EP | 4272631 | A3 | 7/2024 |
| EP | 4364680 | A3 | 7/2024 |
| EP | 4392113 | A1 | 7/2024 |
| EP | 4393377 | A1 | 7/2024 |
| EP | 4393425 | A1 | 7/2024 |
| EP | 4393426 | A2 | 7/2024 |
| EP | 4393426 | A3 | 7/2024 |
| EP | 4393433 | A1 | 7/2024 |
| EP | 4393434 | A1 | 7/2024 |
| EP | 4393436 | A1 | 7/2024 |
| EP | 4393437 | A1 | 7/2024 |
| EP | 4397264 | A1 | 7/2024 |
| EP | 3603493 | B1 | 8/2024 |
| EP | 3998975 | B1 | 8/2024 |
| EP | 4205685 | B1 | 8/2024 |
| EP | 4378408 | A3 | 8/2024 |
| EP | 4378515 | A3 | 8/2024 |
| EP | 4410185 | A1 | 8/2024 |
| EP | 4412547 | A1 | 8/2024 |
| EP | 4412549 | A1 | 8/2024 |
| EP | 4417112 | A2 | 8/2024 |
| EP | 3629964 | B1 | 9/2024 |
| EP | 4427666 | A2 | 9/2024 |
| EP | 4433133 | A1 | 9/2024 |
| EP | 4433141 | A1 | 9/2024 |
| EP | 3184035 | B1 | 10/2024 |
| EP | 4091569 | | 10/2024 |
| EP | 4218579 | B1 | 10/2024 |
| EP | 4444195 | A1 | 10/2024 |
| EP | 4452069 | A1 | 10/2024 |
| EP | 3915477 | B1 | 11/2024 |
| EP | 4193947 | B1 | 11/2024 |
| EP | 4311484 | B1 | 11/2024 |
| EP | 4417112 | A3 | 11/2024 |
| EP | 4427666 | A3 | 11/2024 |
| EP | 3860447 | B1 | 12/2024 |
| EP | 4101372 | B1 | 12/2024 |
| EP | 4215138 | B1 | 12/2024 |
| EP | 4437989 | A3 | 12/2024 |
| EP | 4477171 | A2 | 12/2024 |
| EP | 3737453 | B1 | 1/2025 |
| EP | 3760152 | B1 | 1/2025 |
| EP | 3957968 | B1 | 1/2025 |
| EP | 4031044 | | 1/2025 |
| EP | 4311485 | | 1/2025 |
| EP | 4458292 | A3 | 1/2025 |
| EP | 4482412 | A1 | 1/2025 |
| EP | 4482413 | A1 | 1/2025 |
| EP | 4482564 | A2 | 1/2025 |
| EP | 4489634 | A1 | 1/2025 |
| EP | 4496546 | A1 | 1/2025 |
| EP | 2915555 | B1 | 2/2025 |
| EP | 4031007 | B1 | 2/2025 |
| EP | 4153526 | B1 | 2/2025 |
| EP | 4480435 | A3 | 2/2025 |
| EP | 4498955 | A1 | 2/2025 |
| EP | 4501285 | A1 | 2/2025 |
| EP | 4504085 | A1 | 2/2025 |
| EP | 4507562 | A1 | 2/2025 |
| EP | 4507582 | A1 | 2/2025 |
| EP | 4507607 | A1 | 2/2025 |
| EP | 4511098 | A2 | 2/2025 |
| EP | 4483828 | A3 | 3/2025 |
| EP | 4514256 | A1 | 3/2025 |
| EP | 4514274 | A1 | 3/2025 |
| EP | 4387547 | B1 | 5/2025 |
| EP | 4370187 | B1 | 6/2025 |
| EP | 4555953 | A3 | 6/2025 |
| IL | 246415 | B | 12/2019 |
| IN | 201614021431 | A | 12/2016 |
| IN | 201614021432 | A | 12/2016 |
| IN | 201614021450 | A | 12/2016 |
| JP | 4545384 | B2 | 7/2010 |
| JP | 4887810 | B2 | 2/2012 |
| JP | 4940332 | B2 | 3/2012 |
| JP | 2012055602 | A | 3/2012 |
| JP | 2012200509 | A | 10/2012 |
| JP | 5154031 | B2 | 2/2013 |
| JP | 5193190 | B2 | 5/2013 |
| JP | 5372314 | B2 | 12/2013 |
| JP | 2014014713 | A | 1/2014 |
| JP | 5550150 | B2 | 5/2014 |
| JP | 5762697 | B2 | 6/2015 |
| JP | 5856712 | B2 | 2/2016 |
| JP | 5908270 | B2 | 4/2016 |
| JP | 5944331 | B2 | 7/2016 |
| JP | 6050522 | B2 | 12/2016 |
| JP | 6059737 | B2 | 12/2016 |
| JP | 2017012750 | A | 1/2017 |
| JP | 2017012755 | A | 1/2017 |
| JP | 2017038919 | A | 2/2017 |
| JP | 2017051211 | A | 3/2017 |
| JP | 2017104552 | A | 6/2017 |
| JP | 6246742 | B2 | 12/2017 |

(56) References Cited

FOREIGN PATENT DOCUMENTS

| | | | |
|---|---|---|---|
| JP | 6342524 | B2 | 6/2018 |
| JP | 6434495 | B2 | 12/2018 |
| JP | 6445509 | B2 | 12/2018 |
| JP | 6445742 | B1 | 12/2018 |
| JP | 6466114 | B2 | 2/2019 |
| JP | 6479005 | B2 | 2/2019 |
| JP | 6515084 | B2 | 5/2019 |
| JP | 6528010 | B1 | 6/2019 |
| JP | 6655655 | B2 | 2/2020 |
| JP | 2020108766 | A | 7/2020 |
| JP | 6746734 | B2 | 8/2020 |
| JP | 6776021 | B2 | 10/2020 |
| JP | 6776025 | B2 | 10/2020 |
| JP | 6786275 | B2 | 11/2020 |
| JP | 6821812 | B2 | 1/2021 |
| JP | 2021007772 | A | 1/2021 |
| JP | 2021501011 | A | 1/2021 |
| JP | 6843502 | B2 | 3/2021 |
| JP | 2021069921 | A | 5/2021 |
| JP | 6894004 | B2 | 6/2021 |
| JP | 6920312 | B2 | 8/2021 |
| JP | 6926306 | B2 | 8/2021 |
| JP | 6932484 | B2 | 8/2021 |
| JP | 6936872 | B2 | 9/2021 |
| JP | 2021523755 | A | 9/2021 |
| JP | 6980386 | B2 | 12/2021 |
| JP | 2022020838 | A | 2/2022 |
| JP | 2022063862 | A | 4/2022 |
| JP | 7101228 | B2 | 7/2022 |
| JP | 7102558 | B2 | 7/2022 |
| JP | 7106301 | B2 | 7/2022 |
| JP | 7135202 | B2 | 9/2022 |
| JP | 2022540496 | A | 9/2022 |
| JP | 2022159146 | A | 10/2022 |
| JP | 2022176157 | A | 11/2022 |
| JP | 2022546719 | A | 11/2022 |
| JP | 2022548944 | A | 11/2022 |
| JP | 2022177819 | A | 12/2022 |
| JP | 2022179432 | A | 12/2022 |
| JP | 2022187485 | A | 12/2022 |
| JP | 2022187486 | A | 12/2022 |
| JP | 2022188763 | A | 12/2022 |
| JP | 2023002720 | A | 1/2023 |
| JP | 2023010544 | A | 1/2023 |
| JP | 2023501756 | A | 1/2023 |
| JP | 7220242 | B2 | 2/2023 |
| JP | 7230168 | B2 | 2/2023 |
| JP | 2023024395 | A | 2/2023 |
| JP | 2023026388 | A | 2/2023 |
| JP | 2023506505 | A | 2/2023 |
| JP | 2023507412 | A | 2/2023 |
| JP | 7242665 | B2 | 3/2023 |
| JP | 7242816 | B2 | 3/2023 |
| JP | 7246319 | B2 | 3/2023 |
| JP | 2023027023 | A | 3/2023 |
| JP | 2023027202 | A | 3/2023 |
| JP | 2023033335 | A | 3/2023 |
| JP | 7256621 | B2 | 4/2023 |
| JP | 7262919 | B2 | 4/2023 |
| JP | 2023515798 | A | 4/2023 |
| JP | 2023517284 | A | 4/2023 |
| JP | 7275333 | B2 | 5/2023 |
| JP | 7282759 | B2 | 5/2023 |
| JP | 2023074000 | A | 5/2023 |
| JP | 2023519039 | A | 5/2023 |
| JP | 7292822 | B2 | 6/2023 |
| JP | 2023526907 | A | 6/2023 |
| JP | 2023139173 | A | 10/2023 |
| JP | 7391562 | B2 | 11/2023 |
| JP | 7394766 | B2 | 11/2023 |
| JP | 2023160789 | A | 11/2023 |
| JP | 2023164368 | A | 11/2023 |
| JP | 7400050 | B2 | 12/2023 |
| JP | 2023177311 | A | 12/2023 |
| JP | 7423550 | B2 | 1/2024 |
| JP | 2024012693 | A | 1/2024 |
| JP | 2024014846 | A | 2/2024 |
| JP | 2024028213 | A | 3/2024 |
| JP | 2024031886 | A | 3/2024 |
| JP | 7465944 | B2 | 4/2024 |
| JP | 2024045056 | A | 4/2024 |
| JP | 2024046636 | A | 4/2024 |
| JP | 2024059810 | A | 5/2024 |
| JP | 2024060605 | A | 5/2024 |
| JP | 2024070850 | A | 5/2024 |
| JP | 7493935 | B2 | 6/2024 |
| JP | 7499702 | B2 | 6/2024 |
| JP | 7512156 | B2 | 7/2024 |
| JP | 7514764 | B2 | 7/2024 |
| JP | 7515637 | B2 | 7/2024 |
| JP | 7516185 | B2 | 7/2024 |
| JP | 7523073 | B2 | 7/2024 |
| JP | 7523074 | B2 | 7/2024 |
| JP | 2024094302 | A | 7/2024 |
| JP | 2024095616 | A | 7/2024 |
| JP | 2024096081 | A | 7/2024 |
| JP | 2024096084 | A | 7/2024 |
| JP | 2024096089 | A | 7/2024 |
| JP | 2024096092 | A | 7/2024 |
| JP | 2024096095 | A | 7/2024 |
| JP | 2024096097 | A | 7/2024 |
| JP | 2024528078 | A | 7/2024 |
| JP | 7517994 | B2 | 8/2024 |
| JP | 7520967 | B2 | 8/2024 |
| JP | 7530317 | B2 | 8/2024 |
| JP | 7532506 | B2 | 8/2024 |
| JP | 7535097 | B2 | 8/2024 |
| JP | 2024103761 | A | 8/2024 |
| JP | 7539974 | B2 | 9/2024 |
| JP | 7551326 | B2 | 9/2024 |
| JP | 2024121015 | A | 9/2024 |
| JP | 2024125304 | A | 9/2024 |
| JP | 7566503 | B2 | 10/2024 |
| JP | 2024536350 | A | 10/2024 |
| JP | 2024536352 | A | 10/2024 |
| JP | 2024537099 | A | 10/2024 |
| JP | 7574276 | B2 | 11/2024 |
| JP | 7577739 | B2 | 11/2024 |
| JP | 7587597 | B2 | 11/2024 |
| JP | 2024156696 | A | 11/2024 |
| JP | 2024543437 | A | 11/2024 |
| JP | 7592480 | B2 | 12/2024 |
| JP | 2024544543 | A | 12/2024 |
| JP | 7617073 | B2 | 1/2025 |
| JP | 7617103 | B2 | 1/2025 |
| JP | 2025013792 | A | 1/2025 |
| JP | 7628563 | B2 | 2/2025 |
| JP | 7633185 | B2 | 2/2025 |
| JP | 7637671 | B2 | 2/2025 |
| JP | 7639079 | B2 | 2/2025 |
| JP | 2025023950 | A | 2/2025 |
| JP | 2025026734 | A | 2/2025 |
| JP | 2025026852 | A | 2/2025 |
| JP | 2025027101 | A | 2/2025 |
| JP | 7635238 | B2 | 3/2025 |
| JP | 7640580 | B2 | 3/2025 |
| JP | 7641330 | B2 | 3/2025 |
| JP | 2025028941 | A | 3/2025 |
| JP | 2025036543 | A | 3/2025 |
| JP | 2025036738 | A | 3/2025 |
| JP | 2025507449 | A | 3/2025 |
| JP | 7646980 | B2 | 4/2025 |
| JP | 7647478 | B2 | 4/2025 |
| JP | 7654796 | B2 | 4/2025 |
| JP | 7662472 | B2 | 4/2025 |
| JP | 7662473 | B2 | 4/2025 |
| JP | 2025509157 | A | 4/2025 |
| JP | 2025511803 | A | 4/2025 |
| JP | 7686646 | B2 | 6/2025 |
| RU | 2016124794 | A | 12/2017 |
| RU | 2016124801 | A | 12/2017 |
| RU | 2016125763 | A | 1/2018 |
| WO | 9843530 | A1 | 10/1998 |
| WO | 0168178 | A1 | 9/2001 |

(56) References Cited

FOREIGN PATENT DOCUMENTS

WO 2008091197 A1 7/2008
WO 2014113612 A1 7/2014
WO 2015057521 A1 4/2015
WO 2015095577 A1 6/2015
WO 2015130824 A1 9/2015
WO 2016001015 A1 1/2016
WO 2017098198 A1 6/2017
WO 2018053148 A1 3/2018
WO 2018053164 A1 3/2018
WO 2018106496 A1 6/2018
WO 2018136741 A1 7/2018
WO 2019195439 A1 10/2019
WO 2019226640 A1 11/2019
WO 2020113137 A1 6/2020
WO 2021053482 A1 3/2021
WO 2021053648 A1 3/2021
WO 2021061198 A1 4/2021
WO 2021242852 A1 12/2021
WO 2022038546 A1 2/2022
WO 2022148153 A1 7/2022
WO 2022180046 A1 9/2022
WO 2022214870 A1 10/2022
WO 2022246011 A1 11/2022
WO 2022251429 A1 12/2022
WO 2023275848 A1 1/2023
WO 2023278577 A1 1/2023
WO 2023280822 A1 1/2023
WO 2023287289 A1 1/2023
WO 2023007324 A1 2/2023
WO 2023009569 A1 2/2023
WO 2023018741 A1 2/2023
WO 2023028531 A1 3/2023
WO 2023059507 A1 4/2023
WO 2023059509 A1 4/2023
WO 2023086778 A1 5/2023
WO 2023086865 A1 5/2023
WO 2023105322 A1 6/2023
WO 2023122183 A1 6/2023
WO 2023164001 A1 8/2023
WO 2023192858 A1 10/2023
WO 2023196810 A1 10/2023
WO 2024072900 A1 4/2024
WO 2024077888 A1 4/2024
WO 2024107185 A1 5/2024
WO 2024110813 A1 5/2024
WO 2024155619 A1 7/2024
WO 2024159881 A1 8/2024
WO 2024167632 A1 8/2024
WO 2024172915 A1 8/2024
WO 2024177974 A1 8/2024

* cited by examiner

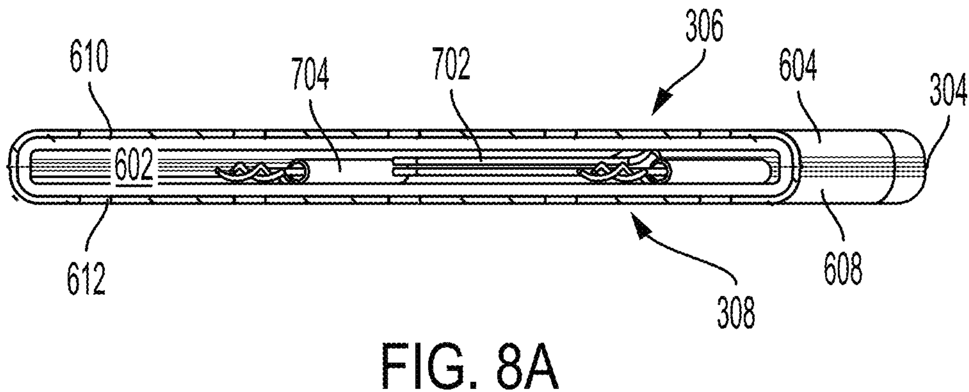
FIG. 8A
306
610
704
604
304
602
612
308
608
FIG. 8B
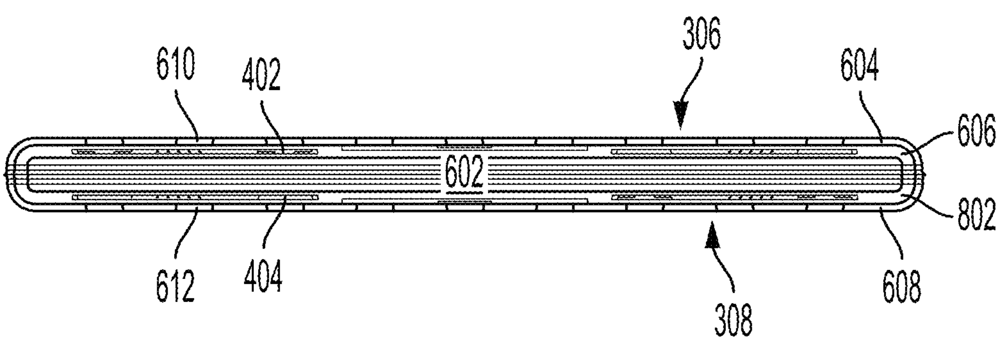
FIG. 8C 204
1008
1010
1004
1002
1012

304
602
1010
1004
1004
1012
1002
1002
1014
906
204

204
208
1006
1006
1004
1002
1002
1012
1008
1014
1010
906
1004

HIGH DENSITY FLAT BALLOON CATHETER

CROSS REFERENCES TO RELATED APPLICATIONS

The present application claims the benefit under 35 USC § 119 (e) of U.S. Provisional Application Nos. 63/685,139 filed Aug. 20, 2024 and 63/558,318 filed Feb. 27, 2024; and is a Continuation-in-Part of PCT Application No. PCT/US2023/086380 filed Dec. 29, 2023, which claims priority to U.S. Provisional Patent Application Nos. 63/603,451 filed Nov. 28, 2023 and 63/448,625 filed Feb. 27, 2023; the full disclosures which are incorporated herein by reference in their entirety for all purposes.

BACKGROUND

Electrophysiological (EP) catheters can be configured for use in diagnosing and/or treating cardiac arrythmias. A cardiac arrythmia may be manifest in one or more observable medical conditions including, for example, an irregular heart rate, loss of synchronous atrioventricular contractions, and inadequate flow of blood through a chamber of the heart, which can lead to a variety of symptomatic and/or asymptomatic ailments and even death. Electrical activity of a patient's heart can be measured and assessed to determine whether the patient's heart exhibits a pathological electrical condition(s) associated with the occurrence of the cardiac arrythmia. Following diagnosis of the pathological electrical condition(s), a suitable treatment(s) can be used to selectively alter the patient's heart tissue to reduce or eliminate the pathological electrical condition to reduce or eliminate occurrence of the cardiac arrythmia. The treatment can include, for example, radio frequency (RF) ablation, pulsed field ablation (PFA), cryoablation, laser ablation, chemical ablation, high-intensity focused ultrasound ablation, microwave ablation, and/or other ablation treatments.

BRIEF SUMMARY

The present invention generally relates to expandable catheters for use in electrophysiology, and more specifically to high-density balloon catheters for use in diagnosing and/or treating cardiac arrhythmias. A substantially flat balloon member (e.g., having a two-sided balloon structure) according to embodiments described herein includes internal flex circuits and electrodes exposed through one or both sides of the balloon member. The designs of the present invention allow for smaller surface area electrodes, tighter spacing between the electrodes, and a multitude of shape configurations (e.g., flat shape, football shape, convex, concave, etc.) and electrode arrangements (e.g., offset horizontal and/or vertical rows) which in turn provides improved diagnostic measurements while reducing manufacturing costs. For example, the electrodes may be patterned in offset rows for more equally spaced electrode groupings. Associated algorithms do not have to compensate for timing delays leading to more accurate mapping and sensing capabilities. Designs including two-sided balloon members enable improved determination of tissue or blood contact at the electrode interface, thereby reducing or eliminating far field effects. In some aspects of the present invention, the balloon member includes a flexible structural element to further buttress the rigidity and stiffness of the balloon structures and to prevent kinking.

In various embodiments, a catheter includes an elongate catheter shaft comprising a proximal end and a distal end. The elongate catheter shaft defines a longitudinal axis. The catheter includes an expandable assembly having a first delivery configuration and a second deployed configuration. The expandable assembly includes a balloon member having a top surface, a bottom surface, and an interior cavity. Each of the top surface and the bottom surface includes an outer facing layer and an inner facing layer. The expandable assembly includes a top flexible framework disposed between the outer facing layer and the inner facing layer of the top surface of the balloon member and a bottom flexible framework disposed between the outer facing layer and the inner facing layer of the bottom surface of the balloon member. In some embodiments, a first plurality of electrodes are patterned onto the top flexible framework and a second plurality of electrodes are patterned onto the bottom flexible framework. The first plurality of electrodes are aligned with the second plurality of electrodes. A plurality of conductive traces are disposed on each of the flexible frameworks. Each of the plurality of conductive traces are electrically coupled with a respective one of the first plurality of electrodes and the second plurality of electrodes. The expandable assembly includes a flexible structural element disposed within the interior cavity. According to various embodiments of the present disclosure, conductive materials may include electrodes and conductors. Further, various conductive materials may include metals such as copper, gold, silver, platinum, iridium (IV) oxide (IrOx), titanium nickel (TiNi), or the like, and alloys thereof. Conductive materials may also include polymers such as poly (3,4-ethylenedioxythiophene) (PEDOT), modified PEDOT, or the like.

In at least some embodiments, the flexible structural element comprises a nitinol wire looped element extending along the longitudinal axis of the elongate catheter shaft for providing rigidity to the balloon member and to prevent kinking of the balloon member when the balloon member contacts tissue. The nitinol wire looped element is disposed between the top flexible framework and the bottom flexible framework.

According to some aspects, the balloon member includes a plurality of apertures on the outer facing layer of the top surface and the outer facing layer of the bottom surface of the balloon member. The plurality of apertures expose the respective first plurality of electrodes and the second plurality of electrodes. A diameter of the plurality of apertures is the same size or smaller than a diameter of the respective first and second plurality of electrodes. The plurality of apertures have a diameter in a range from 0.25 mm to 3 mm and the respective first and second plurality of electrodes have a diameter in a range from 0.25 mm to 3 mm. The first and second plurality of electrodes are flush (e.g., spot electrodes), recessed, or raised with respect to the outer facing layer of the top surface and the bottom surface of the balloon member. For example, the electrodes may be raised above the outer facing layer of the top surface of the balloon member for increasing tissue contact between the electrodes and a tissue of interest (e.g., cardiac tissue).

In various aspects, the elongate catheter shaft includes an inflation lumen. The inflation lumen may be oval shaped in some embodiments. The balloon member in the first delivery configuration is uninflated and in the second deployed configuration is inflated via a liquid or a gas delivered through the oval inflation lumen. The expandable assembly has an intermediate configuration between the first configuration and the second configuration, where, in the intermediate configuration, the balloon member is unconstrained from an introducer sheath and uninflated. In some aspects, the balloon member has a flat, concave, or convex shape in the second deployed configuration. For example, the balloon member is substantially flat when in the deployed configuration. In other aspects, the balloon member extends outward in a central portion of the balloon member to form a "football" shape (e.g., a convex shape).

In at least some aspects, each of the first plurality of electrodes and the second plurality of electrodes are arranged in horizontal rows relative to the longitudinal axis of the elongate catheter shaft. The horizontal rows are offset such that each electrode in each row is offset from a respective electrode in an adjacent row. For example, each electrode in each row is equally spaced from adjacent electrodes in the same row and adjacent rows. A center-to-center distance between each of the electrodes in the first plurality of electrodes and the second plurality of electrodes is 2.5 mm. In some aspects, a center-to-center distance between each of the electrodes in the first plurality of electrodes and the second plurality of electrodes is in a range from 1 mm to 4 mm. In other aspects, each of the first plurality of electrodes and the second plurality of electrodes are arranged in vertical rows parallel to the longitudinal axis of the elongate catheter shaft and the vertical rows are offset such that each electrode in each row is offset from a respective electrode in an adjacent row. The horizontal and/or vertical offset is 60°, in some aspects. In various aspects, the horizontal and/or vertical offset is in a range from 22.5° to 60°.

In various aspects, each of the first plurality of electrodes and the second plurality of electrodes are configured for independent sensing for diagnostic mapping or energy delivery for treating cardia arrhythmias. For example, the first plurality of electrodes may be configured to sense tissue of interest (e.g., cardiac tissue) while the second plurality of electrodes may be configured to sense other tissue or fluid (e.g., blood). In various embodiments, the first and/or second plurality of electrodes may be independently activated and/or deactivated during use. Individual electrodes in the first and/or second plurality of electrodes may be independently activated and/or deactivated during use.

According to various aspects, each of the electrodes in the first plurality of electrodes and the second plurality of electrodes are grouped into cliques of three or more electrodes defining a two-dimensional shape. For example, the cliques of electrodes are configured in an equilateral triangular shape where each clique includes at least three electrodes. The cliques of electrodes are configured to sample electrical characteristics of contacted tissue in at least two substantially transverse directions. In various embodiments, electrode cliques including 4 or more electrodes spanning three dimensions (e.g., utilizing one or more electrodes on each side of the balloon) enable a more complete and unobstructed assessment of tissue electrical characteristics in all three dimensions. There may be sizable electrogram contributions both transverse and normal (e.g., perpendicular) to a cardiac surface. In some embodiments, a plurality of through-holes may be used to further enhance the sampling of the electrical characteristics of the tissue.

For any embodiments described herein, any number of electrodes may form a clique in various shapes. In one exemplary embodiment, each of the electrodes in the first plurality of electrodes and the second plurality of electrodes are grouped into cliques of four or more electrodes defining a three-dimensional shape. The cliques of four or more electrodes may be configured in a tetrahedral shape, such as tri-rectangular tetrahedron. For example, cliques of six electrodes may be configured in a triangular prism (e.g., an equilateral triangular prism, a regular and irregular triangular prism, a right triangular prism, an oblique triangular prism, etc.). It should be appreciated that any of the cliques described herein may be formed from electrodes located on different sides (e.g., a top side and a bottom side) of the balloon catheter. For example, an electrode disposed on a top surface may form a clique of three or more electrodes or four or more electrodes with electrodes disposed on a bottom surface of a balloon catheter as described herein.

According to various embodiments, the catheter is a conductive balloon catheter. A conductive balloon catheter may include a conductive material configured to dissipate electrical energy into tissue during an ablation procedure. In at least some embodiments, the conductive material surfaces of the conductive balloon catheter may be configured to disperse electrical energy to deliver PFA therapy. The conductive balloon may further include a non-conductive masking material covering a portion of the conductive material and defining at least one window of exposed conductive material on a surface of the balloon. For example, the conductive balloon catheter may include conductive elastomers, for example, doped with carbon or other conduct materials. The balloon conductivity may be similar to that of blood. In some embodiments, the balloon cavity may be inflated with a conductive material such as saline, half-normal saline, or a mixture of contrast agent and saline. Accordingly, the conductive balloon embodiment enables three-dimensional electrogram characterization and electrical impedance navigation without requiring additional magnetic sensors.

In some aspects, the catheter includes at least one magnetic position sensor disposed along a distal portion of the catheter shaft. The catheter may also include one or more magnetic position sensors disposed on the top flexible framework and/or on the bottom flexible framework on a distal portion of the expandable assembly.

In one embodiment, a catheter includes an elongate catheter shaft including a proximal end and a distal end. The catheter shaft defines a longitudinal axis. The catheter includes an expandable assembly having a first delivery configuration and a second deployed configuration. The expandable assembly includes a balloon member having a substantially flat and/or planar shape in the second deployed configuration and includes a top surface and a bottom surface. The balloon member includes a first plurality of electrodes extending within and exposed through the top surface and/or the top surface of the balloon member and a second plurality of electrodes extending within and exposed through the bottom surface of the balloon member. Each of the first plurality of electrodes and the second plurality of electrodes are arranged in horizontal rows relative to the longitudinal axis of the elongate catheter shaft. The horizontal rows are offset such that each electrode in each row is offset from a respective electrode in an adjacent row.

According to some embodiments, each electrode in each row is equally spaced from adjacent electrodes in the same row and adjacent rows. In one exemplary embodiment, each electrode in the first plurality of electrodes has a diameter of 0.25 mm such that the edge-to-edge spacing is 0.25 mm and the center-to-center spacing is 0.5 mm. In another embodiment, the center-to-center distance between each of the electrodes in the first plurality of electrodes and the second plurality of electrodes is 1.0 mm. In yet another embodiment, a center-to-center distance between each of the electrodes in the first plurality of electrodes and the second plurality of electrodes may be 1.5 mm. According to other embodiments, a center-to-center distance between each of the electrodes in the first plurality of electrodes and the second plurality of electrodes may be 2.0 mm. In yet another embodiment, a center-to-center distance between each of the electrodes in the first plurality of electrodes and the second plurality of electrodes may be 2.5 mm. In other embodiments, a center-to-center distance between each of the electrodes in the first plurality of electrodes and the second plurality of electrodes may be 3.0 mm. In some aspects, a center-to-center distance between each of the electrodes in the first plurality of electrodes and the second plurality of electrodes is in a range from 0.5 mm to 3 mm. In other aspects, each of the first plurality of electrodes and the second plurality of electrodes are additionally arranged in vertical rows parallel to the longitudinal axis of the elongate catheter shaft and the vertical rows are offset such that each electrode in each row is offset from a respective electrode in an adjacent row. The horizontal and/or vertical offset is 60°, in some aspects. In various aspects, the horizontal and/or vertical offset is in a range from 22.5° to 60°.

In at least some embodiments, the expandable assembly includes a flexible structural element disposed within an interior cavity of the balloon member. The flexible structural element comprises a nitinol wire looped element extending along the longitudinal axis of the elongate catheter shaft for providing rigidity to the balloon member and to prevent kinking of the balloon member when the balloon member contacts tissue. The nitinol wire looped element is disposed between the top flexible framework and the bottom flexible framework further buttresses the integrity of the catheter. It will be appreciated that the balloon member when inflated provides sufficient rigidity and/or stiffness when the balloon member contacts tissue.

In some aspects, the expandable assembly includes a balloon member having a top surface, a bottom surface, and an interior cavity. Each of the top surface and the bottom surface includes an outer facing layer and an inner facing layer. The expandable assembly includes a top flexible framework disposed between the outer facing layer and the inner facing layer of the top surface of the balloon member and a bottom flexible framework disposed between the outer facing layer and the inner facing layer of the bottom surface of the balloon member. In some embodiments, a first plurality of electrodes are patterned onto the top flexible framework and a second plurality of electrodes are patterned onto the bottom flexible framework. The first plurality of electrodes are aligned with the second plurality of electrodes. A plurality of conductive traces are disposed on each of the flexible frameworks. Each of the plurality of conductive traces are electrically coupled with a respective one of the first plurality of electrodes and the second plurality of electrodes.

In some aspects, the balloon member itself incorporates conductive traces disposed onto the outer facing layer of the top surface and/or the outer facing layer of the bottom surface without the need to incorporate any separate flexible framework (e.g., polyimide flex circuit). The balloon member may comprise a variety of materials including thermoplastic polyurethanes (TPUs), thermoplastic elastomers (TPEs), polyamides including nylons or Pebax, ethylene vinyl acetates (EVAs), polyvinylidene fluoride (PVDF), polyvinyl chloride (PVC), silicon, silicone, and/or composite material combinations thereof. During manufacture, the electrodes and corresponding conductive traces are built (e.g., disposed) onto the outer layer of the top surface and/or the outer layer of the bottom surface of the balloon member as described in further detail below.

In other embodiments, a catheter comprises a flexible silicone pad structure having a substantially flat and/or planar shape. The catheter includes an elongate catheter shaft comprising a proximal end and a distal end. The catheter shaft defines a longitudinal axis. The catheter includes an expandable assembly having a first delivery configuration and a second deployed configuration. The expandable assembly includes a top surface, a bottom surface, and a flexible framework disposed between the top surface and the bottom surface. A plurality of electrodes are patterned onto the flexible framework. The plurality of electrodes are arranged in horizontal rows relative to the longitudinal axis of the elongate catheter shaft and the horizontal rows are offset such that each electrode in each row is offset from a respective electrode in an adjacent row. A plurality of conductive traces are disposed on the flexible framework coupled with the plurality of electrodes and a flexible structural element is disposed within the expandable assembly. In some aspects, the silicone pad structure includes an interior cavity between the top surface and the bottom surface, and the flexible structural element is disposed within the interior cavity. In other aspects, the silicone pad structure does not have an interior cavity when the components are placed in a mold and the silicone is injection molded to form the silicone pad structure. In other embodiments, a laminate layer may be disposed within the interior cavity. Additional structures may be provided within the interior cavity for setting the diameter of the assembly. For example, in one embodiment, the catheter comprises a polyimide layer disposed between the top surface and the bottom surface. Alternative materials that may be provided in the internal cavity for setting the diameter of the assembly may include relatively soft materials such as polymers to relatively hard materials such as metals in the form of thin structural members.

In yet another embodiment, a catheter having a substantially flat and/or planar shape may only incorporate electrodes disposed on one of a top surface or a bottom surface. The catheter includes an elongate catheter shaft comprising a proximal end and a distal end. The catheter shaft defines a longitudinal axis. The catheter includes an expandable assembly having a first delivery configuration and a second deployed configuration. The expandable assembly includes a balloon member having a top surface, a bottom surface, and an interior cavity. In this embodiment, one of the top surface and the bottom surface includes an outer facing layer and an inner facing layer and a flexible framework disposed between the outer facing layer and the inner facing layer. A plurality of electrodes are patterned onto the flexible framework and a plurality of conductive traces are disposed on the flexible framework. Each of the plurality of conductive traces are electrically coupled with the plurality of electrodes. The balloon member includes a flexible structural element disposed within the interior cavity.

In one embodiment, a pulsed field ablation catheter includes an elongate catheter shaft including a proximal end and a distal end. The elongate catheter shaft defines a longitudinal axis. The catheter includes an expandable assembly including a balloon member having a top surface, a bottom surface, and an interior cavity. Each of the top surface and the bottom surface includes an outer facing layer and an inner facing layer. The catheter further includes a top flexible framework disposed between the outer facing layer and the inner facing layer of the top surface of the balloon member, a bottom flexible framework disposed between the outer facing layer and the inner facing layer of the bottom surface of the balloon member, a first plurality of electrodes patterned onto the top flexible framework, and a second plurality of electrodes patterned onto the bottom flexible framework. The first plurality of electrodes are aligned with the second plurality of electrodes. The one or more electrodes of the first plurality of electrodes and/or the second plurality of electrodes are configured to deliver pulsed field ablation energy to a tissue. The catheter further includes a plurality of conductive traces disposed on each of the flexible frameworks and each of the plurality of conductive traces is electrically coupled with a respective one of the first plurality of electrodes and the second plurality of electrodes. The catheter further includes a flexible structural element disposed within the interior cavity.

According to some embodiments, the one or more electrodes may be configured to be activated in unison in a ganged configuration for pulsed field ablation. The ganged configuration may include an outer grouping of electrodes of a first polarity and an inner grouping of electrodes of a second polarity. The one or more electrodes may be configured to be activated independent from one another in an un-ganged configuration for pulsed field ablation. The one of more electrodes may include a center grouping of electrodes for pulsed field ablation. According to some embodiments, each of the first plurality of electrodes and the second plurality of electrodes are further advantageously configured for independent sensing.

In some embodiments, the balloon member is a conductive balloon member comprising conductive material configured to dissipate electrical energy into tissue during pulsed field ablation. The one or more electrodes and the conductive balloon may be configured to be activated in unison in a ganged configuration. The one of more electrodes and the conductive balloon may be configured to be activated independent from one another in an un-ganged configuration.

In at least some embodiments, a plurality of through-holes may extend between the top surface and the bottom surface and through the interior cavity of the balloon member. The catheter may further include where the flexible structural element comprises a nitinol wire looped element extending along the longitudinal axis of the elongate catheter shaft. The nitinol wire looped element may be disposed between the top flexible framework and the bottom flexible framework.

According to various embodiments, the expandable assembly may further include a first delivery configuration and a second deployed configuration. The balloon member may have a flat, concave, or convex shape in the second deployed configuration. The expandable assembly may also have an intermediate configuration between the first delivery configuration and the second deployed configuration, wherein, in the intermediate configuration, the balloon member is unconstrained from an introducer sheath and uninflated.

In some embodiments, each of the first plurality of electrodes and the second plurality of electrodes are arranged in horizontal rows relative to the longitudinal axis of the elongate catheter shaft and the horizontal rows are offset such that each electrode in each row is offset from a respective electrode in an adjacent row. Each of the first plurality of electrodes and the second plurality of electrodes may be arranged in vertical rows parallel to the longitudinal axis of the elongate catheter shaft and the vertical rows are offset such that each electrode in each row is offset from a respective electrode in an adjacent row. The offset may be 60°. The offset may be in a range from 22.5° to 60°. Each electrode in each row may be equally spaced from adjacent electrodes in the same row and adjacent rows.

In various embodiments, the balloon member includes a plurality of apertures on the outer facing layer of the top surface and the bottom surface of the balloon member configured to expose the respective first plurality of electrodes and the second plurality of electrodes, wherein a diameter of the plurality of apertures is the same size or smaller than a diameter of the respective first and second plurality of electrodes. The plurality of apertures may have a diameter in a range from 0.25 mm to 3 mm and the respective first and second plurality of electrodes have a diameter in a range from 0.25 mm to 3 mm. The first and second plurality of electrodes may be flush or raised with respect to the outer facing layer of the top surface and the bottom surface of the balloon member. Further, the elongate catheter shaft may include an oval inflation lumen coupled to the interior cavity of the balloon member and the balloon member in the first delivery configuration is uninflated and in the second deployed configuration is inflated via a liquid or a gas delivered through the oval inflation lumen.

In some embodiments, each of the first plurality of electrodes and the second plurality of electrodes are configured for independent sensing. Each of the electrodes in the first plurality of electrodes and the second plurality of electrodes may be grouped into cliques of three or more electrodes defining a two-dimensional shape. Each of the first plurality of electrodes and the second plurality of electrodes may be grouped into cliques of three or more electrodes where the cliques of three or more electrodes are configured to sample electrical characteristics of contacted tissue in at least two substantially transverse directions. Each of the electrodes in the first plurality of electrodes and the second plurality of electrodes may be grouped into cliques of four or more electrodes defining a three-dimensional shape. The cliques of four or more electrodes may be configured in an equilateral tetrahedral shape. The cliques of four or more electrodes may be configured in a tri-rectangular tetrahedron.

According to various embodiments, a center-to-center distance between each of the electrodes in the first plurality of electrodes and the second plurality of electrodes is 2.5 mm. A center-to-center distance between each of the electrodes in the first plurality of electrodes and the second plurality of electrodes may be in a range from 1 mm to 4 mm. The catheter may further include at least one magnetic position sensor disposed along a distal portion of the elongate catheter shaft. The balloon member may be a linear shape, a hoop shape, or a circular shape. The balloon member may include thermoplastic polyurethanes (TPUs), thermoplastic elastomers (TPEs), polyamides including nylons or Pebax, ethylene vinyl acetates (EVAs), polyvinylidene fluoride (PVDF), polyvinyl chloride (PVC), silicon, silicone, and/or composite materials thereof.

According to another embodiment, that may include any of the embodiments herein, a catheter includes an elongate catheter shaft comprising a proximal end and a distal end. The elongate catheter shaft defines a longitudinal axis. The catheter may further include an expandable assembly having a first delivery configuration and a second deployed configuration and include a balloon member having a top surface, a bottom surface, and an interior cavity, a first plurality of electrodes extending within and exposed through the top surface of the balloon member, a second plurality of electrodes extending within and exposed through the bottom surface of the balloon member, and a plurality of through-holes extending between the top surface and the bottom surface and through the interior cavity of the balloon member.

According to another embodiment, that may include any of the embodiments herein, a catheter includes an elongate catheter shaft comprising a proximal end and a distal end. The elongate catheter shaft defines a longitudinal axis. The catheter may further include an expandable assembly having a conductive balloon member having a top surface, a bottom surface, and an interior cavity. Each of the top surface and the bottom surface include conductive material configured to dissipate electrical energy into tissue during an ablation procedure. The balloon member further includes a top flexible framework disposed below the top surface and the bottom surface of the balloon member. The balloon member further includes a bottom flexible framework disposed between the top surface and the bottom surface of the balloon member opposite the top flexible framework. The balloon member further includes a first plurality of electrodes patterned onto the top flexible framework and a second plurality of electrodes patterned onto the bottom flexible framework where the first plurality of electrodes are aligned with the second plurality of electrodes. The balloon member further includes a plurality of conductive traces disposed on each of the flexible frameworks, each of the plurality of conductive traces electrically coupled with a respective one of the first plurality of electrodes and the second plurality of electrodes.

According to various embodiments, the catheter may include one or more electrodes of the first plurality of electrodes and/or the second plurality of electrodes are configured to deliver pulsed field energy to a tissue. The one or more electrodes and the conductive balloon may be configured to be activated in unison in a ganged configuration. The one of more electrodes and the conductive balloon may be configured to be activated independent from one another in an un-ganged configuration. The one or more electrodes may be configured to be activated in unison in a ganged configuration for pulsed field ablation.

According to one embodiment, a catheter includes an elongate catheter shaft comprising a proximal end and a distal end. The elongate catheter shaft defines a longitudinal axis. The catheter includes an expandable assembly having a first delivery configuration and a second deployed configuration. The expandable assembly further includes a balloon member having a substantially flat shape in the second deployed configuration and comprising a top surface and a bottom surface, a first plurality of electrodes extending within and exposed through the top surface of the balloon member, and a second plurality of electrodes extending within and exposed through the bottom surface of the balloon member. Each of the first plurality of electrodes and the second plurality of electrodes are arranged in horizontal rows relative to the longitudinal axis of the elongate catheter shaft and the horizontal rows are offset such that each electrode in each row is offset from a respective electrode in an adjacent row. One or more electrodes of the first plurality of electrodes and/or the second plurality of electrodes are configured to deliver pulsed field ablation energy to a tissue.

According to one embodiment, a catheter includes an elongate catheter shaft comprising a proximal end and a distal end. The elongate catheter shaft defines a longitudinal axis. The catheter includes an expandable assembly having a first delivery configuration and a second deployed configuration. The expandable assembly further includes a balloon member having a substantially flat shape in the second deployed configuration and comprising a top surface, a bottom surface, and an interior cavity. The balloon member includes a first plurality of electrodes extending within and exposed through the top surface of the balloon member, a second plurality of electrodes extending within and exposed through the bottom surface of the balloon member. Each of the first plurality of electrodes and the second plurality of electrodes are arranged in horizontal rows relative to the longitudinal axis of the elongate catheter shaft. The horizontal rows are offset such that each electrode in each row is offset from a respective electrode in an adjacent row. The catheter further includes a plurality of through-holes extending between the top surface and the bottom surface and through the interior cavity of the balloon member.

According to one embodiment, a catheter includes an elongate catheter shaft comprising a proximal end and a distal end. The elongate catheter shaft defines a longitudinal axis. The catheter includes an expandable assembly having a first delivery configuration and a second deployed configuration. The expandable assembly further includes a balloon member having a substantially flat shape in the second deployed configuration and comprising a top surface a bottom surface, and an interior cavity. Each of the top surface and the bottom surface comprising conductive material configured to dissipate electrical energy into tissue during an ablation procedure. The balloon member further includes a first plurality of electrodes extending within and exposed through the top surface of the balloon member and a second plurality of electrodes extending within and exposed through the bottom surface of the balloon member. Each of the first plurality of electrodes and the second plurality of electrodes are arranged in horizontal rows relative to the longitudinal axis of the elongate catheter shaft. The horizontal rows are offset such that each electrode in each row is offset from a respective electrode in an adjacent row.

The above presents a simplified summary of some embodiments of the invention to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented below.

Where the term "planar" or, similarly, "plane" or "coplanar" is used herein, it should be understood to refer to a topological plane. In other words, a "plane" may not be "flat" in a Cartesian coordinate system, but rather represents a two-dimensional distribution that is planar in a topological sense. Likewise, where the term "linear" is used herein, it should be understood to refer to a topological line. In other words, a "linear" may not be "straight line" in a Cartesian coordinate system, but rather represents a one-dimensional distribution that is linear in a topological sense.

BRIEF DESCRIPTION OF THE DRAWINGS

FIGS. 8A, 8B, and 8C depict various cross-sectional views of an expandable electrode assembly, in accordance with embodiments of the present disclosure.

DETAILED DESCRIPTION OF THE INVENTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
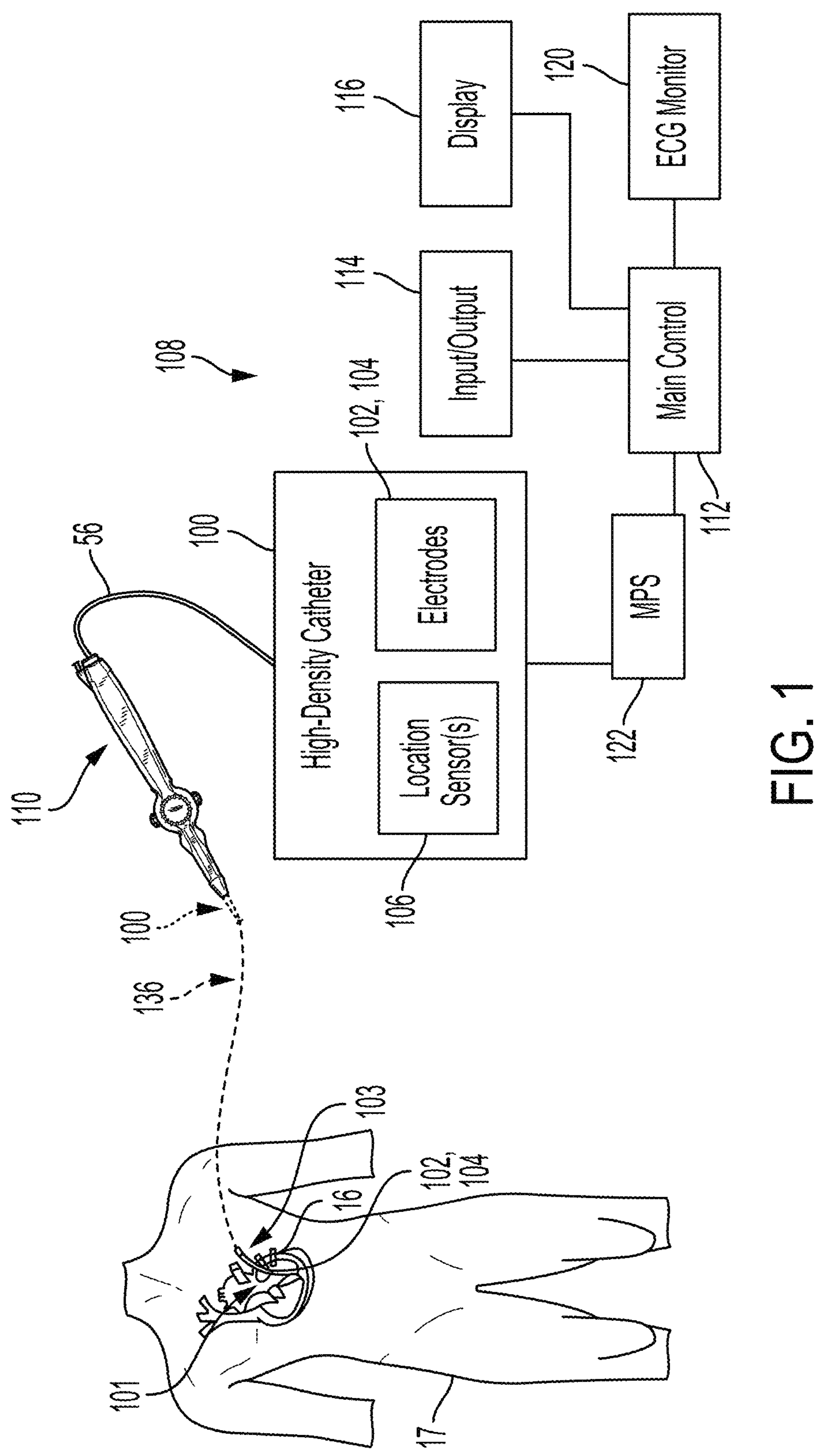
FIG. 1 illustrates an example medical device localization system that can be employed in conjunction with the expandable catheter, in accordance with embodiments of the present disclosure.

As shown in FIG. 1, the electrode assembly 101 of the high-density catheter 100 is configured to be conformable to a tissue (e.g., cardiac tissue) to interface the electrodes 102 with the tissue. In many embodiments, the electrode assembly 101 has a suitable flexibility to accommodate suitable flexure of the electrode assembly 101 in response to suitable interface forces between the electrode assembly 101 and the tissue. For example, the electrode assembly 101 comprises a flexible balloon member (e.g., an expandable electrode assembly 202) which is configured to be conformable to the tissue to interface the electrodes 102 with the tissue. The balloon member may comprise a variety of biocompatible materials including thermoplastic polyurethanes (TPUs), thermoplastic elastomers (TPEs), polyamides including nylons or Pebax, ethylene vinyl acetates (EVAs), polyvinylidene fluoride (PVDF), polyvinyl chloride (PVC), silicon, silicone, and/or composite materials thereof. In preferred aspects, the balloon material comprises Pebax.

Figure 2:
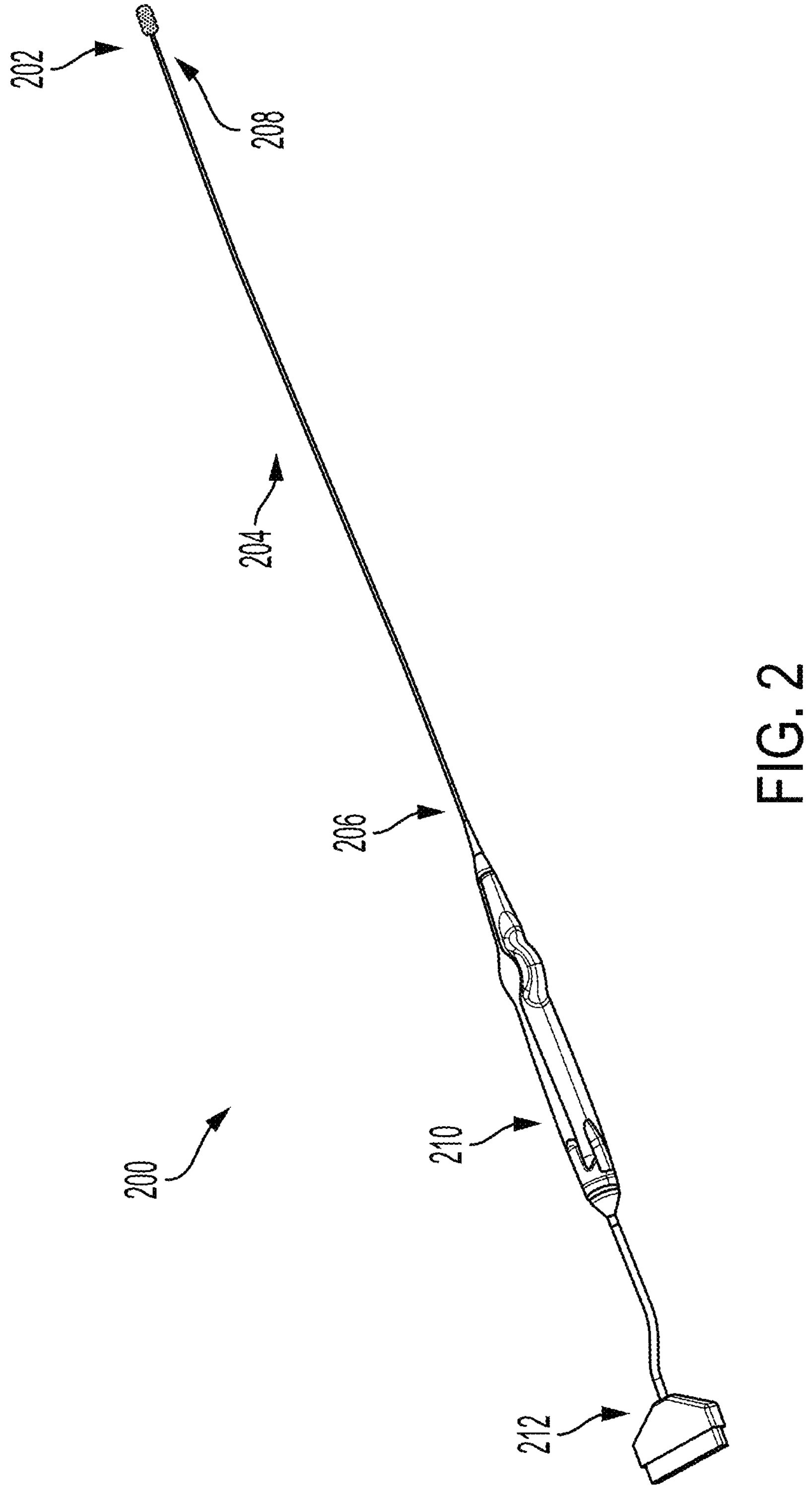
FIG. 2 illustrates an example catheter, in accordance with embodiments of the present disclosure.

The configuration of the electrode assembly 101 discussed herein facilitates insertion of the electrode assembly 101 using a handle 110 of the catheter, deployment of the electrode assembly 101 within the heart 16, and withdrawal of the electrode assembly 101 from the patient 17 by accommodating relative movement between an undeployed configuration and a deployed configuration. In particular, an expandable electrode assembly 202 (as shown in FIG. 2) serves to avoid inducing high localized strains that may result absent the relative movement accommodation. For example, upon entering a target chamber of the heart 16, the electrodes 102 extending within the surface of the expandable electrode assembly 202 interface with the tissue as the expandable electrode assembly 202 is expanded (e.g., inflated), collapsed (e.g., deflated), advanced, or retracted to receive signals. The signals can be transmitted via the connector 56 to a system for analyzing the signal e.g., to determine localization. In some embodiments, the electrode assembly 101 can be inserted within the heart 16 through an introducer or a delivery catheter.

The high-density catheter 100 can be used in conjunction with any suitable medical device localization system, such as those referenced and/or described herein. For example, the high-density catheter 100 can be used in conjunction with the catheter localization systems and methods described in U.S. Patent Pub. No. 2020/0138334 A1 entitled "Method for Medical Device Localization based on Magnetic and Impedance Sensors", the entire disclosure of which is incorporated herein by reference.

FIG. 1 also illustrates a diagrammatic view of a medical device localization system 108 that can be used in conjunction with the high-density catheter 100. The system 108 includes a main electronic control unit 112 (e.g., a processor) having various input/output mechanisms 114, a display 116, an electrocardiogram (ECG) monitor 120, a localization system, such as a medical positioning system 122, and the high-density catheter 100. As described herein, in some embodiments the high-density catheter 100 includes the electrodes 102, 104 and one or more of the location sensors 106 (which are in some embodiments configured as magnetic location sensors).

The input/output mechanisms 114 may include conventional apparatus for interfacing with a computer-based control unit including, for example, one or more of a keyboard, a mouse, a tablet, a foot pedal, a switch, and/or the like. The display 116 may also comprise conventional apparatus, such as a computer monitor.

The ECG monitor 120 is configured to continuously detect an electrical timing signal of the heart organ through the use of a plurality of ECG electrodes (not shown), which may be externally affixed to the outside of a patient's body. The timing signal generally corresponds to a particular phase of the cardiac cycle, among other things. Generally, the ECG signal(s) may be used by the control unit 112 for ECG synchronized play-back of a previously captured sequence of images (cine loop). The ECG monitor 120 and ECG electrodes may both include conventional components.

The medical positioning system 122 is configured to serve as the localization system and therefore to determine position (localization) data with respect to the one or more location sensors 106 and/or the electrodes 103 and output a respective location reading.

The impedance based medical positioning system 122 determines locations of the electrodes 103 based on capturing and processing signals received from the electrodes 103 and external electrode patches while the electrodes 103 are disposed in a controlled electrical field (e.g., potential field) generated by the electrode patches, for example. The electrical impedance-based medical positioning system ('MPS system') system 122 may include various visualization, mapping and navigation components as known in the art, including, for example, an EnSite™ X EP System commercially available from Abbott Laboratories or as seen generally by reference to U.S. Pat. No. 7,263,397 entitled "Method and Apparatus for Catheter Navigation and Location and Mapping in the Heart" owned by the common assignee of the present invention, and incorporated by reference in its entirety.

The high-density catheter 100 can be used in conjunction with any suitable catheter system, such as those referenced and/or described herein. For example, the high-density catheter 100 can be used to generate an electrophysiological map of electrical activity within a patient's heart to diagnose cardiac arrythmias. It should be understood that the high-density catheter 100 may be used for any other suitable diagnostic and/or therapeutic purposes. Accordingly, the high-density catheter 100 can be configured to perform ablation procedures, cardiac mapping, electrophysiological (EP) studies and other diagnostic and/or therapeutic procedures. For example, ablation procedures may include RF ablation, PFA, cryoablation, laser ablation, chemical ablation, high-intensity focused ultrasound ablation, microwave ablation, and/or other ablation treatments. Embodiments are not limited to any one type of catheter or catheter-based system or procedure.

Applications

Ablation therapy may be used to treat various conditions afflicting the human anatomy. One such condition in which ablation therapy may be used is the treatment of cardiac arrhythmias. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmias can create a variety of dangerous conditions including loss of synchronous atrioventricular contractions and stasis of blood flow. It is believed that the primary cause of atrial arrhythmia is stray electrical signals within the left or right atrium of the heart. The ablation catheter imparts ablative energy (e.g., radiofrequency energy, PFA, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

Various embodiments as described throughout the present disclosure may be used in PFA applications. PFA utilizes a controlled electric field to ablate and scar tissue through a process called irreversible electroporation (IRE). PFA provides for higher tissue specificity than conventional ablation and its requirements for power (current 10's of Amps and voltage levels from 100's to 1000's) are higher/larger than the power requirements of high-density mapping catheters. PFA may be delivered from multiple electrodes either on an expandable structure or from a distal portion of a linear catheter. Ablation electrodes may be individually electrically coupled to an electroporation generator, such as a power supply via suitable electrical wire or other suitable electrical conductors extending through the catheter shaft and may be configured to be selectively energized (e.g., by a power supply and/or computer system) with opposite polarities to generate a potential and corresponding electric field therebetween, for PFA therapy. In some embodiments, a distal-most tip electrode may be energized with an opposite polarity to at least one other of a plurality of electrodes, to generate a potential and corresponding electric field therebetween, for PFA therapy. Exemplary embodiments of PFA applications, methods, systems, etc., may include those described with respect to International Publication No. WO 2023/192858 A1 entitled "MULTI-ELECTRODE ASSEMBLY FOR HYBRID MAPPING AND ABLATION CATHETER"; and International Publication No. WO 2023/196810 A1 entitled "HYBRID MAPPING AND PULSED FIELD ABLATION CATHETER"; the full disclosures of which are incorporated herein by reference in their entirety for all purposes.

Electroporation is a non-thermal ablation technique that involves applying strong electric fields that induce pore formation in the cellular membrane. The electric field may be induced by applying a relatively short duration pulse which may last, for example, from a nanosecond to several milliseconds. Such a pulse may be repeated to form a pulse train. When such an electric field is applied to tissue in an in vivo setting, the cells in the tissue are subjected to a trans-membrane potential, which opens the pores on the cell wall. Electroporation may be reversible (i.e., the temporally opened pores will reseal) or irreversible (i.e., the pores will remain open), causing cellular destruction. For example, in the field of gene therapy, reversible electroporation is used to transfect high molecular weight therapeutic vectors into the cells. In other therapeutic applications, a suitably configured pulse train alone may be used to cause cell destruction, for instance by causing irreversible electroporation.

In some embodiments, the high-density catheter 100 is used for electroporation-induced primary necrosis therapy, which refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field (i.e., pulsed field ablation (PFA)) in the form of short-duration pulses (e.g., 0.1 to 20 ms duration) between closely spaced electrodes capable of delivering an electric field strength of about 0.1 to 1.0 kV/cm.

The high-density catheter 100 can be used to selectively alter the patient's heart tissue to reduce or eliminate the pathological electrical condition to reduce or eliminate occurrence of the cardiac arrythmia. The high-density catheter 100 can configured for use in performing any suitable treatment, such as, but not limited to, radio frequency (RF) ablation, pulsed field ablation (PFA), cryoablation, laser ablation, chemical ablation, high-intensity focused ultrasound ablation, microwave ablation, and/or other ablation treatments. In one embodiment, electrodes 102, 104 may be disposed on opposing surfaces of the high-density catheter 100 and electrodes 102 and/or electrodes 104 are configured to ablate from electrode to electrode on the high-density catheter 100.

Figure 3:
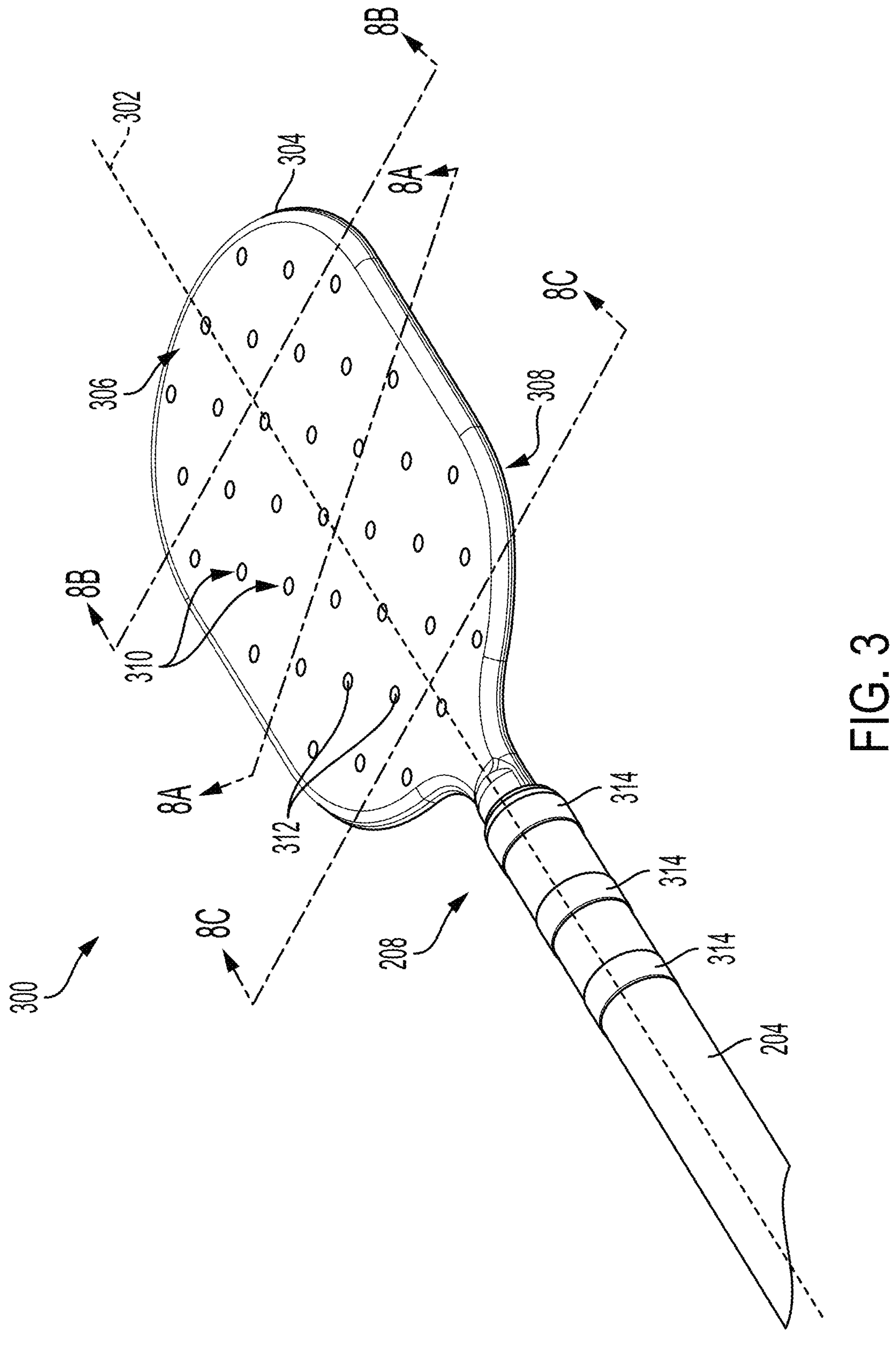
FIG. 3 depicts a perspective view of an expandable electrode assembly, in accordance with embodiments of the present disclosure.

For example, and in some embodiments, the high-density catheter 100 may be configured as a bipolar electrode assembly for use in bipolar-based electroporation therapy. Specifically, the electrodes 102, 104 of the high-density catheter 100 can be individually electrically coupled to an electroporation generator (e.g., via suitable electrical wire or other suitable electrical conductors extending through the catheter shaft 136) and are configured to be selectively energized by the electroporation generator with opposite polarities to generate a potential and corresponding electric field therebetween, for PFA therapy. That is, one of electrodes 102, 104 can be configured to function as a cathode, and another of the electrodes 102, 104 can be configured to function as an anode. Any suitable combination of the electrodes 102, 104 of the electrode assembly 101 can be used as anodes and cathodes. For example, all the electrodes 102 on one of the electrode portions can be employed as a cathode and all the electrodes 104 on an adjacent one of the electrode portions can be employed as an anode. As another example, every other of the electrodes 102 along one of the electrode portions can be employed as a cathode and the other of the electrodes 104 along the electrode portion can be employed as an anode. The electrodes 102, 104 may be any suitable electroporation electrodes. For example, the electrodes 102, 104 may comprise spot electrodes as illustrated in FIG. 3. The electrodes 102, 104 may have any other suitable shape or configuration. The shape, size, and/or configuration of the electrodes 102, 104 may impact various parameters of the applied electroporation therapy. For example, increasing the surface area of one or both of the electrodes 102, 104 may reduce the applied voltage needed to cause the same level of tissue destruction. Moreover, although each of the electrodes 102, 104 is illustrated as a single electrode, either or both of the electrodes 102, 104 may be alternatively embodied as two or more discrete electrodes. According to any of the embodiments of the present disclosure, the catheter as described may include one or more electrodes that are configured to deliver pulsed field energy to a tissue. Furthermore, according to various embodiments, one or more electrodes are selectively energizable to affect PFA therapy. During application of PFA, the size of the electric field generated, and accordingly, the lesion size, may be based at least in part on the electrode geometry (e.g., electrode shape, length, interelectrode distances, etc.).

FIG. 2 illustrates an exemplary catheter device 200, in accordance with embodiments of the present disclosure. FIG. 2 shows an expandable electrode assembly 202 having a balloon member and a plurality of electrodes extending within and exposed through the top surface and/or bottom surface of the expandable electrode assembly 202, according to embodiments discussed herein. FIG. 2 shows the expandable electrode assembly 202 coupled to an elongate catheter shaft 204 having a proximal end 206 and a distal end 208. In particular, the expandable electrode assembly 202 is coupled to the distal end 208 of the elongate catheter shaft 204. At the proximal end 206 of the elongate catheter shaft 204, handle 210 and connector 212 are configured to electronically couple and physically couple the expandable electrode assembly 202 to a mapping and/or therapeutic system for sensing and/or energy delivery (e.g., such as system 108 described in detail with reference to FIG. 1).

FIG. 3 illustrates an example of an expandable electrode assembly 300, in accordance with embodiments of the present disclosure. The expandable electrode assembly 300 may be coupled to the distal end 208 of the elongate catheter shaft 204, as described in detail above. In various embodiments, the elongate catheter shaft 204 defines a longitudinal axis 302. The elongate catheter shaft 204 further includes one or more shaft electrodes 314. Shaft electrodes 314 may be for impedance localization as described above with respect to the electrical impedance-based medical positioning system 122 in FIG. 1.

The expandable electrode assembly 300 includes a balloon member 304 having a first delivery configuration, and a second deployed configuration. In the delivery configuration, the balloon member 304 is collapsed, rolled, or folded into a working lumen of an introducer sheath. The balloon member 304 may additionally have folding lines, ribs, pleats, and/or divot points to help align and facilitate delivery of the expandable electrode assembly 300 within the introducer sheath. In the first delivery configuration, the balloon member 304 is advanced out of the introducer sheath (and/or the introducer sheath is retracted proximally) in a deflated state. In the second deployed configuration, the balloon member 304 is expanded via inflation with a gas, liquid, or combination thereof. The balloon member 304 may be coupled to an inflation lumen (described in detail below with reference to FIG. 10C) extending within the elongate catheter shaft and inflated via saline, oxygen, nitrogen dioxide (e.g., which can also be used for cryotherapy ablation of tissue), air, or any combination thereof. Such fluids are delivered through the inflation lumen to inflate and/or expand an interior cavity of the balloon member 304. Following the procedure, the inflation gas and/or liquid may be aspirated, suctioned, and/or exhausted out through the inflation lumen and/or catheter shaft lumen and the balloon member 304 may be collapsed and retracted back into the introducer sheath such that the balloon member 304 together with the introducer sheath can be removed from the patient. In various embodiments, the inflation lumen is an oval inflation lumen as discussed in more detail below.

The balloon member 304 may be a compliant balloon member or a non-compliant balloon, depending on the material(s) of the balloon member 304 and/or the level of inflation provided through the inflation lumen for transitioning the balloon member 304 from the first delivery/deflated configuration to the second deployed/inflated configuration. In a preferred embodiment, the balloon member 304 material is Pebax. The balloon member 304 material may be processed as discussed below so as to allow the balloon member 304 to elastically deform from a collapsed, first delivery configuration within the introducer sheath to an intermediate configuration wherein the balloon member 304 is unconstrained from the introducer sheath and uninflated. For example, such manufacturing processes may include rolling the balloon member 304 onto itself and heating the balloon member (e.g., in an oven at about 200° F.) to thermoset the rolled balloon member 304 in the first delivery configuration. As the balloon member 304 exits the introducer sheath, the balloon member 304 elastically deforms to the intermediate configuration which may comprise the balloon member 304 being unrolled and having a substantially planar, flattened shape. The balloon member 304 may further transition to the second configuration where the balloon member 304 is inflated. In some aspects, the second configuration includes an over-inflated configuration which extends the balloon member 304 beyond the flat shape such that a central portion of the balloon member 304 extends outwardly (e.g., to irrigate the tissue via the interior cavity of the balloon member 304, in one aspect). As such, it will be appreciated that the balloon member 304 may comprise multiple expanded configurations (e.g., in the intermediate configuration, in the second deployed configuration, etc.).

Figure 5B:
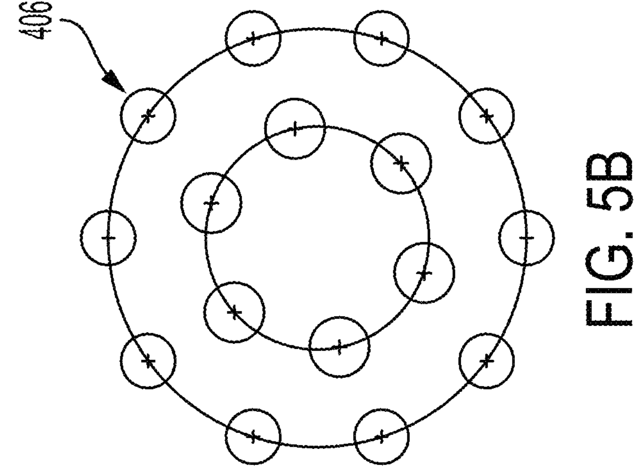
FIG. 5B depicts an alternative arrangement of electrodes of an expandable electrode assembly, in accordance with embodiments of the present disclosure.

In various embodiments, the balloon member 304 includes fold lines, creases, point bonds, dimples, etc. (not shown) to help direct the inflation and/or deflation of the balloon member 304. The balloon member 304 may have a flat/planar, concave, or convex shape in the second deployed configuration. For example, the balloon member 304 may have a fold line down the center of the flat shape which directs the inflated balloon member 304 into a "football" shape. In some embodiments, a central portion of the balloon member 304 may extend above the rest of the top surface and/or the bottom surface of the balloon member 304. Furthermore, although the embodiments illustrated throughout the figures and described herein are substantially oval in shape, the expandable electrode assembly 300 and/or the balloon member 304 may be any shape including a circle (e.g., forming a "lollipop" shape as shown in FIG. 5B), a triangle, a square, a rectangle, etc., or any combination of shapes. Various other embodiments may include the expandable electrode assembly 300 and/or the balloon member 304 having a linear shape or a hoop shape having one or more interior "cut-outs" as would be appreciated by one having ordinary skill in the art in view of the present disclosure. In yet other embodiments, the expandable electrode assembly 300 and/or the balloon member 304 may be a rounded shape such as a sphere, round (e.g., circular), or a balloon shape. In yet further embodiments, the expandable electrode assembly 300 and/or the balloon member 304 may be a basket configuration having inflatable splines. Exemplary embodiments of a rounded shape or basket having inflatable portions may include those described with respect to U.S. Patent Pub. No. 2021-0361220 A1 entitled "Uniform Mapping Balloon" the entire disclosure of which is incorporated herein by reference. Any inflatable portion may be partially inflatable to fully inflated, and vice versa, before, during, and after use as desired for the intended application.

In various embodiments, a substantially flat balloon member enables improved determination of tissue or blood contact at the electrode interface. For example, one side of the substantially flat balloon member may be configured to contact the tissue of interest (e.g., cardiac tissue) while the other side of the substantially flat balloon member is configured to contact blood flow, etc. These discrete and reliable electrode contact points on the flat balloon structure that are independently energized allow for measurements at the blood pool interface to be filtered out to remove any far field artifacts. This in turn provides higher fidelity electrograms (EGMs) with improved signal to noise ratio as compared to conventional mapping techniques known in the art. For example, conventional mapping catheters measure the average of signals at the tissue and blood interface. The discrete contact determination and sensing enabled by the substantially flat balloon structure of the present invention reduces or eliminates such far field effects and unwanted noise in measurements. Additionally, equally spaced electrodes are measured from known directions and associated algorithms do not have to compensate for timing delays. The ability to have discrete contact sides also improves spatial resolution with respect to borders/edges, for example, with respect to high/low voltage, timing maps, etc., as compared to conventional devices.

A further advantageous feature of a substantially flat or planar expandable electrode assembly is that each of the surfaces is able to maintain the electrodes in their desired configurations. For example, the arrangement of the electrodes (e.g., the spacing of the electrodes) remains substantially fixed, even when the distal portion of the expandable electrode assembly contacts tissue or the top surface/bottom surface are bent. This consistent and equal spacing of electrodes in turn provides for improved sensing and diagnostic mapping.

As shown, the balloon member 304 is in the second deployed configuration where the balloon member 304 has a substantially flat shape. The balloon member 304 comprises a top surface 306 and a bottom surface 308. In some embodiments, each of the top surface 306 and the bottom surface 308 of the balloon member 304 includes a plurality of apertures 310. In other embodiments, only one of the top surface 306 and the bottom surface 308 of the balloon member 304 includes a plurality of apertures 310. It should be noted that other shapes are contemplated as the second deployed configuration other than a substantially flat shape. For example, the balloon member 304 may be inflated to a rounded, spherical shape or a rounded, circular shape. In other embodiments, the balloon member 304 may have a "cut-out" where no electrodes or material exists such the balloon member 304 forms a hoop shape and the perimeter of the hoop shape is inflated. In yet further embodiments, the balloon member 304 may be a basket with inflatable spline members that are inflated in the second deployed configuration. The inflatable splines may include a linear, generally rectangular (e.g., cuboidal) shape when in the second deployed configuration or the inflatable splines may be tubular (e.g., cylindrical) when the balloon member 304 is in the second deployed configuration. Each inflatable spline may include a flexible support frame member comprising a shape memory material, according to some embodiments. In other embodiments, the splines are inflated such that the splines are sufficiently stiff to perform the functions of the basket catheter, as would become apparent to one having ordinary skill in the art upon reading the present disclosure.

In various embodiments, a plurality of electrodes 312 extend within and are exposed through the top surface 306 and/or the bottom surface 308 of the balloon member 304. For example, a first plurality of electrodes may extend within and be exposed through the top surface 306 and a second plurality of electrodes (not shown) may extend within and be exposed through the bottom surface 308. In various exemplary aspects, the plurality of apertures 310 may have a diameter in a range from 0.25 mm to 3 mm and the electrodes 312 may have a diameter in a similar range from 0.25 mm to 3 mm. In other aspects, the diameter of plurality of apertures 310 and the diameter of the electrodes 312 may have any desired dimension. In preferred embodiments, the electrodes 312 are between about 0.002 and about 0.010 larger than the apertures 310. In other embodiments, the diameter of the apertures 310 are the same size as the diameter of the electrodes 312. In yet other embodiments, the diameter of the apertures 310 are larger than the diameter of the electrodes 312. In each embodiment, there may be an insulating seal (not shown) between the electrode 312 and the aperture 310 for reducing impedance.

In at least some embodiments, a top surface of each of the electrodes 312 may be polished flush with the top of the respective aperture 310. For example, the top surface 306 and/or the bottom surface 308 may be substantially planar, flat, smooth, etc. In other embodiments, a top surface of each of the electrodes 312 may be proud (e.g., raised with respect to the top surface of the balloon member 304) compared to the top of the respective aperture 310 for improving the tissue contact between the electrodes 312 and the tissue of interest. For example, the electrodes 312 may extend 0.1 mm to 0.5 mm above the top surface 306 of the balloon member 304. In yet other embodiments, the top surface of each of the electrodes 312 may be recessed into the respective aperture 310. For example, the electrodes 312 may extend 0.1 mm to 0.5 mm below the top surface 306 of the balloon member 304. Recessed electrodes may be coated for impedance reduction. In various embodiments, an impedance reducing, polymer coating is not flush with the apertures 310 for the electrodes 312. Both the electrodes 312 and an impedance reducing coating may be recessed for protection from abrasion. For example, abrasion to the electrodes may result from deployment of the balloon member 304 through a sheath as the electrodes pass over the sheath material into the vasculature. In at least some embodiments, the impedance reducing, polymer coating may substantially fill the recess (e.g., the gap between the electrode and the topmost surface of the top surface 306). The impedance reducing, polymer coating may include various materials such as those described in detail with respect to International Publication No. WO 2022187161 A1 entitled, "Electrode with Protected Impedance Reduction Coating", the entire disclosure of which is incorporated herein by reference. It should be understood that any embodiment describing the top surface 306 and its components may be similarly applicable to the bottom surface 308 and its components.

Figure 4A:
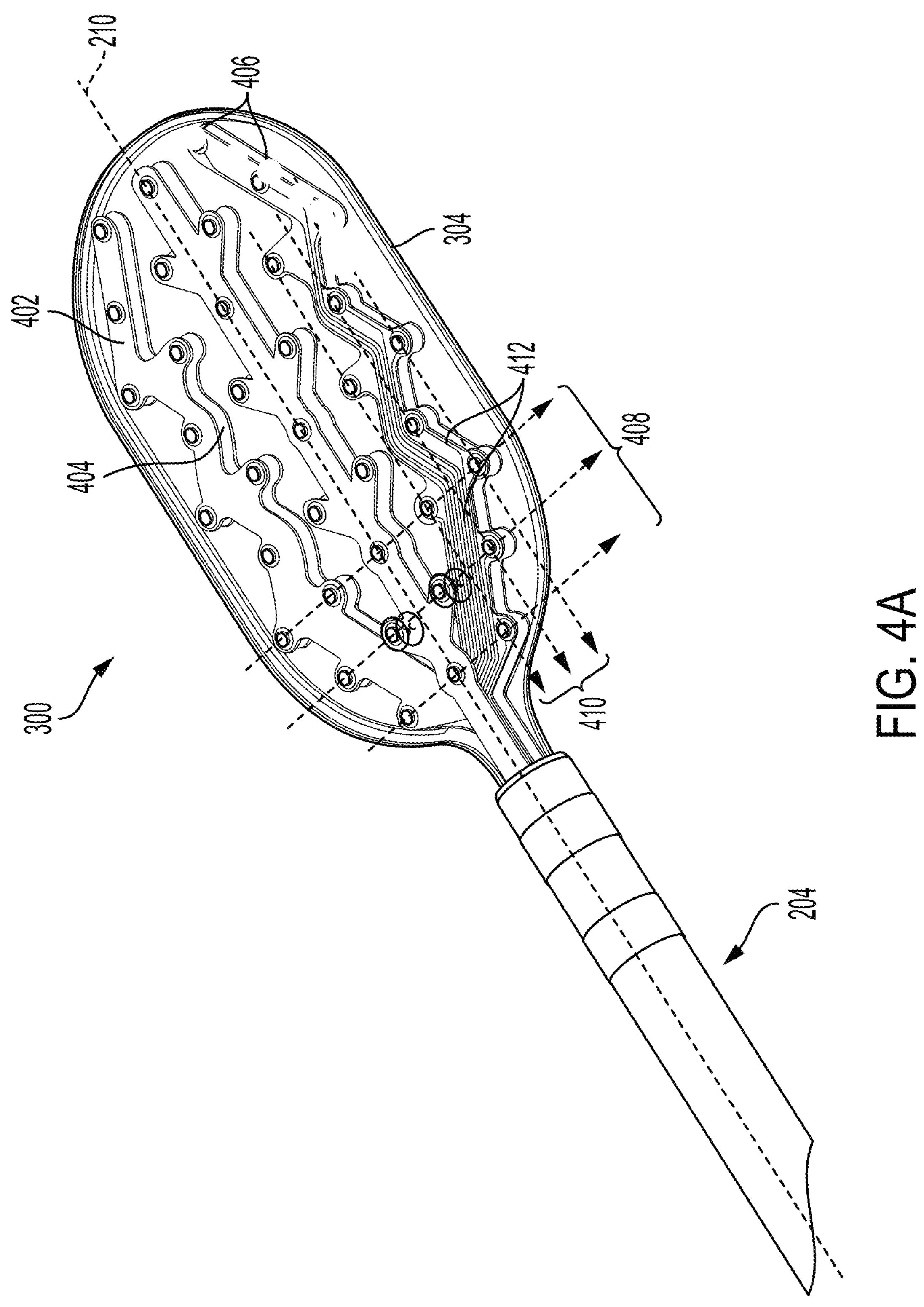
FIG. 4A depicts a partially cross-sectional top view of an expandable electrode assembly, in accordance with embodiments of the present disclosure.

FIG. 4A depicts an expandable electrode assembly 300 including a balloon member 304 shown with a top surface removed for depicting various internal components of the balloon member 304, in accordance with embodiments described in the present disclosure. In some embodiments, the balloon member 304 includes a top flexible framework 402 associated with a top surface and a bottom flexible framework 404 associated with a bottom surface. In other embodiments, the balloon member 304 includes a single flexible framework associated with a single planar surface of the balloon member 304.

The top flexible framework 402 and the bottom flexible framework 404 may comprise a variety of flex circuit materials including polyimide, thermoplastics, Pebax, polyurethanes, and like polymers. In various embodiments, the bottom flexible framework 404 may be the same (e.g., including the same size, shape, layout, etc.) and is associated with the same components as the top flexible framework 402, although only the components associated with the top flexible framework 402 are shown in FIG. 4A. In various embodiments, the top flexible framework 402 and the bottom flexible framework 404 are not the same shape, size, layout, etc. For example, electrodes disposed on each of the top flexible framework 402 and the bottom flexible framework 404 are not mirrored on the top surface 306 and the bottom surface 308 of the balloon member 304. For example, branches of the top flexible framework 402 and the bottom flexible framework 404 may interleave one another in a top view of the top flexible framework 402 and the bottom flexible framework 404.

A first plurality of electrodes 406 are patterned onto the top flexible framework 402. Each of the first plurality of electrodes 406 are arranged in horizontal rows 408 relative to the longitudinal axis 302 defined by the elongate catheter shaft 204. For example, the first plurality of electrodes 406 are arranged in horizontal rows 408 which are perpendicular to the longitudinal axis 302 (e.g., 90° offset from the longitudinal axis 302). The horizontal rows 408 are offset such that each electrode of the first plurality of electrodes 406 is offset from a respective electrode in an adjacent row. For example, each electrode in a horizontal row 408 may be equally spaced between two electrodes in an adjacent horizontal row 408. In one embodiment, the offset is 60°. The offset may be in a range from 22.5° to 60°.

In preferred embodiment, each electrode in each row is equally spaced from adjacent electrodes in the same row and adjacent rows. For example, a center-to-center distance between each electrode in a row is the same as the center-to-center distance between an electrode and the two electrodes in the adjacent row that the electrode is positioned between. In other embodiments, the center-to-center distance between each electrode in the first plurality of electrodes is between about 0.5 mm to about 4 mm. In one exemplary embodiment, each electrode in the first plurality of electrodes has a diameter of 0.25 mm such that the edge-to-edge spacing is 0.25 mm and the center-to-center spacing is 0.5 mm. According to various configurations described herein, the spatially and electrically arranged electrodes provide improved resolution of resulting images from the mapping system and improved high fidelity signals. In various aspects, tighter spacing is preferred as it reduces compensation for timing between signals and provides improved resolution of resulting images from the mapping system. Similarly, each of the first plurality of electrodes 406 may be arranged in vertical rows 410 which are parallel to the longitudinal axis 302 defined by the elongate catheter shaft 204. The vertical rows 410 may be offset such that each electrode in each row is offset from a respective electrode in an adjacent row. For example, an electrode in a first vertical row may be positioned between two adjacent electrodes in an adjacent row.

It should be understood that a second plurality of electrodes (not shown) are similarly patterned onto the bottom flexible framework 404. In preferred embodiments, the first plurality of electrodes 406 and the second plurality of electrodes are aligned such that an electrode on the top surface of the balloon member 304 matches with an electrode on the bottom surface of the balloon member 304. In some aspects, the first plurality of electrodes 406 and the second plurality of electrodes do not align with each other.

Figure 4B:
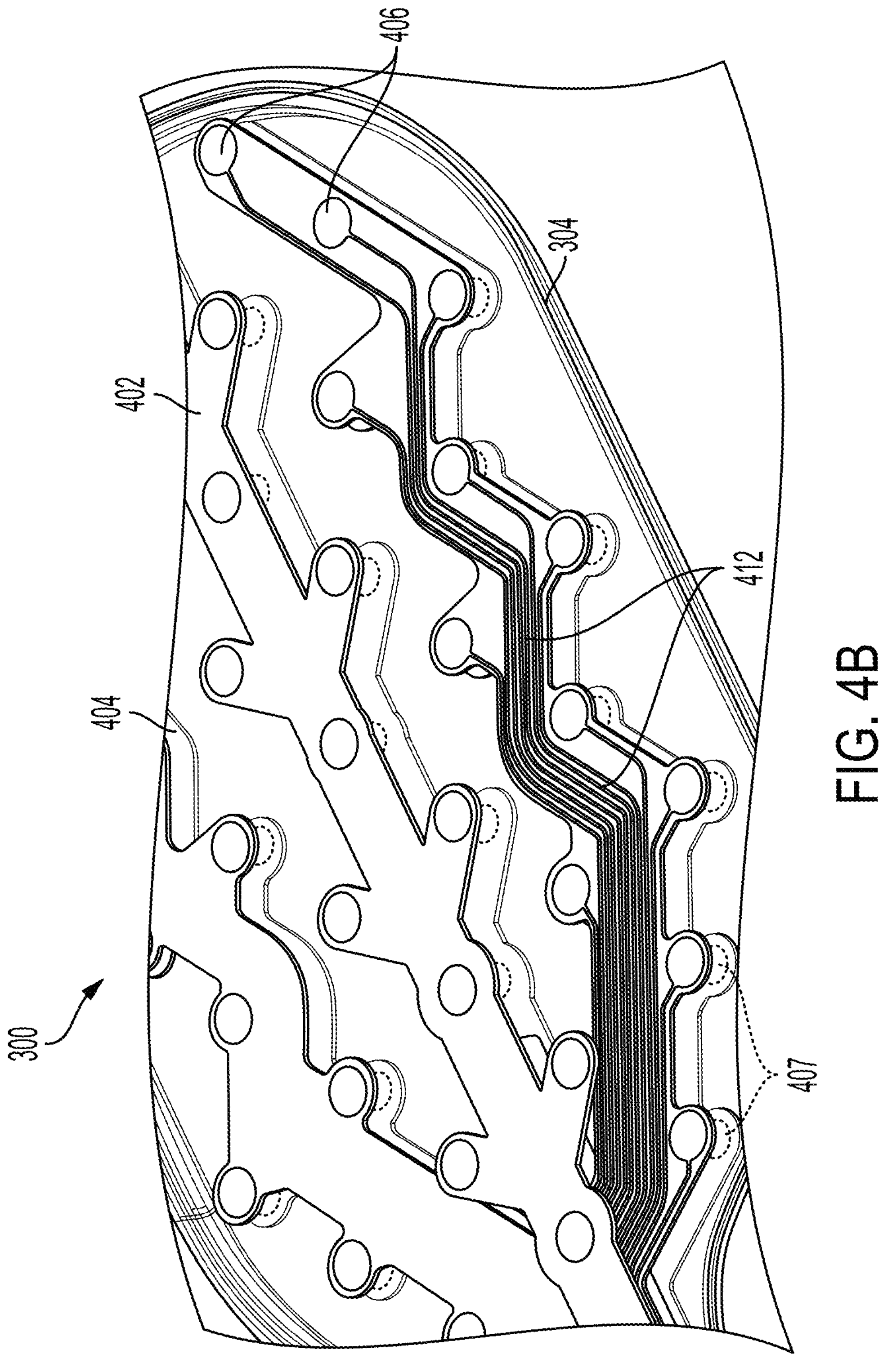
FIG. 4B depicts an exploded view of conductive traces on a flexible framework of an expandable electrode assembly, in accordance with embodiments of the present disclosure.

FIG. 4B depicts an exploded view of an exploded view of conductive traces 412 on a flexible framework 402 of an expandable electrode assembly 300. In various embodiments, a plurality of conductive traces 412 are disposed on each of the top flexible framework 402 and the bottom flexible framework 404. The plurality of conductive traces 412 on each of the flexible frameworks is electrically coupled with a respective one of the first plurality of electrodes 406 and the second plurality of electrodes. It should be noted that not all of the plurality of conductive traces 412 are shown in FIG. 4 for simplicity although the plurality of conductive traces 412 would electrically couple to each of the electrodes in the first plurality of electrodes 406 in practice. In embodiments having electrodes disposed on only one flexible framework in the balloon member 304, a single plurality of conductive traces 412 would be provided to electrically couple to the respective plurality of electrodes, as would become apparent to one having ordinary skill in the art upon reading the present disclosure. Embodiments of the conductive traces and the electrodes disposed on the flexible framework (e.g., as flex circuits)

may be implemented according to any of the aspects described in U.S. Pat. No. 11,642,064, assigned to the assignee herein, filed on Feb. 4, 2020, and titled: "High Density Electrode Mapping Catheter," the entirety of which is hereby incorporated by reference herein.

As shown in FIG. 4B, the first plurality of electrodes 406 and a second plurality of electrodes 407 are disposed on the top flexible framework 402 and the bottom flexible framework 404, respectively. In various embodiments, each of the first plurality of electrodes 406 and the second plurality of electrodes 407 are configured for independent sensing or energy delivery for any of the applications described in detail above. For example, each plurality may be selectively deactivated or one or more of the electrodes in a plurality of electrodes may be selectively deactivated. In various embodiments, any number of electrodes may be included in each of the first plurality of electrodes 406 and the second plurality of electrodes 407. In one exemplary aspect, each of the first plurality of electrodes 406 and the second plurality of electrodes includes 37 electrodes, providing a total of 74 electrodes distributed along and across the longitudinal axis 302 of the balloon member 304, although any number of electrodes may be used on the top surface 306 and the bottom surface 308. For example, in some embodiments, the first plurality of electrodes 406 and/or the second plurality of electrodes 407 includes less than or equal to 100 electrodes. In some aspects, the top surface 306 and the bottom surface 308 include the same number of electrodes. In other aspects, the top surface 306 and the bottom surface 308 include a different number of electrodes. The electrodes may be any shape or configuration. For example, the electrodes may be bar, spot, square, diamond, round electrodes, or any combination thereof.

Figure 5A:
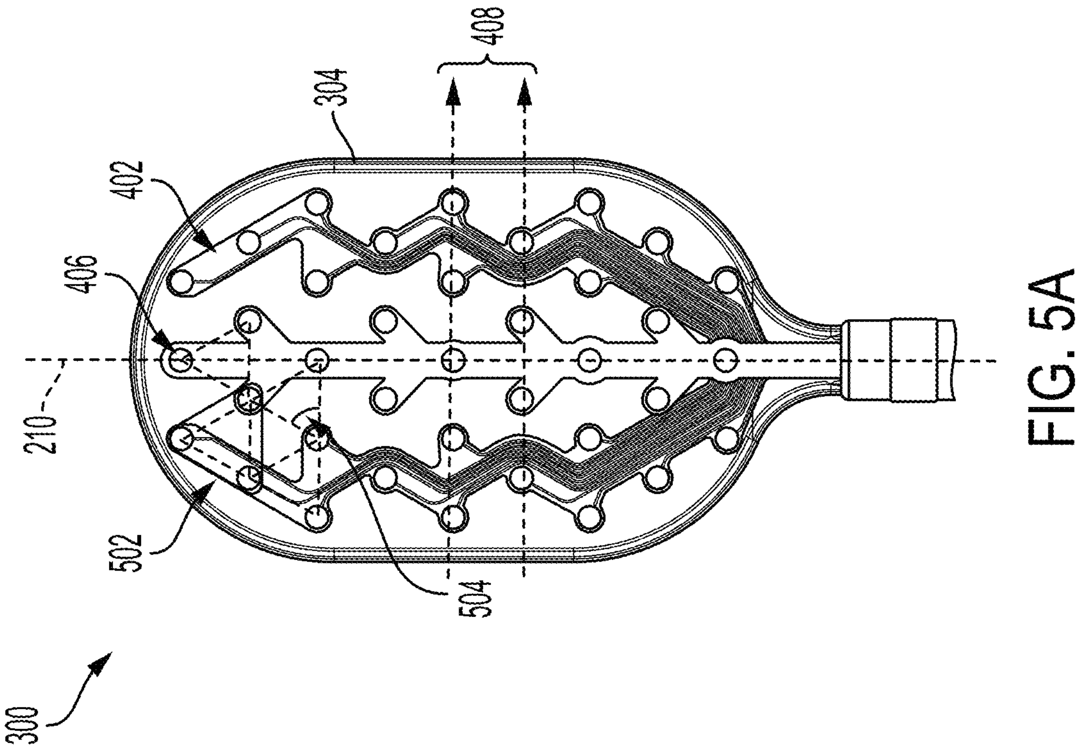
FIG. 5A depicts another partially cross-sectional top view of an arrangement of electrodes of an expandable electrode assembly, in accordance with embodiments of the present disclosure.

Referring now to FIG. 5A, an expandable electrode assembly 300 includes a flexible balloon member (e.g., a balloon member) 304 having a first plurality of electrodes 406 patterned onto a top flexible framework 402. The first plurality of electrodes 406 are patterned into horizontally offset rows 408 as described in detail with respect to FIGS. 4A-4B.

As shown in FIG. 5A, each of the electrodes in the first plurality of electrodes 406 are grouped into cliques 502 of three or more electrodes defining a two-dimensional shape. For example, the cliques of three or more electrodes may be defined according to embodiments described in U.S. Pat. Pub. No. 2020/0214635 entitled "Catheter with High-Density Mapping Electrodes", and using associated algorithms described in U.S. Pat. No. 10,758,137 entitled "Orientation Independent Sensing, Mapping, Interface and Analysis Systems and Methods", the entire of both disclosures are incorporated herein by reference. Further algorithms may be used such as those described in U.S. Pat. No. 10,194,994 entitled "Systems and Methods for Orientation Independent Sensing," the entirety of which is incorporated herein by reference. The cliques 502 of electrodes are preferably configured in an equilateral triangular shape, each clique having at least three electrodes, based on the equal, offset spacing described in detail above. In various embodiments, the cliques 502 of electrodes are configured to sample electrical characteristics of contacted tissue in at least two substantially traverse directions as further described in U.S. Pat. Pub. No. 2020/0214635. In one embodiment, an offset between the electrodes is 60° as illustrated by offset 504 in FIG. 5A. In various embodiments, cliques 502 of three or more electrodes defining a two-dimensional shape may be disposed on a linear balloon member for forming a linear catheter having a cylindrical (e.g., tubular) or cuboidal 3-dimensional shape. In other embodiments, the expandable electrode assembly 300 may be a basket assembly comprising a plurality of balloon members 304 as the splines of the basket assembly. For example, cliques 502 of three or more electrodes defining a two-dimensional shape may be disposed on a linear balloon member and a plurality of these linear balloon members may form a basket assembly having inflatable splines. In yet another embodiment, cliques 503 of three or more electrodes may be disposed on a hoop shape, e.g., a linear balloon member formed into a circle having an aperture therethrough, as would be apparent to one having ordinary skill in the art upon reading the present disclosure.

In other embodiments, the first plurality of electrodes 406 are arranged in any desired configuration. For example, as shown in FIG. 5B, the first plurality of electrodes 406 may be arranged in concentric rings having even spacing along the circumference of each of the rings. In various other aspects, the first plurality of electrodes 406 are not equally spaced. Rather, the first plurality of electrodes 406 may be arranged in high-density electrode zones on a top surface of the balloon member 304. In this manner, the density of electrodes may be adjusted to various configurations for global, regional, or local mapping applications.

Figure 6:
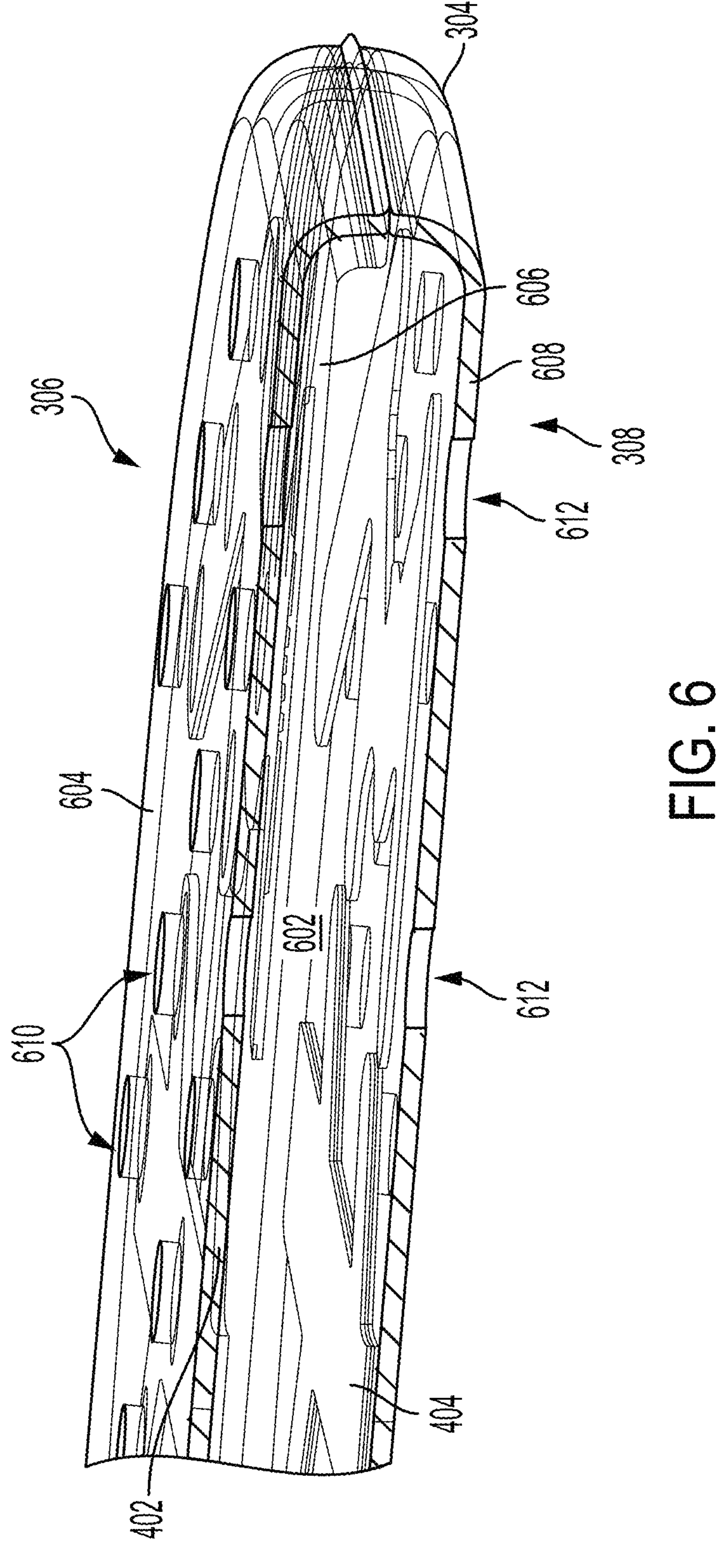
FIG. 6 depicts a perspective, cross-sectional view of an expandable electrode assembly, in accordance with embodiments of the present disclosure.

Referring now to FIG. 6, a cross-section of a balloon member 304 is shown. As shown, the balloon member 304 includes a top surface 306 and a bottom surface 308 and an interior cavity 602. In various embodiments, the top surface 306 includes an outer facing layer 604 and inner facing layer 606. The bottom surface 308 similarly includes an outer facing layer 608 and an inner facing layer (not shown). The inner facing layer 606 of the top surface 306 and the inner facing layer of the bottom surface 308 define the interior cavity 602. In various embodiments, the top flexible framework 402 is disposed between the outer facing layer 604 and the inner facing layer 606 of the top surface 306 of the balloon member 304. Similarly, the bottom flexible framework 404 is disposed between the outer facing layer 608 and the inner facing layer of the bottom surface 308 of the balloon member 304. In aspects having electrodes disposed on only one surface of the balloon member, a flexible framework may be disposed between a top facing layer and a bottom facing layer with electrodes disposed on one side of the flexible framework.

As depicted in FIG. 6, a balloon member 304 includes a first plurality of apertures 610 on the outer facing layer 604 of the top surface 306 of the balloon member 304 and a second plurality of apertures 612 on the outer facing layer 608 of the bottom surface 308 of the balloon member 304. Each of the first and second plurality of apertures 610, 612 are configured to expose the respective first plurality of electrodes and second plurality of electrodes (not shown). The first and second plurality of electrodes may be flush, recessed, or raised with respect to the outer facing layer 604 of the top surface 306 of the balloon member 304 and the outer facing layer 608 of the outer facing layer 608 of the bottom surface 308 of the balloon member 304.

Figure 7:
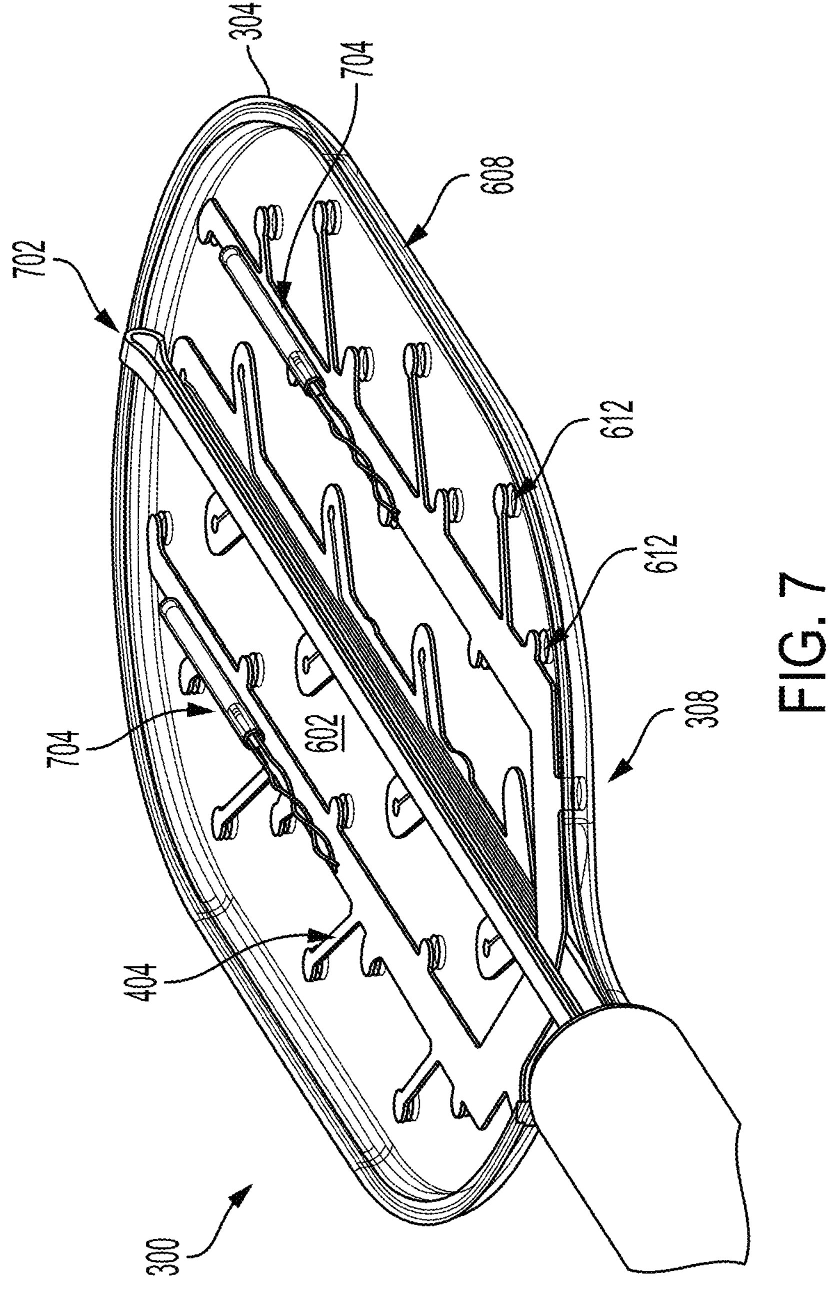
FIG. 7 depicts another perspective, cross-sectional view of an expandable electrode assembly, in accordance with embodiments of the present disclosure.

Referring now to FIG. 7, the balloon member 304 having the top surface and various associated components removed for simplicity in viewing interior cavity 602. An outer facing layer 608 of the bottom surface 308 of the balloon member 304 is shown having the bottom flexible framework 404. As depicted in FIG. 7, a flexible structural element 702 is disposed within the interior cavity 602 of the balloon member 304 for providing rigidity and to preventing kinking of the balloon member 304 when the balloon member 304 is deployed in a patient. In various embodiments, the flexible structural element 702 comprises a nitinol wire looped element extending along the longitudinal axis (e.g., longitudinal axis 302) defined by the elongate catheter shaft (e.g., elongate catheter shaft 204). In other embodiments, the flexible structural element 702 may have any configuration including extending along a perimeter of the balloon member 304, an internally flat shape (when viewed from a top perspective) substantially mirroring the perimeter of the balloon member 304, a pronged shape extending from the longitudinal axis, etc. In various embodiments the nitinol wire looped element is disposed between the top flexible framework and the bottom flexible framework.

In some aspects, the expandable electrode assembly 300 and the balloon member 304 does not include the flexible structural element 702 where inflation of the balloon and/or the balloon material provides enough rigidity to avoid kinking and/or any other unwanted bending. For example, overinflating the balloon member 304 may create a substantially rigid structure to prevent unwanted bending when the balloon member 304 is deployed and underinflating the balloon member 304 may create additional flexibility if desired for conforming to a tissue of interest. It may be desirable to temporarily and incrementally deflate the balloon member 304 to conform to a particularly uneven tissue surface.

The interior cavity 602 includes one or more magnetic position sensors 704 (e.g., such as location sensors 106 described in detail with respect to FIG. 1). In various embodiments, the magnetic position sensors 704 are disposed on the top flexible framework and/or on the bottom flexible framework 404 (as shown) on a distal portion of the expandable electrode assembly. The magnetic position sensors 704 are coupled to the top flexible framework and/or on the bottom flexible framework 404 and parallel to the longitudinal axis of the catheter shaft.

Referring now to FIGS. 8A-8C, various cross-sections of a balloon member 304 show combinations of a top surface 306 having an outer facing layer 604 and an inner facing layer 606, a bottom surface 308 having an outer facing layer 608 and inner facing layer 802, a top flexible framework 402, a bottom flexible framework 404, a first plurality of apertures 610, a second plurality of apertures 612, a flexible structural element 702, magnetic position sensors 704, and an interior cavity 602.

For example, as shown in FIG. 8A, a perspective cross-section of the balloon member 304 showing the relative positions of a top surface 306, a bottom surface 308, a first plurality of apertures 610, a second plurality of apertures 612, a flexible structural element 702, magnetic position sensors 704, and an interior cavity 602, in accordance with one embodiment. The magnetic position sensors 704 may be offset at an angle relative to the flexible structural element 702, in at least some embodiments.

In another example, FIG. 8B includes a straight-on view of a cross-section of the balloon member 304 showing the top surface 306 relative to the bottom surface 308, a first plurality of apertures 610 extending through the top surface 306 and through the outer facing layer 604, a second plurality of apertures 612 extending through the bottom surface 308 and through the outer facing layer 608. The magnetic position sensors 704 are shown within the interior cavity 602. The top flexible framework 402, the bottom flexible framework 404, and the flexible structural element 702 are removed in this view.

In yet another example, FIG. 8C includes a straight-on view of a cross-section of the balloon member 304 showing the top surface 306 relative to the bottom surface 308, a first plurality of apertures 610 extending through the top surface 306 through the outer facing layer 604, and a second plurality of apertures 612 extending through the bottom surface 308 through the outer facing layer 608. As shown in FIG. 8C, the top flexible framework 402 is sandwiched between the top surface 306 outer facing layer 604 and inner facing layer 606. Similarly, the bottom flexible framework 404 is sandwiched between the bottom surface 308 outer facing layer 608 and inner facing layer 802. The interior cavity 602 is defined by the top surface 306 inner facing layer 606 and the bottom surface 308 inner facing layer 802. The magnetic position sensors 704 and the flexible structural element 702 are removed in this view.

In various embodiments, the balloon member 304 including various of the components described above is formed using twin sheet thermoforming. Twin sheet thermoforming may comprise vacuum forming or pressure forming two sheets simultaneously using two molds on each platen. Once formed, the top and bottom platens are brought together quickly (e.g., so as not to lose surface temperature). For example, once formed, the top surface 306 outer facing layer 604 and inner facing layer 606 have the top flexible framework 402, a plurality of conductive traces 412, and the first plurality of electrodes 406 laminated therebetween. The bottom surface 308 outer facing layer 608 and inner facing layer 802, the bottom flexible framework 404, a plurality of conductive traces 412, and the second plurality of electrodes laminated therebetween. The first and second plurality of apertures 610, 612 may be formed in the respective top surface 306 and bottom surface 308 before or after the twin sheet thermoforming. In various implementations, a sealant and/or insulative layer is provided between the electrodes and/or the conductive traces prior to the twin sheet thermoforming. In at least some embodiments, the magnetic position sensors 704 are coupled to the top flexible framework 402 and/or the bottom flexible framework 404 and are laminated with each of the other components during the twin sheet thermoforming process. For example, the magnetic position sensors 704 are structurally incorporated into the top surface 306 and/or the bottom surface 308. In various embodiments, magnetic sensors of various designs may be incorporated into the top surface 306 and/or the bottom surface 308. For example, magnetic sensors including those discussed in U.S. Pat. No. 11,439,318 entitled, "Active Magnetic Position Sensor", the entire disclosure of which is incorporated herein by reference, may be used in some embodiments. In various embodiments, printed versions of passive pickup coils may be used such as those discussed in U.S. Patent Pub. No. 2022/0008011 A1 entitled, "Printed Sensor Coil", the entire disclosure of which is incorporated herein by reference. The twin sheet thermoforming process substantially fixes the position of the various components relative to each other within the top surface 306 and/or the bottom surface 308. Implementations of this process enables batch manufacturing and reduces the cost of goods while providing more features (e.g., higher quality EGMs and spatial resolution) for the same or lower cost. For example, the features of the embodiments described herein may be manufactured with significant less touch-time as compared to conventional designs.

Figure 9:
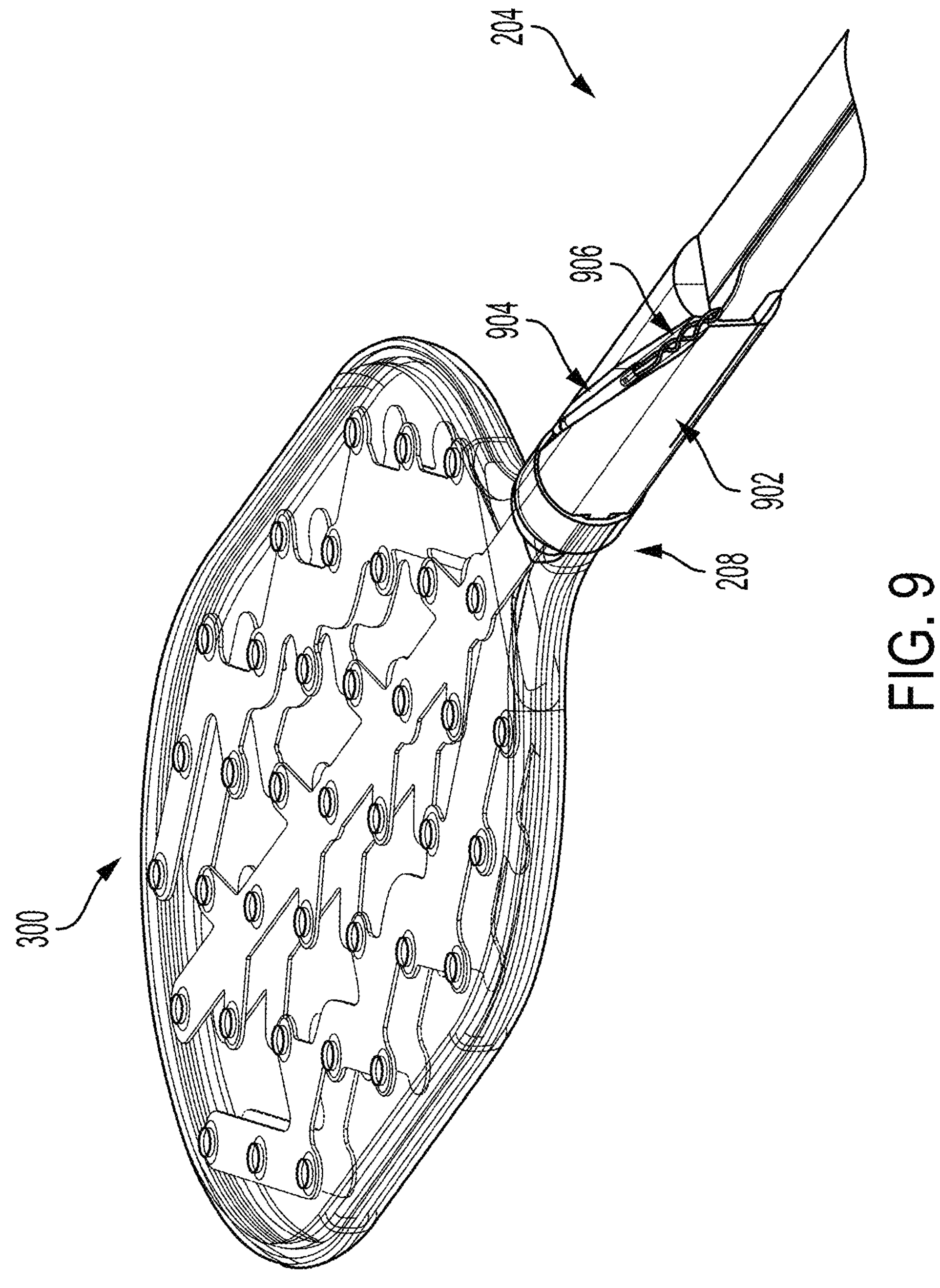
FIG. 9 depicts a cross-sectional perspective view of an expandable electrode assembly, in accordance with embodiments of the present disclosure.

Referring now to FIG. 9, a catheter shaft 204 coupled to an expandable electrode assembly 300 at a distal end 208 of the catheter shaft 204 is shown. In particular, according to at least some embodiments, the expandable electrode assembly 300 is coupled to the distal end 208 of the catheter shaft 204 using a proximal coupler 902. According to at least some embodiments, the proximal coupler 902 is a two-part proximal coupler. In at least some embodiments, each piece of the two-part proximal coupler 902 has an angled offset, which, when each piece of the two-part proximal coupler 902 is aligned with each other, accommodates a shaft magnetic position sensor 904 (e.g., such as location sensors 106 described in detail with respect to FIG. 1) and corresponding magnetic sensor wires 906. For example, the shaft magnetic position sensor 904 is offset with respect to the longitudinal axis of the catheter shaft 204. In at least some embodiments, the offset shaft magnetic position sensor 904 is located at an angle of 11° with respect to the longitudinal axis of the catheter shaft 204, or alternatively, with respect to the magnetic position sensors 704 (not shown in FIG. 9).

Figures 10A, 10B, 10C:
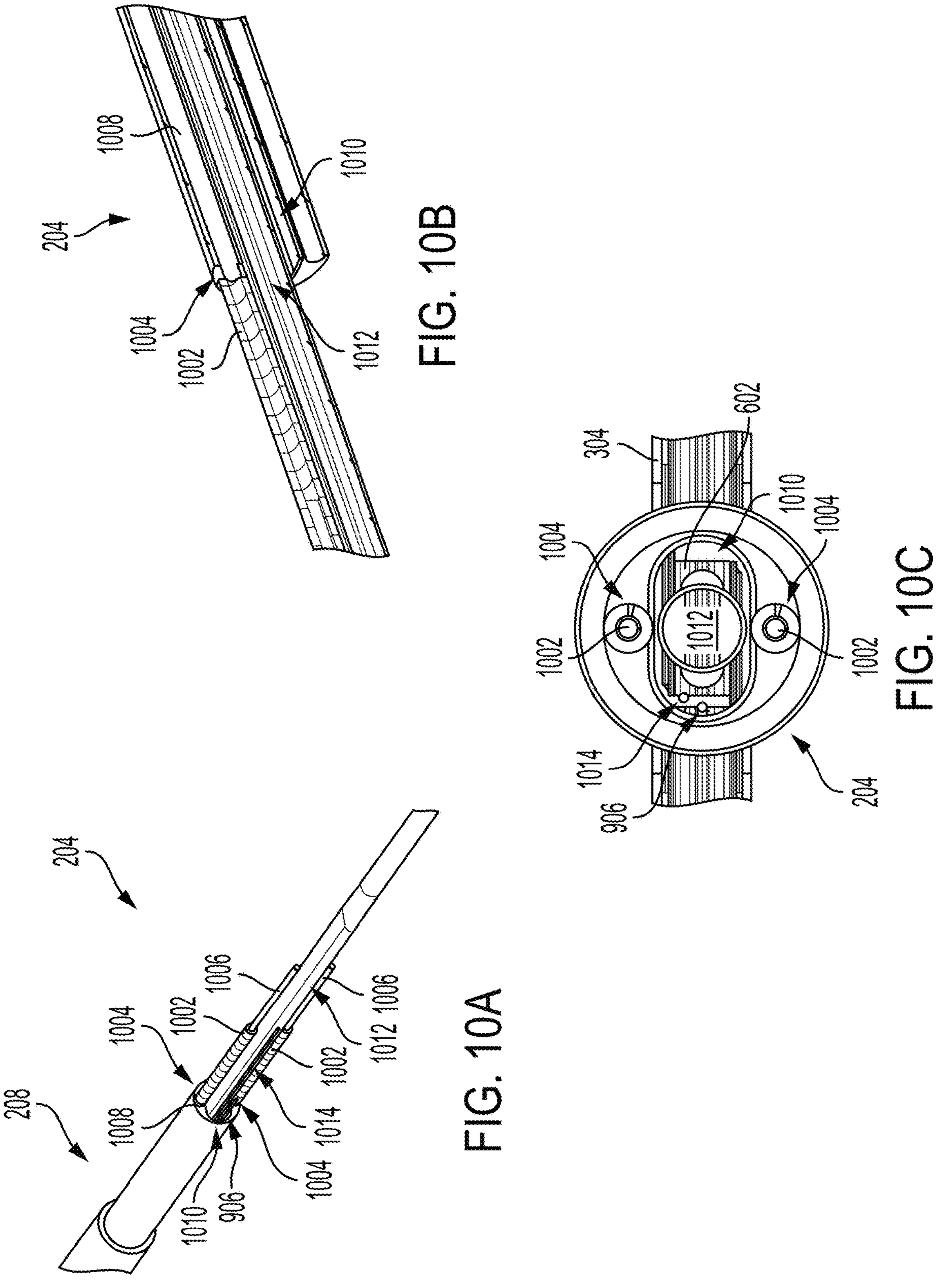
FIG. 10A depicts a perspective view of a distal end of an elongate catheter shaft, in accordance with embodiments of the present disclosure.
FIG. 10B depicts a perspective, cross-sectional view of a distal end of an elongate catheter shaft, in accordance with embodiments of the present disclosure.
FIG. 10C depicts a cross-sectional view of a distal end of an elongate catheter shaft, in accordance with embodiments of the present disclosure.

Referring to FIGS. 10A-10C, various embodiments of a catheter shaft 204 are shown. In various embodiments, the catheter shaft 204 includes a non-deflectable portion extending distally from the handle (such as handle 210), and a deflectable portion extending distally from the distal end of a non-deflectable portion. As shown in FIG. 10A, the catheter shaft 204 (in particular, a deflectable portion of the catheter shaft 204) includes one or more compression coils 1002 extending at least partially down the length of pull-wire lumens 1004. For example, each pull-wire lumen 1004 can include a compression coil 1002. The compression coils 1002 can be partially affixed to at least a portion of the interior of the pull-wire lumen 1004. As seen, each pull-wire 1006 extends through a pull-wire lumen 1004. In at least some embodiments, a compression coil adapter 1008 is provided at the distal end of one or both of the compression coils 1002. The compression coil adapter 1008 extends around the distal end of the compression coils 1002 and extends beyond the length of the compression coils 1002 into the pull-wire lumens 1004 for accommodating the size of central lumen 1010 having an inflation lumen 1012 within the central lumen 1010. The magnetic sensor wires 906 may extend through the central lumen 1010 into the catheter shaft 204 as shown. Additional wiring 1014 (e.g., electrode wiring) may extend through the central lumen 1010 into the catheter shaft 204.

Further shown in FIG. 10A, an inflation lumen 1012 is provided for inflating and deflating the expandable electrode assembly with a gas, liquid, or combination thereof. For example, the inflation lumen 1012 terminates in the interior cavity 602 of the balloon member 304 and the gas and/or liquid expands the balloon member 304. In various embodiments, the expandable electrode assembly may be irrigated using the same inflation lumen 1012 used for inflating and deflating the expandable electrode assembly. For example, the inflation lumen 1012 may be configured to deliver saline to prevent clotting on and/or around the expandable electrode assembly. The first plurality of apertures 610 and/or the second plurality of apertures 612 may be configured to allow an amount of fluid to secrete therethrough. For example, some or all of the apertures may not be sealed and/or are partially sealed to provide a desired amount of irrigation fluid therethrough. In use, a practitioner may choose to over-inflate the expandable balloon assembly with saline such that the saline secretes through the first plurality of apertures 610 and/or the second plurality of apertures 612.

FIG. 10B depicts a cross-section of a catheter shaft 204 showing a compression coil 1002 and a compression coil adapter 1008 extending at least partially within the pull-wire lumen 1004 and the inflation lumen 1012 extending at least partially into the central lumen 1010.

FIG. 10C depicts a different cross-section of a catheter shaft 204 showing the compression coils 1002 in the pull-wire lumens 1004 and the inflation lumen 1012 in the central lumen 1010. As depicted in FIG. 10C, the inflation lumen may transition from a circular cross-section, or substantially rounded cross-section, to a flattened, oval-shaped cross-section. The transition may occur through the central lumen 1010 or as the inflation lumen 1012 crosses into the interior cavity 602 of the balloon member 304.

In other embodiments of the present disclosure, the expandable electrode assembly comprises a substantially flat pad having a similar configuration. The pad expandable electrode assembly expands from the introducer sheath in a similar fashion as other embodiments described herein. The pad structure is preferably a silicone pad structure. The pad expandable assembly includes a top surface and a bottom surface, and a flexible framework disposed between the top and bottom surface. A plurality of electrodes and corresponding conductive traces may be patterned onto the flexible framework according to any of the embodiments described herein, such as in a horizontally offset pattern (as described at least with respect to FIGS. 4 and 5A). In some aspects, the silicone pad structure includes an interior cavity between the top surface and the bottom surface, and the flexible structural element is disposed within the interior cavity. In other aspects, the silicone pad structure does not have an interior cavity when the components are placed in a mold and the silicone is injection molded to form the silicone pad structure.

Figure 11:
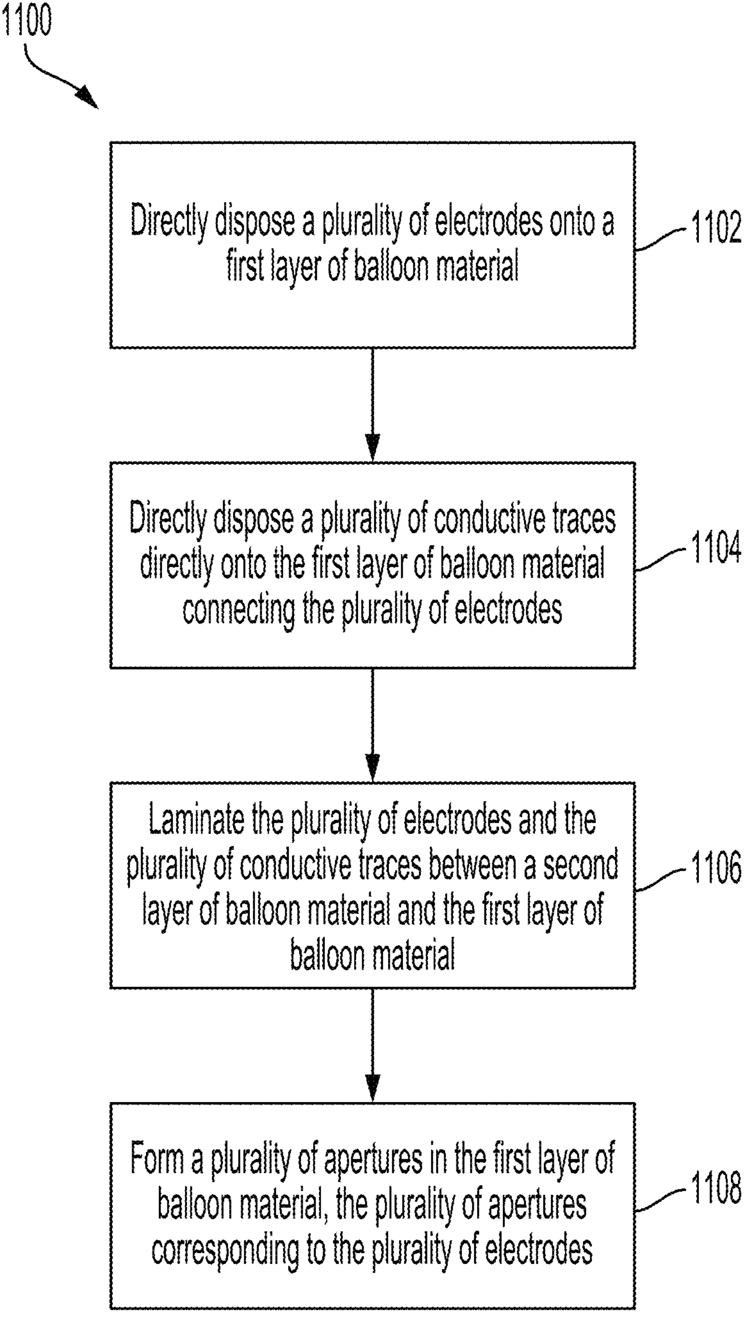
FIG. 11 is a flowchart of a manufacturing method, in accordance with embodiments of the present disclosure.

FIG. 11 is a flowchart of a method 1100 of manufacture for an expandable electrode assembly, such as any of the expandable electrode assemblies described herein. In one embodiment, electrodes and corresponding conductive traces may be built (e.g., disposed) onto the outer layer of the top surface and/or the outer layer of the bottom surface of the balloon member. The balloon member may comprise a variety of biocompatible materials including thermoplastic polyurethanes (TPUs), thermoplastic elastomers (TPEs), polyamides including nylons or Pebax, ethylene vinyl acetates (EVAs), polyvinylidene fluoride (PVDF), polyvinyl chloride (PVC), silicon, silicone, and/or composite materials thereof. In particular, one embodiment of assembling the expandable electrode assembly 300, as described in detail above, includes disposing electrodes and/or conductive traces onto balloon material.

As shown, step 1102 includes disposing a plurality of electrodes onto a first layer of balloon material. The electrodes may have any size and configuration described herein. In one exemplary aspect, the electrodes are gold electrode pads having a diameter of 1 mm and a height of 0.002 mm. In other aspects, a thin sheet of gold is applied to the first layer of balloon material. Apertures formed in step 1108 expose portions of the thin sheet of gold to form the electrodes, in some aspects.

Step 1104 includes disposing a plurality of conductive traces onto the first layer of the balloon material corresponding to the plurality of electrodes. In one embodiment, the plurality of conductive traces are drawn with a conductive epoxy ink. The plurality of conductive traces are disposed to connect the plurality of electrodes. In various embodiments, an insulating layer may be applied to between each of the plurality of conductive traces. In at least some aspects, a stencil is used to create the plurality of conductive traces.

In other aspects, step 1104 includes applying a conductive epoxy to the first layer of balloon material having the plurality of electrodes disposed thereon. For example, a conductive ink may be applied onto the first layer of balloon material having the plurality of electrodes disposed thereon.

Step 1106 includes laminating the plurality of electrodes and the plurality of conductive traces between a second layer of balloon material and the first layer of balloon material.

The two layers of balloon material may be joined and/or sealed using twin sheet thermoforming process as described in detail herein.

Step 1108 includes forming a plurality of apertures in the first layer of balloon material. The plurality of apertures correspond to the plurality of electrodes such that the plurality of electrodes extending within and are exposed through the plurality of apertures. In various embodiments, the plurality of apertures are laser etched away from the first layer of balloon material. In some aspects, an insulative coating may be applied to the exposed electrodes. In various embodiments, a conductive, impedance lowering coating is applied. For example, a conductive, impedance lowering coating may include Poly (3,4-ethylenedioxythiophene) (PEDOT), Pebax, titanium nitride, or the like, or any other materials described in detail with respect to International Publication No. WO 2022187161 A1 referenced above and incorporated by reference in its entirety. In at least some embodiments, the surface of the layer may be physically modified, instead of or in combination with, the addition of the conductive, impedance lowering coating. Physical modifications may include increasing the roughness of the first layer to alter the impedance (but not the conductivity) and increase the surface area of the first layer for increasing contact area as would be appreciated by one having ordinary skill in the art upon reading the present disclosure. In some embodiments, individual electrodes include a copper trace and a copper pad plated with gold. The gold insulates the copper components of the electrode. According to some embodiments, the electrodes may further include a conductive, impedance lowering insulating layer. For example, the electrode may be further coated with iridium oxide to provide to reduce the impedance and to achieve an adequate signal-to-noise ratio. In various embodiments, non-coated flex electrodes may be plated with noble metals including gold, palladium, platinum, alloys thereof such as platinum iridium (PtIr), combinations thereof, etc.

In at least some embodiments, the plurality of conductive traces merge at a distal end of a catheter shaft. In one embodiment, the plurality of conductive traces form a serpentine pattern along the remaining length of the catheter shaft. The serpentine pattern on the catheter shaft may be separate from any conductive epoxy ink used in the previous depositions, in some embodiments. The serpentine pattern prevents breakage of the conductive traces during tension and compression of the catheter shaft as well as prevents the conductive traces from breaking when the catheter shaft is bent. The serpentine pattern further prevents breakage of the traces during stretch and as such increases the flexibility of the expandable electrode assembly.

In other embodiments of manufacturing an expandable electrode assembly, electrodes and corresponding conductive traces may be built (e.g., disposed) onto the outer layer of the top surface and/or the outer layer of the bottom surface of the balloon member using the combination of copper and a thermoplastic-comprising material. In some aspects, copper is disposed onto the balloon material. For example, copper may be laminated onto a thermoplastic sheet. The copper may be coated with a photoresist and a desired circuit layer may be imaged onto the photoresist according to known approaches in the art. In various aspects, photochemical etching methods are used to selectively remove copper using a chemical reagent to create an etched pattern (e.g., the circuit layout). In some aspects, the photoresist circuit layout may be gold plated. The combination of photoresist and imaging processes etch away unwanted copper thereby forming a plurality of electrodes and a plurality of corresponding traces. Accordingly, electrodes and corresponding conductive traces may be built (e.g., disposed) onto the balloon material (e.g., a thermoplastic sheet). Apertures corresponding to the formed electrodes may be formed according to any of the aspects described herein to expose the electrode material. In various embodiments, the manufacturing process may be electrolytic or electroless. For example, different manufacturing processes may provide a different hardness, such as for gold or the like.

Figure 12A:
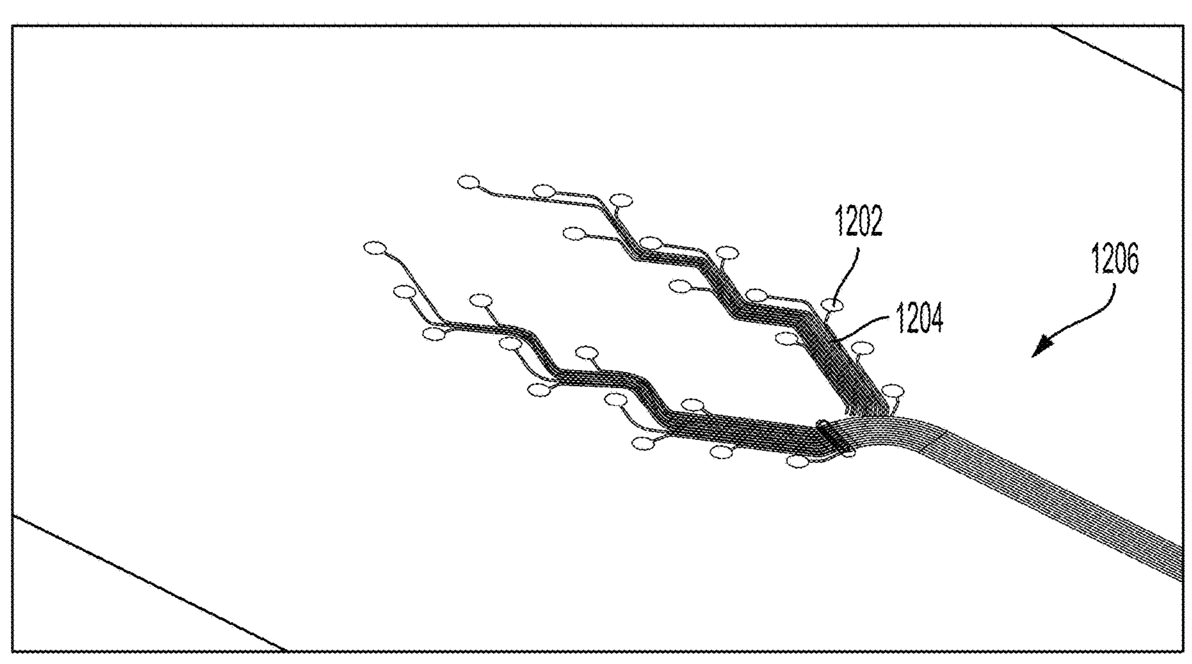
FIGS. 12A and 12B are perspective exploded views of an expandable electrode assembly, in accordance with embodiments of the present disclosure.
Figure 12B:
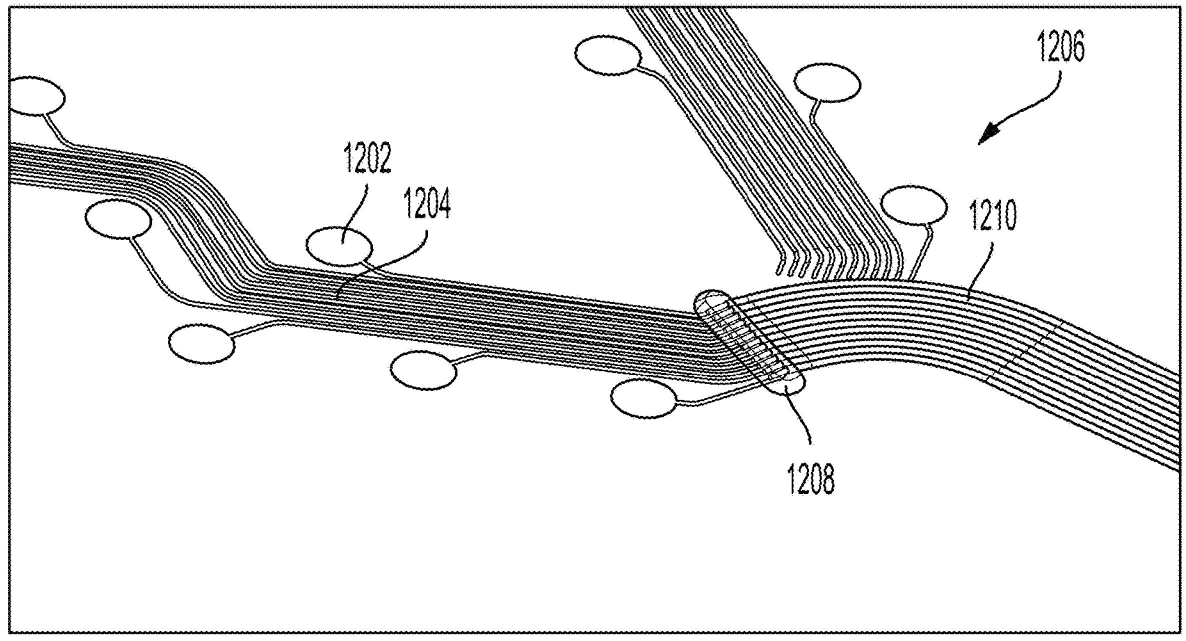

As shown in FIG. 12A, a plurality of electrodes 1202 and a plurality of conductive traces 1204 corresponding to the plurality of electrodes 1202 are deposited onto a layer of balloon material 1206. FIG. 12B shows a close-up view of the conductive traces 1204 on the layer of balloon material 1206 having a conductive adhesive 1208 extending along the ends of the conductive traces 1204. As further shown in FIGS. 12A-12B, a ribbon cable 1210 may be coupled to the conductive traces 1204 and extend from the conductive traces 1204, in at least some embodiments.

Figure 13:
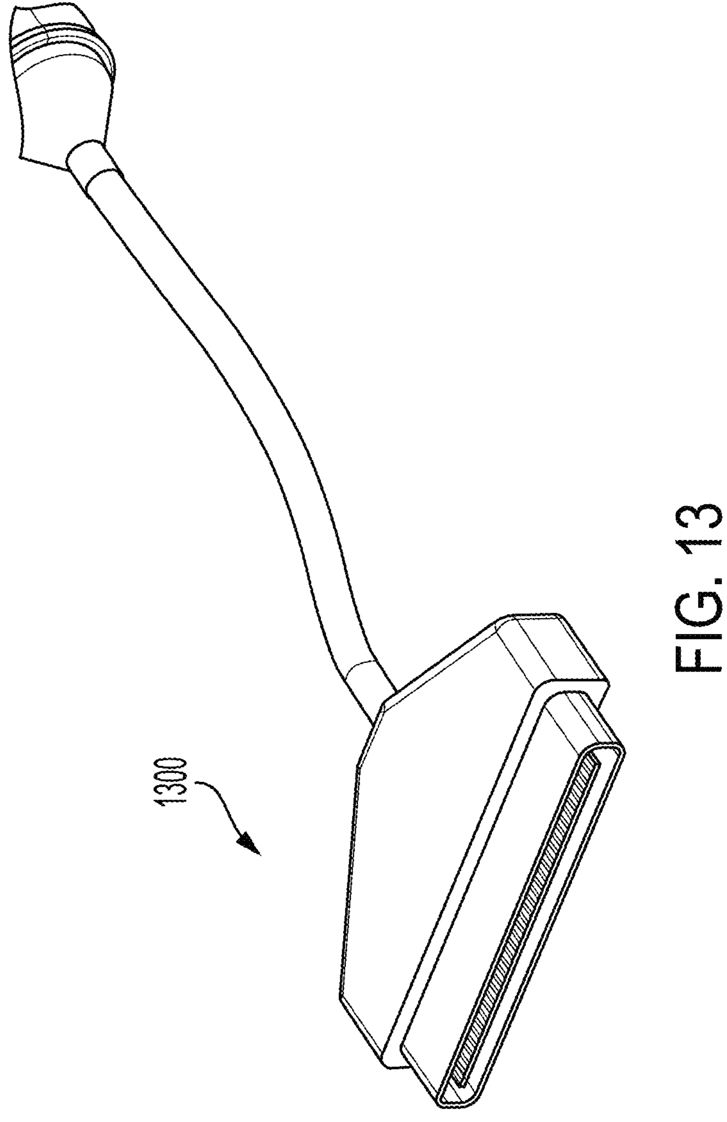
FIG. 13 depicts a perspective view of a connector for a catheter, in accordance with embodiments of the present disclosure.

FIG. 13 depicts a connector 1300 for a catheter system, in accordance with embodiments of the present disclosure. Various signals gathered from the electrodes on the expandable electrode assembly can be transmitted via the connector 1300 to a system for analyzing the signal e.g., to determine localization. The connector 1300 is configured to electronically couple and physically couple the expandable electrode assembly to a mapping and/or therapeutic system for sensing and/or energy delivery (e.g., such as system 108 described in detail with reference to FIG. 1).

Figure 14:
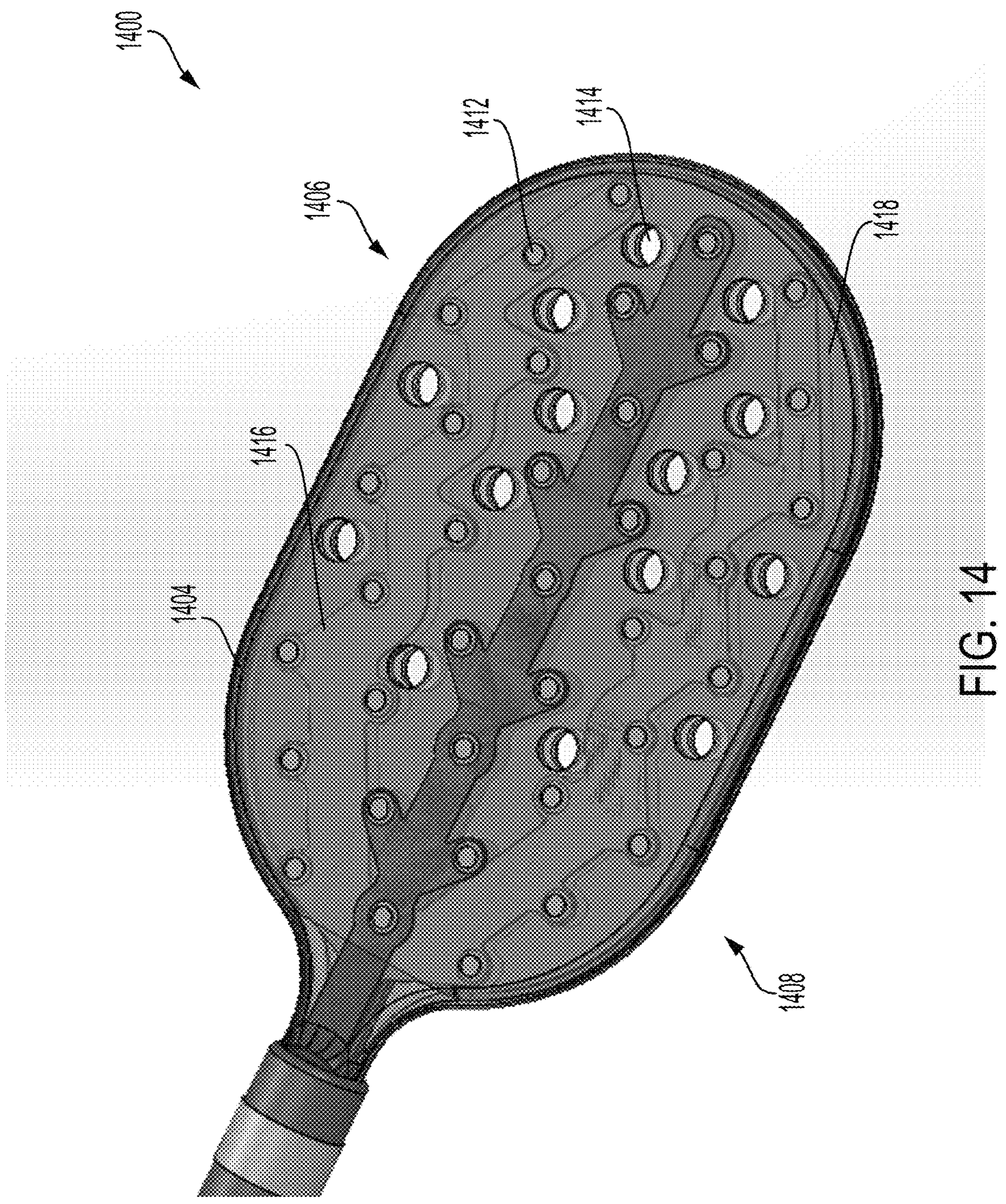
FIG. 14 depicts a perspective view of an expandable electrode assembly having through-holes, in accordance with embodiments of the present disclosure.

FIG. 14 depicts a perspective view of an expandable electrode assembly having through-holes, in accordance with embodiments of the present disclosure. FIG. 14 illustrates an example of an expandable electrode assembly 1400 according to some embodiments. The expandable electrode assembly 1400 includes a balloon member 1404 having a first delivery configuration, and a second deployed configuration, as described in detail above. Balloon member 1404 may include any size, shape, configuration, pattern, etc., as described with respect to other embodiments.

As shown, the balloon member 1404 comprises a top surface 1406 and a bottom surface 1408. In various embodiments, a plurality of electrodes 1412 extend within and are exposed through the top surface 1406 and/or the bottom surface 1408 of the balloon member 1404. For example, a first plurality of electrodes 1412 may extend within and be exposed through the top surface 1406 and a second plurality of electrodes (not shown) may extend within and be exposed through the bottom surface 1408.

In some embodiments, each of the top surface 1406 and the bottom surface 1408 of the balloon member 1404 may optionally include a plurality of through-holes 1414 interspersed between at least some of the electrodes 1412. For example, the balloon member 1404 may be a fenestrated two-sided balloon member 1404. In particular, the plurality of through-holes 1414 may extend through the balloon member 1404 from the top surface 1406 to the bottom surface 1408 according to at least some embodiments. According to at least some embodiments, the through-holes 1414 may be circular, as shown in FIG. 14. The through-holes 1414 may be elongate, square, rectangular, or any combination thereof. In some embodiments, the through-holes 1414 may separate the conductive and mechanical support traces (e.g., such as the plurality of conductive traces 412 shown at least in FIGS. 4A, 4B, 5A, and 7). The opposing surfaces of the balloon member 1404 may be bound by portions of the through-holes 1414 connecting through-holes 1414 through the top surface 1406 to corresponding through-holes 1414 through the bottom surface 1408. The portions of the through-holes 1414 which may connect the top surface 1406 and the bottom surface 1408 may control an inflated thickness of the balloon member 1404 according to some embodiments.

In embodiments where the balloon member 1404 may be expanded or otherwise inflated (as described in detail above with respect to other FIGS.), portions of the balloon member 1404 proximate to the plurality of through-holes 1414 may swell or otherwise protrude outward from the perimeters of the through-holes 1414 for producing better contact with the target tissue during treatment (e.g., by increasing the surface area in contact with the target tissue). Such a plurality of through-holes 1414 would allow exposure of the electrodes on all sides and along the top surface 1406 and the bottom surface 1408 to the target tissue.

Figure 15:
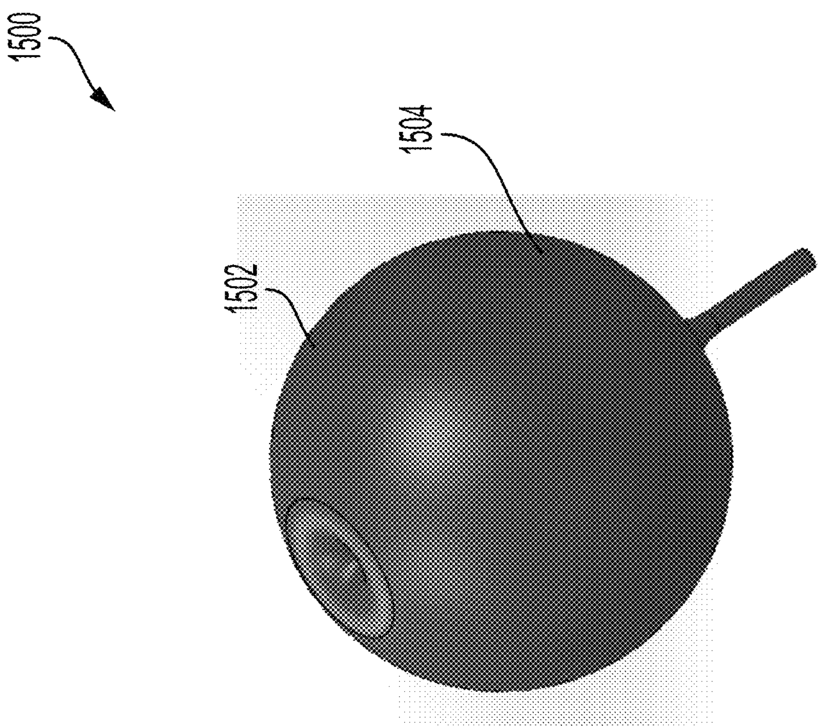
FIG. 15 depicts a perspective view of an expandable electrode assembly, in accordance with embodiments of the present disclosure.

FIG. 15 depicts a perspective view of an expandable electrode assembly, in accordance with embodiments of the present disclosure. FIG. 15 illustrates the expandable electrode assembly as a conductive balloon assembly 1500 according to some embodiments. The conductive balloon assembly 1500 may have a first delivery configuration, and a second deployed configuration, as described in detail above. conductive balloon assembly may include any size, shape, configuration, pattern, etc., as described with respect to other embodiments.

As shown in FIG. 15, conductive balloon member 1500 includes a balloon 1502. To deliver PFA therapy, the conductive balloon member 1500 is maneuvered into a patient's anatomy, and energy is delivered while the balloon 1502 is in contact with patient tissue to generate one or more lesions. In some embodiments, the balloon 1502 is relatively compliant (i.e., stretchable) and has a relatively low durometer. Alternatively, the balloon 1502 may have any suitable characteristics. For example, in some embodiments, the balloon 1502 is relatively non-compliant (e.g., rigid). The balloon 1502 may include a conductive material 1504. For example, in some embodiments, the conductive material 1504 includes polyurethane, polyolefin, and/or Pebax® (e.g., Pebax MH1657, MV1074, MV2080, and/or MH2030) (Pebax is a registered trademark of Arkema France, Colombes, France). Alternatively, the conductive material 1504 may include any suitable material. In some embodiments, the conductive material 1504 has a conductivity in a range from $1\times10^{-2}$ Siemens per meter (S/M) to $1\times10^{-7}$ S/m. In some embodiments, materials for the conductive material 1504 and/or other components of balloon 1502 are selected to facilitate reducing impedance, generating larger lesions at lower applied voltages, and/or mitigating temperature increase of the tissue.

Figure 16:
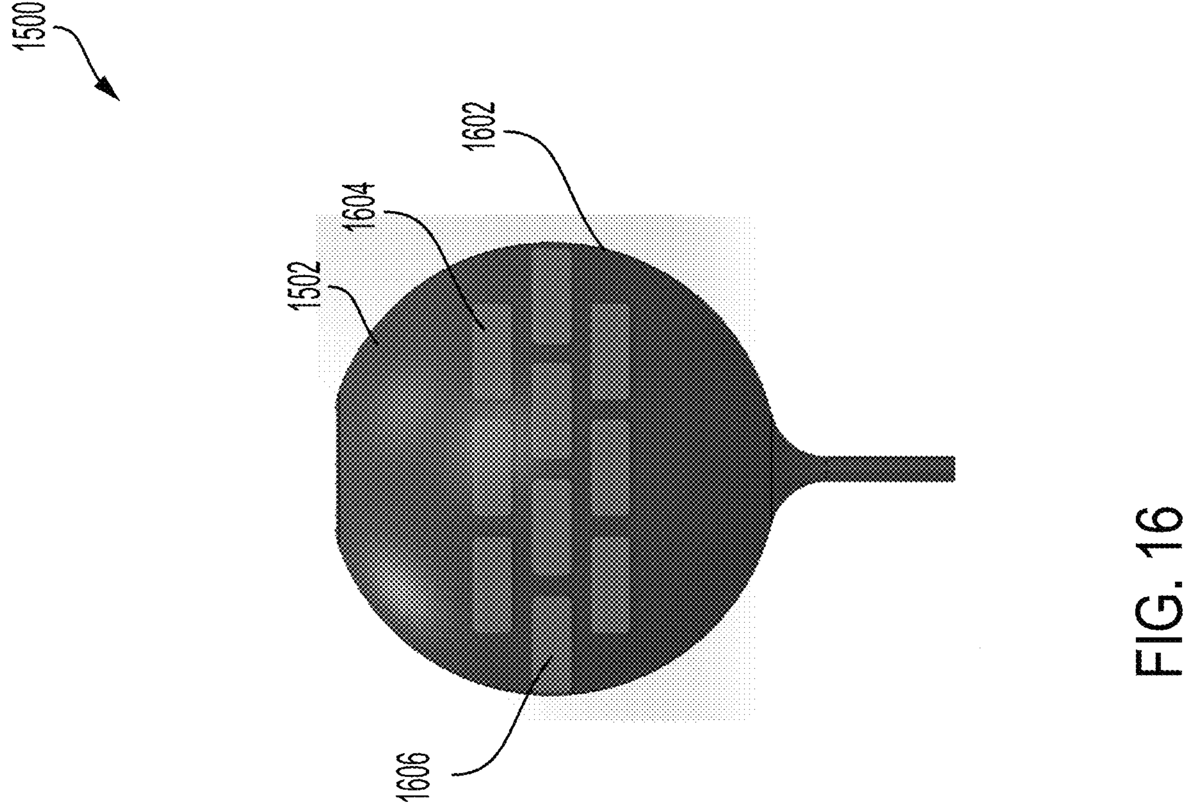
FIG. 16 depicts a perspective view of an expandable electrode assembly, in accordance with embodiments of the present disclosure.

According to at least some embodiments, at least some portions of the balloon 1502 may be covered or masked with a non-conductive masking material. In the embodiment of FIG. 15, substantially all of conductive material 1504 is exposed (i.e., no non-conductive masking material is used). As shown in FIG. 16, a non-conductive masking material 1602 covers a majority of the balloon 1502 such that a plurality of windows 1604 of exposed conductive material 1606 are defined. In this embodiment, the windows 1604 are generally rectangular in shape, are arranged in a brick-like pattern, and are generally aligned with the widest part of the balloon 1502. Alternatively, the windows 1604 may have any suitable shape and/or be arranged in any suitable pattern/location on the balloon 1502.

In at least some embodiments, the conductive material surfaces of the balloon 1502 (e.g., the entire surface as in FIG. 15 or the windows 1604 as in FIG. 16) may be configured to disperse electrical energy into tissue in contact with balloon 1502 for delivering PFA therapy. The balloon conductivity may be similar to that of blood. In some embodiments, the balloon cavity may be inflated with a conductive material such as saline, half-normal saline, or a mixture of contrast agent and saline. According to these embodiments, the balloon 1502 retains its structure but appears electrically transparent (e.g., as transparent as blood). Accordingly, the conductive balloon embodiment enables three-dimensional electrogram characterization without requiring additional magnetic sensors.

According to some embodiments, at least portions of the conductive material surface(s) of balloon 1502 may be used in conjunction with, or instead of, through-holes (such as through-holes 1414 described in detail above with respect to FIG. 14). If the balloon's effective conductivity is close to that of blood, the function of the vastly more conductive electrodes and conductive traces, as described with respect to other figures, covered with insulative polymer, is not disrupted. In some exemplary embodiments, the surface area of the exposed conductive material on a conductive balloon 1502 may be modified and may not be uniform across the entire surface area of the balloon 1502. For example, a top surface of a conductive balloon 1502, having a configuration such as shown in FIG. 14, may be completely exposed (e.g., as in FIG. 15) and a bottom surface may include one or more windows (e.g., as in FIG. 16).

According to various embodiments, the conductive surfaces may be used instead of, or in addition to, other electrodes on the balloon for mapping and/or treatment. For example, the conductive surfaces may be ganged (electrically coupled) to increase impedance detected by the system for mapping and navigation and then un-ganged for treatment or the like.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

Example Embodiments

In one or more embodiments, a catheter includes an elongate catheter shaft including a proximal end and a distal end. The elongate catheter shaft defines a longitudinal axis. The catheter further includes an expandable assembly. The expandable assembly includes a balloon member having a top surface, a bottom surface, and an interior cavity. Each of the top surface and the bottom surface include an outer facing layer and an inner facing layer. The expandable assembly further includes a top flexible framework disposed between the outer facing layer and the inner facing layer of the top surface of the balloon member, a bottom flexible framework disposed between the outer facing layer and the inner facing layer of the bottom surface of the balloon member, a first plurality of electrodes patterned onto the top flexible framework, and a second plurality of electrodes patterned onto the bottom flexible framework. The first plurality of electrodes are aligned with the second plurality of electrodes. The expandable assembly includes a plurality of conductive traces disposed on each of the flexible frameworks and each of the plurality of conductive traces electrically are coupled with a respective one of the first plurality of electrodes and the second plurality of electrodes. The expandable assembly includes a flexible structural element disposed within the interior cavity. Optionally, the flexible structural element includes a nitinol wire looped element extending along the longitudinal axis of the elongate catheter shaft. Optionally, the nitinol wire looped element is disposed between the top flexible framework and the bottom flexible framework. Optionally, the expandable assembly further includes a first delivery configuration and a second deployed configuration. The balloon member may have a flat, concave, or convex shape in the second deployed configuration. The expandable assembly may have an intermediate configuration between the first delivery configuration and the second deployed configuration, and, in the intermediate configuration, the balloon member may be unconstrained from an introducer sheath and uninflated. The balloon member may include a plurality of apertures on the outer facing layer of the top surface and the bottom surface of the balloon member configured to expose the respective first plurality of electrodes and the second plurality of electrodes. A diameter of the plurality of apertures may be the same size or smaller than a diameter of the respective first and second plurality of electrodes. The plurality of apertures may have a diameter in a range from 0.25 mm to 3 mm and the respective first and second plurality of electrodes may have a diameter in a range from 0.25 mm to 3 mm. Optionally, the first and second plurality of electrodes are flush, recessed, or raised with respect to the outer facing layer of the top surface and the bottom surface of the balloon member. Optionally, the elongate catheter shaft includes an oval inflation lumen coupled to the interior cavity of the balloon member and the balloon member in the first delivery configuration is uninflated and in the second deployed configuration is inflated via a liquid or a gas delivered through the oval inflation lumen. Optionally, each of the first plurality of electrodes and the second plurality of electrodes are arranged in horizontal rows relative to the longitudinal axis of the elongate catheter shaft. The horizontal rows may be offset such that each electrode in each row is offset from a respective electrode in an adjacent row. Each of the first plurality of electrodes and the second plurality of electrodes may be arranged in vertical rows parallel to the longitudinal axis of the elongate catheter shaft. The vertical rows may be offset such that each electrode in each row is offset from a respective electrode in an adjacent row. The offset may be 60°. The offset may be in a range from 22.5° to 60°. Each electrode in each row may be equally spaced from adjacent electrodes in the same row and adjacent rows. Each of the first plurality of electrodes and the second plurality of electrodes may be for independent sensing or energy delivery. Each of the electrodes in the first plurality of electrodes and the second plurality of electrodes may be grouped into cliques of three or more electrodes defining a two-dimensional shape. The cliques of electrodes may be in an equilateral triangular shape, each clique having at least three electrodes. The cliques of electrodes may sample electrical characteristics of contacted tissue in at least two substantially transverse directions. Optionally, a center-to-center distance between each of the electrodes in the first plurality of electrodes and the second plurality of electrodes are in a range from 0.5 mm to 4 mm. The catheter may include at least one magnetic position sensor disposed along a distal portion of the elongate catheter shaft. The catheter may include one or more magnetic position sensors disposed on the top flexible framework or on the bottom flexible framework on a distal portion of the expandable assembly. Optionally, the balloon member is rounded in the second deployed configuration. Optionally, the balloon member is a cylindrical or cuboidal linear balloon member in the second deployed configuration. Optionally, the expandable assembly is a basket assembly having a plurality of balloon members, wherein each balloon member is a cylindrical or cuboidal in the second deployed configuration. One or more electrodes of the first plurality of electrodes and/or the second plurality of electrodes deliver pulsed field energy to a tissue.

In one or more embodiments, a catheter includes an elongate catheter shaft including a proximal end and a distal end. The elongate catheter shaft defines a longitudinal axis. The catheter further includes an expandable assembly having a first delivery configuration and a second deployed configuration. The expandable assembly includes a balloon member having a substantially flat shape in the second deployed configuration and includes a top surface and a bottom surface. A first plurality of electrodes extend within and are exposed through the top surface of the balloon member. A second plurality of electrodes extend within and are exposed through the bottom surface of the balloon member. Each of the first plurality of electrodes and the second plurality of electrodes are arranged in horizontal rows relative to the longitudinal axis of the elongate catheter shaft. The horizontal rows are offset such that each electrode in each row is offset from a respective electrode in an adjacent row. Optionally, the offset is 60°. Optionally, the offset is in a range from 22.5° to 60°. Each of the first plurality of electrodes and the second plurality of electrodes may be arranged in vertical rows parallel to the longitudinal axis of the elongate catheter shaft. The vertical rows may be offset such that each electrode in each row is offset from a respective electrode in an adjacent row. Each electrode in each row may be equally spaced from adjacent electrodes in the same row and adjacent rows. Each of the electrodes in the first plurality of electrodes and the second plurality of electrodes may be grouped into cliques of three or more electrodes defining a two-dimensional shape. Optionally, the cliques of electrodes are in an equilateral triangular shape and each clique may include at least three electrodes. The cliques of electrodes may sample electrical characteristics of contacted tissue in at least two substantially transverse directions. Optionally, a center-to-center distance between each of the electrodes in the first plurality of electrodes and the second plurality of electrodes is 0.5 mm. Optionally, a center-to-center distance between each of the electrodes in the first plurality of electrodes and the second plurality of electrodes is in a range from 0.5 mm to 4 mm. The catheter may further include a flexible structural element disposed within an interior cavity of the balloon member. The flexible structural element may include a nitinol wire looped element extending along the longitudinal axis of the elongate catheter shaft. Each of the top surface and bottom surface of the balloon member may include an outer facing layer and an inner facing layer. The catheter may further include a plurality of electrodes disposed onto the outer facing layer of the top surface and the outer facing layer of the bottom surface and a plurality of conductive traces disposed onto the outer facing layer of the top surface and the outer facing layer of the bottom surface. Optionally, the balloon member includes thermoplastic polyurethanes (TPUs), thermoplastic elastomers (TPEs), polyamides including nylons or Pebax, ethylene vinyl acetates (EVAs), polyvinylidene fluoride (PVDF), polyvinyl chloride (PVC), silicon, silicone, and/or composite materials thereof. Optionally, the catheter further includes a top flexible framework disposed between the outer facing layer and the inner facing layer of the top surface of the balloon member, a bottom flexible framework disposed between the outer facing layer and the inner facing layer of the bottom surface of the balloon member, the first plurality of electrodes disposed on the top flexible framework, the second plurality of electrodes disposed on the bottom flexible framework; and a plurality of conductive traces disposed on each of the flexible frameworks where each of the plurality of conductive traces electrically coupled with a respective one of the first plurality of electrodes and the second plurality of electrodes. The balloon member may include a plurality of apertures on the outer facing layer of the top surface and the bottom surface of the balloon member to expose the respective first plurality of electrodes and the second plurality of electrodes. A diameter of the plurality of apertures may be the same size or smaller than a diameter of the respective first and second plurality of electrodes. The elongate catheter shaft may include an oval inflation lumen coupled to the interior cavity of the balloon member where the balloon member in the first delivery configuration is uninflated and in the second deployed configuration is inflated via a liquid or a gas delivered through the oval inflation lumen. Optionally, the catheter may include at least one magnetic position sensor disposed along a distal portion of the elongate catheter shaft. Optionally, the catheter may include one or more magnetic position sensors disposed on a distal portion of the expandable assembly. Optionally, each of the first plurality of electrodes and the second plurality of electrodes are configured for independent sensing or energy delivery. The expandable assembly may have an intermediate configuration between the first delivery configuration and the second deployed configuration, where, in the intermediate configuration, the balloon member is unconstrained from an introducer sheath and uninflated. One or more electrodes of the first plurality of electrodes and/or the second plurality of electrodes deliver pulsed field energy to a tissue.

In one or more embodiments, a catheter includes an elongate catheter shaft includes a proximal end and a distal end. The elongate catheter shaft defines a longitudinal axis. The catheter further includes an expandable assembly having a first delivery configuration and a second deployed configuration including a substantially planar shape. The expandable assembly includes a top surface, a bottom surface, a flexible framework disposed between the top surface and the bottom surface, and a plurality of electrodes patterned onto the flexible framework. The plurality of electrodes are arranged in horizontal rows relative to the longitudinal axis of the elongate catheter shaft. The horizontal rows are offset such that each electrode in each row is offset from a respective electrode in an adjacent row. The catheter further includes a plurality of conductive traces disposed on the flexible framework and electrically coupled with the plurality of electrodes and a flexible structural element disposed within the expandable assembly. Optionally, the expandable assembly comprises a silicone pad. Optionally, the expandable assembly comprises an interior cavity between the top surface and the bottom surface. Optionally, the expandable assembly does not comprise an interior cavity between the top surface and the bottom surface. One or more electrodes of the plurality of electrodes deliver pulsed field energy to a tissue.

In one or more embodiments, a catheter includes an elongate catheter shaft including a proximal end and a distal end. The elongate catheter shaft defines a longitudinal axis. The catheter includes an expandable assembly having a first delivery configuration and a second deployed configuration. The expandable assembly includes a balloon member having a top surface, a bottom surface, and an interior cavity. A flexible framework is disposed between the top surface and the bottom surface. The expandable assembly includes a plurality of electrodes patterned onto the flexible framework, a plurality of conductive traces disposed on the flexible framework and electrically coupled with the plurality of electrodes, and a flexible structural element disposed within the interior cavity. One or more electrodes of the plurality of electrodes deliver pulsed field energy to a tissue.

In one or more embodiments, a catheter includes an elongate catheter shaft including a proximal end and a distal end. The elongate catheter shaft defines a longitudinal axis. The catheter includes an expandable assembly having a linear balloon member having a top surface, a bottom surface, and an interior cavity. Each of the top surface and the bottom surface have an outer facing layer and an inner facing layer. The expandable assembly includes a top flexible framework disposed between the outer facing layer and the inner facing layer of the top surface of the balloon member, a bottom flexible framework disposed between the outer facing layer and the inner facing layer of the bottom surface of the balloon member, a first plurality of electrodes patterned onto the top flexible framework, and a second plurality of electrodes patterned onto the bottom flexible framework. The first plurality of electrodes are aligned with the second plurality of electrodes. The expandable assembly includes a plurality of conductive traces disposed on each of the flexible frameworks and each of the plurality of conductive traces are electrically coupled with a respective one of the first plurality of electrodes and the second plurality of electrodes. The expandable assembly includes a flexible structural element disposed within the interior cavity. One or more electrodes of the first plurality of electrodes and/or the second plurality of electrodes deliver pulsed field energy to a tissue.

In one or more embodiments, a catheter includes an elongate catheter shaft including a proximal end and a distal end. The elongate catheter shaft defines a longitudinal axis. The catheter includes an expandable assembly having a hoop-shaped balloon member having a top surface, a bottom surface, and an interior cavity. Each of the top surface and the bottom surface have an outer facing layer and an inner facing layer. The expandable assembly includes a top flexible framework disposed between the outer facing layer and the inner facing layer of the top surface of the balloon member, a bottom flexible framework disposed between the outer facing layer and the inner facing layer of the bottom surface of the balloon member, a first plurality of electrodes patterned onto the top flexible framework, and a second plurality of electrodes patterned onto the bottom flexible framework. The first plurality of electrodes are aligned with the second plurality of electrodes. The expandable assembly includes a plurality of conductive traces disposed on each of the flexible frameworks and each of the plurality of conductive traces are electrically coupled with a respective one of the first plurality of electrodes and the second plurality of electrodes. The expandable assembly includes a flexible structural element disposed within the interior cavity. One or more electrodes of the first plurality of electrodes and/or the second plurality of electrodes deliver pulsed field energy to a tissue.

In one or more embodiments, a catheter includes an elongate catheter shaft including a proximal end and a distal end. The elongate catheter shaft defines a longitudinal axis. The catheter includes an expandable assembly having a circular balloon member having a top surface, a bottom surface, and an interior cavity. Each of the top surface and the bottom surface have an outer facing layer and an inner facing layer. The expandable assembly includes a top flexible framework disposed between the outer facing layer and the inner facing layer of the top surface of the balloon member, a bottom flexible framework disposed between the outer facing layer and the inner facing layer of the bottom surface of the balloon member, a first plurality of electrodes patterned onto the top flexible framework, and a second plurality of electrodes patterned onto the bottom flexible framework. The first plurality of electrodes are aligned with the second plurality of electrodes. The expandable assembly includes a plurality of conductive traces disposed on each of the flexible frameworks and each of the plurality of conductive traces are electrically coupled with a respective one of the first plurality of electrodes and the second plurality of electrodes. The expandable assembly includes a flexible structural element disposed within the interior cavity. One or more electrodes of the first plurality of electrodes and/or the second plurality of electrodes deliver pulsed field energy to a tissue.

In one or more embodiments, a catheter includes an elongate catheter shaft including a proximal end and a distal end. The elongate catheter shaft defines a longitudinal axis. The catheter includes an expandable assembly having a balloon member having a top surface, a bottom surface, and an interior cavity. Each of the top surface and the bottom surface have an outer facing layer and an inner facing layer. The expandable assembly includes a top flexible framework disposed between the outer facing layer and the inner facing layer of the top surface of the balloon member, a bottom flexible framework disposed between the outer facing layer and the inner facing layer of the bottom surface of the balloon member, a first plurality of electrodes patterned onto the top flexible framework, and a second plurality of electrodes patterned onto the bottom flexible framework. The first plurality of electrodes are aligned with the second plurality of electrodes. The expandable assembly includes a plurality of conductive traces disposed on each of the flexible frameworks and each of the plurality of conductive traces are electrically coupled with a respective one of the first plurality of electrodes and the second plurality of electrodes. The expandable assembly includes a flexible structural element disposed within the interior cavity. The expandable assembly further includes a first delivery configuration and a second deployed configuration, and the expandable assembly has a flat shape in the second deployed configuration. One or more electrodes of the first plurality of electrodes and/or the second plurality of electrodes deliver pulsed field energy to a tissue.

In one or more embodiments, a catheter includes an elongate catheter shaft including a proximal end and a distal end. The elongate catheter shaft defines a longitudinal axis. The catheter includes an expandable assembly having a balloon member having a top surface, a bottom surface, and an interior cavity. Each of the top surface and the bottom surface have an outer facing layer and an inner facing layer. The expandable assembly includes a top flexible framework disposed between the outer facing layer and the inner facing layer of the top surface of the balloon member, a bottom flexible framework disposed between the outer facing layer and the inner facing layer of the bottom surface of the balloon member, a first plurality of electrodes patterned onto the top flexible framework, and a second plurality of electrodes patterned onto the bottom flexible framework. The first plurality of electrodes are aligned with the second plurality of electrodes. The expandable assembly includes a plurality of conductive traces disposed on each of the flexible frameworks and each of the plurality of conductive traces are electrically coupled with a respective one of the first plurality of electrodes and the second plurality of electrodes. The expandable assembly includes a flexible structural element disposed within the interior cavity. The expandable assembly further includes a first delivery configuration and a second deployed configuration, and the expandable assembly has a convex shape in the second deployed configuration. One or more electrodes of the first plurality of electrodes and/or the second plurality of electrodes deliver pulsed field energy to a tissue.

In one or more embodiments, a catheter includes an elongate catheter shaft including a proximal end and a distal end. The elongate catheter shaft defines a longitudinal axis. The catheter includes an expandable assembly having a balloon member having a top surface, a bottom surface, and an interior cavity. Each of the top surface and the bottom surface have an outer facing layer and an inner facing layer. The expandable assembly includes a top flexible framework disposed between the outer facing layer and the inner facing layer of the top surface of the balloon member, a bottom flexible framework disposed between the outer facing layer and the inner facing layer of the bottom surface of the balloon member, a first plurality of electrodes patterned onto the top flexible framework, and a second plurality of electrodes patterned onto the bottom flexible framework. The first plurality of electrodes are aligned with the second plurality of electrodes. The expandable assembly includes a plurality of conductive traces disposed on each of the flexible frameworks and each of the plurality of conductive traces are electrically coupled with a respective one of the first plurality of electrodes and the second plurality of electrodes. The expandable assembly includes a flexible structural element disposed within the interior cavity. The expandable assembly further includes a first delivery configuration and a second deployed configuration, and the expandable assembly has a concave shape in the second deployed configuration. One or more electrodes of the first plurality of electrodes and/or the second plurality of electrodes deliver pulsed field energy to a tissue.

In one or more embodiments, for any embodiments described herein, each of the electrodes in the first plurality of electrodes and the second plurality of electrodes are grouped into cliques of four or more electrodes defining a three-dimensional shape. The cliques of four or more electrodes may be configured in an equilateral tetrahedral shape. The cliques of four or more electrodes may be configured in a tri-rectangular tetrahedron.

According to various embodiments, a conductive balloon catheter may include a conductive material configured to dissipate electrical energy into tissue during an ablation procedure. In some embodiments, a non-conductive masking material covering a portion of the conductive material and defining at least one window of exposed conductive material on a surface of the balloon. In at least some embodiments, the conductive material surfaces of the conductive balloon catheter may be configured to disperse electrical energy to deliver PFA therapy.

The use of the terms “a” and “an” and “the” and similar referents in the context of describing the invention (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A pulsed field ablation catheter comprising:

an elongate catheter shaft comprising a proximal end and a distal end, the elongate catheter shaft defining a longitudinal axis; and an expandable assembly, wherein the expandable assembly comprises:

a balloon member comprising a top surface, a bottom surface, and an interior cavity, each of the top surface and the bottom surface comprising an outer facing layer and an inner facing layer;

a top flexible framework disposed between the outer facing layer and the inner facing layer of the top surface of the balloon member;

a bottom flexible framework disposed between the outer facing layer and the inner facing layer of the bottom surface of the balloon member;

a first plurality of electrodes patterned onto the top flexible framework;

a second plurality of electrodes patterned onto the bottom flexible framework, wherein the first plurality of electrodes are aligned with the second plurality of electrodes, wherein one or more electrodes of the first plurality of electrodes and/or the second plurality of electrodes are configured to deliver pulsed field ablation energy to a tissue;

a plurality of conductive traces disposed on each of the flexible frameworks, each of the plurality of conductive traces electrically coupled with a respective one of the first plurality of electrodes and the second plurality of electrodes; and a flexible structural element disposed within the interior cavity.

2. The catheter of claim 1, wherein the one or more electrodes are configured to be activated in unison in a ganged configuration for pulsed field ablation.

3. The catheter of claim 2, wherein the ganged configuration comprises an outer grouping of electrodes of a first polarity and an inner grouping of electrodes of a second polarity.

4. The catheter of claim 1, wherein the one or more electrodes are configured to be activated independent from one another in an un-ganged configuration for pulsed field ablation.

5. The catheter of claim 1, wherein the one of more electrodes comprise a center grouping of electrodes for pulsed field ablation.

6. The catheter of claim 1, wherein each of the first plurality of electrodes and the second plurality of electrodes are further configured for independent sensing.

7. The catheter of claim 1, wherein the balloon member is a conductive balloon member comprising conductive material configured to dissipate electrical energy into tissue during pulsed field ablation.

8. The catheter of claim 7, wherein the one or more electrodes and the conductive balloon are configured to be activated in unison in a ganged configuration.

9. The catheter of claim 7, wherein the one of more electrodes and the conductive balloon are configured to be activated independent from one another in an un-ganged configuration.

10. The catheter of claim 1, further comprising a plurality of through-holes extending between the top surface and the bottom surface and through the interior cavity of the balloon member.

11. The catheter of claim 1, wherein the flexible structural element comprises a nitinol wire looped element extending along the longitudinal axis of the elongate catheter shaft.

12. The catheter of claim 11, wherein the nitinol wire looped element is disposed between the top flexible framework and the bottom flexible framework.

13. The catheter of claim 1, wherein the expandable assembly further comprises a first delivery configuration and a second deployed configuration.

14. The catheter of claim 13, wherein the balloon member has a flat, concave, or convex shape in the second deployed configuration.

15. The catheter of claim 13, wherein the expandable assembly has an intermediate configuration between the first delivery configuration and the second deployed configuration, wherein, in the intermediate configuration, the balloon member is unconstrained from an introducer sheath and uninflated.

16. The catheter of claim 1, wherein each of the first plurality of electrodes and the second plurality of electrodes are arranged in horizontal rows relative to the longitudinal axis of the elongate catheter shaft, wherein the horizontal rows are offset such that each electrode in each row is offset from a respective electrode in an adjacent row.

17. The catheter of claim 1, wherein each of the first plurality of electrodes and the second plurality of electrodes are arranged in vertical rows parallel to the longitudinal axis of the elongate catheter shaft, wherein the vertical rows are offset such that each electrode in each row is offset from a respective electrode in an adjacent row.

18. The catheter of claim 16, wherein the offset is 60°.

19. The catheter of claim 16, wherein the offset is in a range from 22.5° to 60°.

20. The catheter of claim 16, wherein each electrode in each row is equally spaced from adjacent electrodes in the same row and adjacent rows.

* * * * *